US012643927B2

(12) United States Patent
Rising et al.

(10) Patent No.: US 12,643,927 B2
(45) Date of Patent: ***Jun. 2, 2026

(54) ENGINEERED SPIDER SILK PROTEINS AND USES THEREOF

(71) Applicant: SPIBER TECHNOLOGIES AB, Stockholm (SE)

(72) Inventors: Anna Rising, Uppsala (SE); Jan Johansson, Stockholm (SE); Marlene Andersson, Uppsala (SE)

(73) Assignee: SPIBER TECHNOLOGIES AB, Stockholm (SE)

( * ) Notice: Subject to any disclaimer, the term of this patent is extended or adjusted under 35 U.S.C. 154(b) by 948 days.

This patent is subject to a terminal disclaimer.

(21) Appl. No.: 17/895,320

(22) Filed: Aug. 25, 2022

(65) Prior Publication Data

US 2023/0070786 A1     Mar. 9, 2023

Related U.S. Application Data

(62) Division of application No. 16/314,501, filed as application No. PCT/EP2017/066119 on Jun. 29, 2017, now Pat. No. 11,524,984.

(30) Foreign Application Priority Data

Jul. 1, 2016     (EP) ..................................... 16177521

(51) Int. Cl.
    C07K 14/435        (2006.01)
    B33Y 70/00         (2020.01)
    C12N 5/00          (2006.01)

(52) U.S. Cl.
    CPC ........ C07K 14/43518 (2013.01); B33Y 70/00 (2014.12); C12N 5/0018 (2013.01); C12N 5/0062 (2013.01); *C12N 2513/00* (2013.01); *C12N 2533/50* (2013.01)

(58) Field of Classification Search
    CPC .......................... C07K 14/43518; B33Y 70/00; C12N 5/0018; C12N 5/0062; C12N 2513/00; C12N 2533/50
    See application file for complete search history.

(56) References Cited

U.S. PATENT DOCUMENTS

| | | | |
|---|---|---|---|
| 8,642,734 B2 * | 2/2014 | Johansson ........ | C07K 14/43518 530/353 |
| 10,662,230 B2 | 5/2020 | Hedhammar | |
| 11,524,984 B2 * | 12/2022 | Rising .............. | C07K 14/43518 |
| 2007/0260039 A1 | 11/2007 | Karatzas et al. | |
| 2014/0287433 A1 | 9/2014 | Weingart et al. | |
| 2015/0119554 A1 | 4/2015 | Hedhammar et al. | |
| 2018/0282380 A1 | 10/2018 | Kittleson et al. | |

FOREIGN PATENT DOCUMENTS

| | | | |
|---|---|---|---|
| EP | 2 644 619 A1 | 10/2013 | |
| JP | 2013-96037 A | 5/2013 | |
| WO | WO 03/057720 A2 | 7/2003 | |
| WO | WO 03/057727 A1 | 7/2003 | |
| WO | WO 2007/078239 A2 | 7/2007 | |
| WO | WO 2012/055854 A1 | 5/2012 | |
| WO | WO 2013/164404 A1 | 11/2013 | |
| WO | WO 2015/036619 A1 | 3/2015 | |
| WO | WO 2015/042164 A2 | 3/2015 | |
| WO | WO 2017/081239 A1 | 5/2017 | |
| WO | WO 2010/123450 A1 | 10/2018 | |

OTHER PUBLICATIONS

Adrianos et al., "Nephila clavipes Flagelliform silk-like GGX motifs contribute to extensibility and spacer motifs contribute to strength in synthetic spider silk fibers," Biomacromolecules, 2013, 14:1751-1760.
Albertson et al., "Effects of different post-spin stretching conditions on the mechanical properties of synthetic spider silk fibers," J. Mech. Behav. Biomed. Mater., 2014, 29:225-234, (2014).
Anderson, M., et al., "Carbonic Anhydrase Generates CO2 and H+ That Drive Spider Silk Formation via Opposite Effects on the Terminal Domains," PLOS Biology, Aug. 2014, vol. 12, issue 8, pp. 1-14.
Copeland et al., "Development of a Process for the Spinning of Synthetic Spider Silk," ACS Biomaterials Science and Engineering, 2015, 1:577-584.
Eisoldt et al., (2011) Decoding the secrets of spider silk, Materialstoday, vol. 4, No. 3, pp. 80-86.
Gao, Z., et al., "Structural Characterization of Minor Ampullate Spidroin Domains and Their Distinct Roles in Fibroin Solubility and Fiber Formation," PLOS ONE, Feb. 2013, vol. 8, issue 2, pp. 1-11.
Garb et al., (2005) Modular evolution of egg case silk genes across orb-weaving spider superfamilies, Proc. Natl. Acad. Sci. USA., vol. 102, pp. 11379-11384.

(Continued)

*Primary Examiner* — Manjunath N Rao
*Assistant Examiner* — Erica Nicole Jones-Foster
(74) *Attorney, Agent, or Firm* — Birch, Stewart, Kolasch & Birch, LLP

(57)     ABSTRACT

A recombinant spider silk protein, consisting of no more than 800 amino acids, comprising a set of domains arranged according to the formula (NT)-REP-CT, wherein: the optional NT-domain, if present, comprises a sequence of 100 to 160 amino-acid residues derived from the N-terminal domain of a spider silk protein; the REP-domain comprises a sequence of 30 to 600 amino acid residues derived from the repetitive segment of a spider silk protein; and the CT-domain comprises a sequence of 70 to 120 amino acid residues derived from the C-terminal domain of a spider silk protein selected from: a sequence of 72 to 110 amino acid residues derived from the C-terminal domain of a spider silk protein, wherein the sequence comprises at least 7 residues independently selected from K, R, E and D; a sequence having at least 85% identity to SEQ ID NO: 15 or any one of SEQ ID NOs: 62-65 or 67-73; and a sequence having at least 70% identity to SEQ ID NOs: 64 or any one of SEQ ID NOs: 62-65 or 67-73, wherein the sequence comprises at least 7 residues independently selected from K, R, E and D.

23 Claims, 21 Drawing Sheets

Specification includes a Sequence Listing.

(56)          References Cited

OTHER PUBLICATIONS

Garb et al., (2010) Untangling spider silk evolution with spidroin terminal domains, BMC Evol. Biol., vol. 10, pp. 243-243.

Hagn, F., et al., "A conserved spider silk domain acts a molecular switch that controls fibre assembly," Nature, May 13, 2010, vol. 465, pp. 239-242.

Hagn, F., et al., "A conserved spider silk domain acts as a molecular switch that controls fibre assembly," Nature, May 13, 2010, vol. 465, pp. 1-2 (abstract).

Heidebrecht et al., "Biomimetic fibers made of recombinant spidroins with the same toughness as natural spider silk," Adv Mater, 2015, 27:2189-2194.

Lazaris, A., et al., "Spider Silk Fibers Spun from Soluble Recombinant Silk Produced in Mammalian Cells," Science, Jan. 18, 2002, vol. 295, pp. 472-476.

PCT International Search Report and Written Opinion in International Appln. No. PCT/EP2017/066119, dated Sep. 10, 2017, 10 pages.

Plaza et al., "Relationship between microstmcture and mechanical properties in spider silk fibers: identification of two regimes in the microstructural changes," Soft Matter, 2012, 8:6015-6026.

Rising et al., "N-Terminal Nonrepetitive Domain Common to Dragline, Flagelliform, and Cylindriform Spider Silk Proteins," Biomacromolecules, 2006, 7:3120-3124.

Rising et al., "Spider silk proteins: recent advances in recombinant production, structure-function relationships and biomedical applications," Cell. Mol. Life Sci., 2011, 68:169-184.

Shen & Murphy, "Solvent effects on self-assembly of beta-amyloid peptide," Biophys J. Aug. 1995, 69(2):640-51.

Teule et al., "Modifications of spider silk sequences in an attempt to control the mechanical properties of the synthetic fibers," J Mater Sci., 2007, 42:8974-8985.

Tokareva, O., et al., "Recombinant DNA production of spider silk proteins," Microbial Biotechnology, Nov. 2013, Thermatic Issue on Biomaterials, vol. 6, pp. 651-663.

Andersson et al., "Biomimetic spinning of artificial spider silk from a chimeric minispidroin," Nature Chemical Biology, vol. 13, 2017, pp. 262-266.

Askarieh et al., "Self-assembly of spider silk proteins is controlled by a pH-sensitive relay," Nature, vol. 465, 2010, pp. 236-239.

Extended European Search Report for European Application No. 22187817.6, dated Feb. 13, 2023.

* cited by examiner

```
Ea MaSp1   SHTTPWTNPGLAENFMNSFMQGLSSMPGFTASQLDDMSTIAQSMVQSIQSLAAQGRTSPNKLQALNMAFA
Lg MaSp1   QANTPWSSKANADAFINSFISSAQNTGSFSQDQMDMSLIGNTLMTAMDNMG--GRITPSKLQALDMAFA
Lh MaSp1   QANTPWSSKANADAFINSFISAASNTGSFSQDQMEDMSLIGNTLMAAMDNMG--GRITPSKLQALDMAFA
Nc MaSp1   -QNTPWSSTELADAFINAFMNEAGRTGAFTADQLDDMSTIGDTIKTAMDKMARSNKSSKGKLQALNMAFA
At MaSp2   QGATPWENSQLAESFISRFLRFIGQSGAFSPNQLDDMSSIGDTLKTAIEKMAQSRKSSKSKLQALNMAFA
Lg MaSp2   ---LRWSSKDNADRFINAFLQAASNSGAFSSDQVDDMSVIGNTLMTAMDNMG--GRITPSKLQALDMAFA
Lh MaSp2   QANTPWSSKENADAFIGAFMNAASQSGAFSSDQIDDMSVISNTLMAAMDNMG--GRITQSKLQALDMAFA
Nlm MaSp2  QANTPWSDTATADAFIQNFLGAVSGSGAFTPDQLDDMSTVGDTIMSAMDKMARSNKSSKSKLQALNMAFA
Nc MaSp2   QARSPWSDTATADAFIQNFLAAVSGSGAFTSDQLDDMSTIGDTIMSAMDKMARSNKSSQHKLQALNMAFA
Ab CySp1   AVPSVFSSPNLASGFLQCLTFGIGNSPAFPTQEQQDLDALAQVILNAVSSNTGATASAR--AQALSTALA
Ncl CySp1  PVPSVFSSPSLASGFLGCLTTGIGLSPAFPFQEQQDLDDLAKVILSAVTSNTDTSKSAR--AQALSTALA
Lh TuSp1   ASVNIFNSPNAATSFLNCLRSNIESSPAFPFQEQADLDSIAEVILSDVSS-VNTASSAT--SLALSTALA
Nc flag    IANSPFSNPNTAEAFARSFVSNIVSSGEFGAQGAEDFDDIIQSLIQAQ-SMGKGRHDTKAKAKAMQVALA
Nlm flag   IVNSPFSNPNTAEAFARSFVSNVVSSGEFGAQGAEDFDDIIQSLIQAQ-SMGKGRHDTKAKAKAMQVALA Ea MaSp1   SSMAEIAASEEGGGSLSTKTSSIASAMSNAFLQTTGVVNQPFINEITQLVSMFAQAGMNDV
Lg MaSp1   SSVAEIAASEG--GDLGVTTNAIADALTSAFYQTTGVVNNRFISEIRSLISMFAQASANDV
Lh MaSp1   SSVAEIAASEG--GDLGVTTNAIADALTSAFYQTTGVVNSRFISEIRSLIGMFAQASANDV
Nc MaSp1   SSMAEIAAVEQGGLSVDAKTNAIADSLNSAFYQTTGAANPQFVNEIRSLINMFAQSSANEV
At MaSp2   SSMAEIAVAEQGGLSLEAKTNAIASALSAAFLETTGYVNQQFVNEIKTLIFMIAQASSNEI
Lg MaSp2   SSVAEIAVADG--QNVGGATNAISNALRSAFYQTTGVVNQFISEISNLINMFAQVSANEV
Lh MaSp2   SSVAEIAVADG--QNVGAATNAISDALRSAFYQTTGVVNQFITGISSLIGMFAQVSGNEV
Nlm MaSp2  SSMAEIAAVEQGGQSMDVKTNAIANALDSAFYMTTGSTNQQFVNEMRSLINMLSAAAVNEV
Nc MaSp2   SSMAEIAAVEQGGMSMAVKTNAIVDGLNSAFYMTTGAANPQFVNEMRSLISMISAASANEV
Ab CySp1   SSLTDLLIAESAESNYSNQLSELTGILSDCFIQTTGSDNPAFVSRIQSLISVLSQNADTNI
Ncl CySp1  SSLADLLISESSGSSYQTQISALTNILSDCFVTTGSNNPAFVSRVQTLIGVLSQSSSNAI
Lh TuSp1   SSLAELLVTESAEEDIDNQVVALSTILSQCFVETTGSPNPAFVASVKSLLGVLSQSASNYE
Nc flag    SSIAELVIAESSGGDVQRKTNVISNALRNALMSTTGSPNEEFVHEVQDLIQMLSQEQINEV
Nlm flag   SSIAELVIAESSGGDVQRKTNVISNALRNALMSTTGSPNEEFVHEVQDLIQMLSQEQINEV
```

Fig. 13
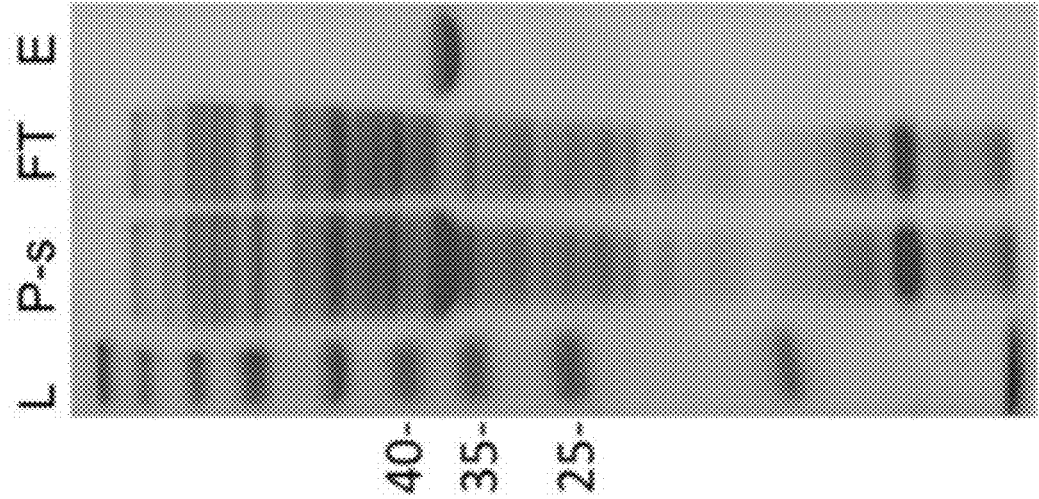
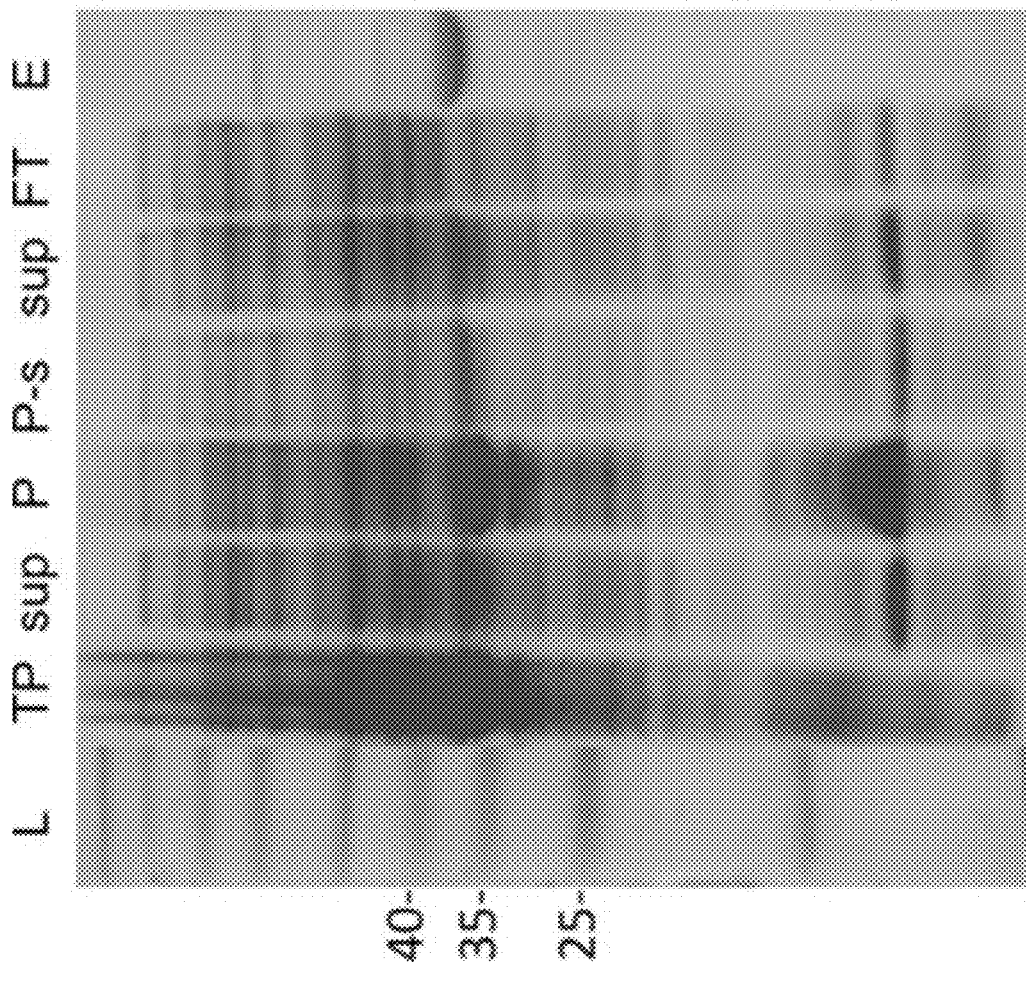

```
                              SEQUENCE LISTING

Sequence total quantity: 97
SEQ ID NO: 1            moltype = AA  length = 137
FEATURE                 Location/Qualifiers
VARIANT                 6
                        note = deletion (deltaHis)
source                  1..137
                        mol_type = protein
                        organism = Euprosthenops australis
SEQUENCE: 1
GSGNSHTTPW TNPGLAENFM NSFMQGLSSM PGFTASQLDD MSTIAQSMVQ SIQSLAAQGR   60
TSPNKLQALN MAFASSMAEI AASEEGGGSL STKTSSIASA MSNAFLQTTG VVNQPFINEI  120
TQLVSMFAQA GMNDVSA                                                 137

SEQ ID NO: 2            moltype = AA  length = 131
FEATURE                 Location/Qualifiers
REGION                  1..131
                        note = Consensus sequence derived from spidroin NT fragments
VARIANT                 20
                        note = Leu
VARIANT                 42
                        note = Asn
VARIANT                 42
                        note = Gln
VARIANT                 50
                        note = Ser
VARIANT                 50
                        note = Lys
VARIANT                 56
                        note = Arg
VARIANT                 84
                        note = Leu
VARIANT                 114
                        note = Ser
VARIANT                 121
                        note = Asn
VARIANT                 123
                        note = Leu
VARIANT                 124
                        note = Ser
source                  1..131
                        mol_type = protein
                        organism = synthetic construct
SEQUENCE: 2
QANTPWSSPN LADAFINSFM SAASSSGAFS ADQLDDMSTI GDTLMSAMDN MGRSGKSTKS   60
KLQALNMAFA SSMAEIAAAE SGGGSVGVKT NAISDALSSA FYQTTGSVNP QFVNEIRSLI  120
GMFAQASANE V                                                      131

SEQ ID NO: 3            moltype = AA  length = 1110
FEATURE                 Location/Qualifiers
REPEAT                  7..19
```

-continued

```
REPEAT                   20..42
REPEAT                   43..56
REPEAT                   57..70
REPEAT                   71..83
REPEAT                   84..106
REPEAT                   107..120
REPEAT                   121..134
REPEAT                   135..147
REPEAT                   148..170
REPEAT                   171..183
REPEAT                   184..197
REPEAT                   198..211
REPEAT                   212..234
REPEAT                   235..248
REPEAT                   249..265
REPEAT                   266..279
REPEAT                   280..293
REPEAT                   294..306
REPEAT                   307..329
REPEAT                   330..342
REPEAT                   343..356
REPEAT                   357..370
REPEAT                   371..393
REPEAT                   394..406
REPEAT                   407..420
REPEAT                   421..434
REPEAT                   435..457
REPEAT                   458..470
REPEAT                   471..488
REPEAT                   489..502
REPEAT                   503..516
REPEAT                   517..529
REPEAT                   530..552
REPEAT                   553..566
REPEAT                   567..580
REPEAT                   581..594
REPEAT                   595..617
REPEAT                   618..630
REPEAT                   631..647
REPEAT                   648..661
REPEAT                   662..675
REPEAT                   676..688
REPEAT                   689..711
REPEAT                   712..725
REPEAT                   726..739
REPEAT                   740..752
REPEAT                   753..775
REPEAT                   776..789
REPEAT                   790..803
REPEAT                   804..816
REPEAT                   817..839
REPEAT                   840..853
REPEAT                   854..867
REPEAT                   868..880
REPEAT                   881..903
REPEAT                   904..917
REPEAT                   918..931
REPEAT                   932..945
REPEAT                   946..968
REPEAT                   969..981
REPEAT                   982..998
REPEAT                   999..1013
REPEAT                   1014..1027
REPEAT                   1028..1042
REPEAT                   1043..1059
REPEAT                   1060..1073
REPEAT                   1074..1092
source                   1..1110
                         mol_type = protein
                         organism = Euprosthenops australis
SEQUENCE: 3
QGAGGNAAAA AAAAAAAAAG QGGQGGYGGL GQGGYGQGAG SSAAAAAAAA AAAAAAGRGQ    60
GGYGQGSGGN AAAAAAAAAA AASGQGGQGG QGGQGQGGYG QGAGSSAAAA AAAAAAAAAA   120
GQGQGRYGQG AGGNAAAAAA AAAAAAAGQG GQGGQGGLGQ GGYGQGAGSS AAAAAASAAA   180
AAAGRGQGGY GQGAGGNAAA AAAAAAAAAA AGQGGQGGYG GLGQGGYGQG AGSSAAAAAA   240
AAAAAAAGGQ GGQGQGRYGQ GAGSSAAAAA AAAAAAAAG QGGGYGQGA GGNAAAAAAA   300
AAAAAGQGGQ QGGQGGLGQG GYGQGAGSSA AAAAAAAAA AAGRGQGGYG QGAGGNAAAA   360
AAAAAEAAAA GQGGQGGYGG LGQGGYGQGA GSSAAAAAAA AAAAAAGRGQ GGYGQGAGGN   420
AAAAAAAAAA AAAAGQGGQG GYGGLGQGGY GQGAGSSAAA AAAAAAAAAA GGQGGQGQGR   480
```

-continued

```
YGQGAGSSAA AAAAAAAAAA AAGRGQGGYG QGSGGNAAAA AAAAAAAASG QGSQGGQGGQ   540
GQGGYGQGAG SSAAAAAAAA AAAAASGRGQ GGYGQGAGGN AAAAAAAAAA AAAAGQGGQG   600
GYGGLGQGGY GQGAGSSAAA AAAAAAAAAG GQGGQGQGGY GQGAGSSAAA AAAAAAAAAA   660
AGRGQGGYGQ GSGGNAAAAA AAAAAAASGQ GGQGGQGGQG QGGYGQGAGS SAAAAAAAAA   720
AAAAAGGQGQ GYGQGAGGNA AAAAAAAAAA AAGQGGQGGQ GGLGQGGYGQ GAGSSAAAAA   780
AAAAAAAAAG RGQGGYGQGV GGNAAAAAAA AAAAAAGQGG QGGQGGLGQG GYGQGAGSSA   840
AAAAAAAAAA AAAGRGQGGY GQGSGGNAAA AAAAAAAAS GQGSQGGQGG QGQGGYGQGA   900
GSSAAAAAAA AAAAAASGRG QGGYGQGAGG NAAAAAAAAA AAAAAGQGGQ GGYGGLGQGG   960
YGQGAGSSAA AAAAAAAAAA GGQGGQGQGG YGQGSGGSAA AAAAAAAAAA AAAGRGQGGY   1020
GQGSGGNAAA AAAAAAAAA AAGQGGQGGY GRQSQGAGSA AAAAAAAAAA AAAGSGQGGY   1080
GGQGQGGYGQ SSASASAAAS AASTVANSVS                                   1110
```

```
SEQ ID NO: 4          moltype = AA  length = 23
FEATURE               Location/Qualifiers
REGION                1..23
                      note = Consensus sequence derived from internal repeats of
                       Euprosthenopsaustralis MaSp1
VARIANT               4
                      note = Ser
VARIANT               8
                      note = Tyr
VARIANT               11
                      note = Gln
source                1..23
                      mol_type = protein
                      organism = synthetic construct
SEQUENCE: 4
GQGGQGGQGG LGQGGYGQGA GSS                                          23

SEQ ID NO: 5          moltype = AA  length = 17
FEATURE               Location/Qualifiers
REGION                1..17
                      note = Consensus sequence derived from internal repeats of
                       Euprosthenopsaustralis MaSp1
VARIANT               9
                      note = Arg
VARIANT               14
                      note = Ser
VARIANT               16
                      note = Gly
source                1..17
                      mol_type = protein
                      organism = synthetic construct
SEQUENCE: 5
GQGGQGQGGY GQGAGSS                                                 17

SEQ ID NO: 6          moltype = AA  length = 14
FEATURE               Location/Qualifiers
REGION                1..14
                      note = Consensus sequence derived from internal repeats of
                       Euprosthenopsaustralis MaSp1
VARIANT               2
                      note = Gln
VARIANT               6
                      note = Arg
VARIANT               11
                      note = Ser
VARIANT               11
                      note = Val
source                1..14
                      mol_type = protein
                      organism = synthetic construct
SEQUENCE: 6
GRGQGGYGQG AGGN                                                    14

SEQ ID NO: 7          moltype = AA  length = 18
FEATURE               Location/Qualifiers
REGION                1..18
                      note = Consensus sequence
source                1..18
                      mol_type = protein
                      organism = synthetic construct
SEQUENCE: 7
ASASAAASAA STVANSVS                                                18

SEQ ID NO: 8          moltype = AA  length = 8
FEATURE               Location/Qualifiers
REGION                1..8
                      note = Consensus sequence
```

-continued

```
source                  1..8
                        mol_type = protein
                        organism = synthetic construct
SEQUENCE: 8
ASAASAAA                                                                    8

SEQ ID NO: 9            moltype = AA  length = 8
FEATURE                 Location/Qualifiers
REGION                  1..8
                        note = Consensus sequence
source                  1..8
                        mol_type = protein
                        organism = synthetic construct
SEQUENCE: 9
GSAMGQGS                                                                    8

SEQ ID NO: 10           moltype = AA  length = 5
FEATURE                 Location/Qualifiers
REGION                  1..5
                        note = Consensus sequence
source                  1..5
                        mol_type = protein
                        organism = synthetic construct
SEQUENCE: 10
SASAG                                                                       5

SEQ ID NO: 11           moltype = AA  length = 346
FEATURE                 Location/Qualifiers
REGION                  1..346
                        note = Chimeric protein
source                  1..346
                        mol_type = protein
                        organism = synthetic construct
SEQUENCE: 11
MGHHHHHHMS HTTPWTNPGL AENFMNSFMQ GLSSMPGFTA SQLDDMSTIA QSMVQSIQSL  60
AAQGRTSPNK LQALNMAFAS SMAEIAASEE GGGSLSTKTS SIASAMSNAF LQTTGVVNQP  120
FINEITQLVS MFAQAGMNDV SAGNSGRGQG GYGQGSGGNA AAAAAAAAAA AAAAGQGGQG  180
GYGRQSQGAG SAAAAAAAAA AAAAAGSGQG GYGQGQGGGY GQGGNSVTSG GYGYGTSAAA  240
GAGVAAGSYA GAVNRLSSAE AASRVSSNIA AIASGGASAL PSVISNIYSG VVASGVSSNE  300
ALIQALLELL SALVHVLSSA SIGNVSSVGV DSTLNVVQDS VGQYVG             346

SEQ ID NO: 12           moltype = DNA  length = 1052
FEATURE                 Location/Qualifiers
misc_feature            1..1052
                        note = Chimeric construct
source                  1..1052
                        mol_type = other DNA
                        organism = synthetic construct
SEQUENCE: 12
ccatgggcca tcatcatcat catcatatga gccataccac cccgtggacc aacccgggcc  60
tggcggaaaa ctttatgaac agctttatgc agggcctgag cagcatgccg ggctttaccg  120
cgagccagct ggatgatatg agcaccattg cgcagagcat ggtgcagagc attcagagcc  180
tggcggcgca gggccgtacc agcccgaaca aactgcaggc gctgaacatg gcgtttgcga  240
gcagcatggc ggaaattgcg gcgagcgaag aaggcggcgg cagcctgagc accaaaacca  300
gcagcattgc gagcgcgatg agcaacgcgt ttctgcagac caccggcgtg gtgaaccagc  360
cgtttattaa cgaaattacc cagctggtga gcatgtttgc gcaggcgggc atgaacgatg  420
tgagcgcggg gaattcggga cgaggtcaag gaggatatgg tcaaggttct ggaggtaatg  480
ctgctgccgc agccgctgcc gccgccgccg ccgctgcagc agccggacag ggaggtcaag  540
gtggatatgg tagacaaagc caaggtgctg gttccgctgc tgctgctgct gctgctgctg  600
ccgctgctgc tgctgccagga tctggacaag gtggatacgg tggacaaggt caaggaggtt  660
atggtcagag tgggaattcg gttacatctg gaggttacgg atatggaacc agtgcagctg  720
caggagctgg agttgcagca ggttcatatg caggtgctgt caatcgcttg tctagtgctg  780
aagctgccag tagagtatcc tctaatattg cagctattgc atctggtggt gcttccgccc  840
tccccagtgt tatttcaaat atttactcag gtgtcgttgc ttctggtgtt tcttctaatg  900
aagctctgat tcaagctctg ttggaactcc tttccgcact tgttcatgtt ttaagcagtg  960
cctctatcgg taatgttagc tcagtaggag tagatagtac attgaatgtt gttcaggatt  1020
cagtaggcca atatgtaggt taatgaaagc tt                                 1052

SEQ ID NO: 13           moltype = DNA  length = 848
FEATURE                 Location/Qualifiers
misc_feature            1..848
                        note = Chimeric construct
source                  1..848
                        mol_type = other DNA
                        organism = synthetic construct
SEQUENCE: 13
ccatgggcca tcatcatcat catcatatgg ggaattcgat gcagtacaaa ctgatcatcg  60
acggtaaaac cctgaaaggt gaaaccacca ccgaagctgt tgacgctgct gctgctgaaa  120
aattcttcaa acagtacgct aacgacgacg gtatcgacgg tgaatggacc tacgacgacg  180
```

-continued

```
ctaccaaaac cttcaccgtt accgaattag tacctagagg atcagggaat tcgggacgag  240
gtcaaggagg atatggtcaa ggttctggag gtaatgctgc tgccgcagcc gctgccgccg  300
ccgccgccgc tgcagcagcc ggacaggag gtcaaggtgg atatggtaga caaagccaag  360
gtgctggttc cgctgctgct gctgctgctg ctgctgccgc tgctgctgct gcaggatctg  420
gacaaggtgg atacggtgga caaggtcaag gaggttatgg tcagagtggg accggtgtta  480
catctggagg ttacggatat ggaaccagtg cagctgcagg agctggagtt gcagcaggta  540
gttacgcagg tgctgtcaat cgcttgtcta gtgctgaagc tgccagtaga gtatcctcta  600
atattgcagc tattgcatct ggtggtgctt ccgccctccc cagtgttatt tcaaatattt  660
actcaggtgt cgttgcttct ggtgtttctt ctaatgaagc tctgattcaa gctctgttgg  720
aactcctttc cgcacttgtt catgttttaa gcagtgcctc tatcggtaat gttagctcag  780
taggagtaga tagtacattg aatgttgttc aggattcagt aggccaatat gtaggttaat  840
gaaagctt                                                            848

SEQ ID NO: 14            moltype = AA   length = 278
FEATURE                  Location/Qualifiers
REGION                   1..278
                         note = Chimeric protein
source                   1..278
                         mol_type = protein
                         organism = synthetic construct
SEQUENCE: 14
MGHHHHHMG NSMQYKLIID GKTLKGETTT EAVDAAAAEK FFKQYANDDG IDGEWTYDDA   60
TKTFTVTELV PRGSGNSGRG QGGYGQSGG NAAAAAAAAA AAAAAAGQGG QGGYGRQSQG   120
AGSAAAAAAA AAAAAAAGSG QGGYGGQGQG GYGQSGTGVT SGGYGYGTSA AAGAGVAAGS   180
YAGAVNRLSS AEAASRVSSN IAAIASGGAS ALPSVISNIY SGVVASGVSS NEALIQALLE   240
LLSALVHVLS SASIGNVSSV GVDSTLNVVQ DSVGQYVG                          278

SEQ ID NO: 15            moltype = AA   length = 108
FEATURE                  Location/Qualifiers
source                   1..108
                         mol_type = protein
                         organism = Araneus ventricosus
SEQUENCE: 15
AAGAGVAAGS YAGAVNRLSS AEAASRVSSN IAAIASGGAS ALPSVISNIY SGVVASGVSS   60
NEALIQALLE LLSALVHVLS SASIGNVSSV GVDSTLNVVQ DSVGQYVG                108

SEQ ID NO: 16            moltype = AA   length = 98
FEATURE                  Location/Qualifiers
source                   1..98
                         mol_type = protein
                         organism = Euprosthenops australis
SEQUENCE: 16
SRLSSPSAVS RVSSAVSSLV SNGQVNMAAL PNIISNISSS VSASAPGASG CEVIVQALLE   60
VITALVQIVS SSSVGYINPS AVNQITNVVA NAMAQVMG                          98

SEQ ID NO: 17            moltype = DNA   length = 1296
FEATURE                  Location/Qualifiers
misc_feature             1..1296
                         note = Chimeric construct
source                   1..1296
                         mol_type = other DNA
                         organism = synthetic construct
SEQUENCE: 17
cccatgggcc atcatcatca tcatcatatg agccatacca ccccgtggac caacccgggc   60
ctggcggaaa actttatgaa cagctttatg cagggcctga gcagcatgc gggctttacc   120
gcgagccagc tggatgatat gagcaccatt gcgcagagca tggtgcagag cattcagagc   180
ctggcggcgc agggccgtac cagcccgaac aaactgcagg cgctgaacat ggcgtttgcg   240
agcagcatgc cggaaattgc ggcgagcgaa gaaggcggcg gcagcctgag caccaaaacc   300
agcagcattg cgagcgcgat gagcaacgcg tttctgcaga ccaccggcgt ggtgaaccag   360
ccgtttatta acgaaattac ccagctggtg agcatgtttg cgcaggcggg catgaacgat   420
gtgagcgcgg ggaattcggg acgaggtcaa ggaggatatg gtcaaggttc tggaggtaat   480
gctgctgccg cagccgctgc cgccgccgcc gccgctgcag cagccggaca gggaggtcaa   540
ggtggatatg gtagacaaag ccaaggtgct ggttccgctg ctgctgctgc tgctgctgct   600
gccgctgctg ctgctgcagg atctggacaa ggtggat acggtggaca aggtcaagga   660
tatggtcaga gtgggaattc gggacgaggt caaggaggat atggtcaagg ttctggaggt   720
aatgctgctg ccgcagccgc tgccgccgcc gccgccgctg cagcagccgg acagggaggt   780
caaggtggat atggtagaca aagccaaggt gctggttccg ctgctgctgc tgctgctgct   840
gctgccgctg ctgctgctgc aggatctgga caaggtggat acggtggaca aggtcaagga   900
ggttatggtc agagtgggaa ttcggttaca tctggaggt acggatatgg aaccagtgca   960
gctgcaggag ctggagttgc agcaggttca tatgcaggtg ctgtcaatcg cttgtctagt   1020
gctgaagctg ccagtagagt atcctctaat attgcagcta ttgcatctgg tggtgcttcc   1080
gccctcccca gtgttatttc aaatatttac tcaggtgtcg ttgcttctgg tgtttcttct   1140
aatgaagctc tgattcaagc tctgttggaa ctcctttccg cacttgttca tgttttaagc   1200
agtgcctcta tcggtaatgt tagctcagta ggagtagata gtacattgaa tgttgttcag   1260
gattcagtag gccaatatgt aggttaatga aagctt                             1296

SEQ ID NO: 18            moltype = AA   length = 427
FEATURE                  Location/Qualifiers
REGION                   1..427
```

```
                                    note = Chimeric sequence
source                              1..427
                                    mol_type = protein
                                    organism = synthetic construct
SEQUENCE: 18
MGHHHHHHMS HTTPWTNPGL AENFMNSFMQ GLSSMPGFTA SQLDDMSTIA QSMVQSIQSL   60
AAQGRTSPNK LQALNMAFAS SMAEIAASEE GGGSLSTKTS SIASAMSNAF LQTTGVVNQP   120
FINEITQLVS MFAQAGMNDV SAGNSGRGQG GYGQGSGGNA AAAAAAAAAA AAAAGQGGQG   180
GYGRQSQGAG SAAAAAAAAA AAAAAGSGQG GYGQGGQGGY GQSGNSGRGQ GGYGQGSGGN   240
AAAAAAAAAA AAAAAGQGGQ GGYGRQSQGA GSAAAAAAAA AAAAAAGSGQ GGYGGQGQGG   300
YGQSGNSVTS GGYGYGTSAA AGAGVAAGSY AGAVNRLSSA EAASRVSSNI AAIASGGASA   360
LPSVISNIYS GVVASGVSSN EALIQALLEL LSALVHVLSS ASIGNVSSVG VDSTLNVVQD   420
SVGQYVG                                                            427

SEQ ID NO: 19        moltype = AA  length = 97
FEATURE              Location/Qualifiers
source               1..97
                     mol_type = protein
                     organism = Parawixia bistriata
SEQUENCE: 19
GAGAAAASGA TGRVANSLGA MASGGINALP GVFSNIFSQV SAASGGASGG AVLVQALTEV   60
IALLLHILSS ASIGNVSSQG LEGSMAIAQQ AIGAYAG                            97

SEQ ID NO: 20        moltype = AA  length = 88
FEATURE              Location/Qualifiers
source               1..88
                     mol_type = protein
                     organism = Tetragnatha kauaiensis
SEQUENCE: 20
SLLSSPASNA RISSAVSALA SGAASGPGYL SSVISNVVSQ VSSNSGGLVG CDTLVQALLE   60
AAAALVHVLA SSSGGQVNLN TAGYTSQL                                      88

SEQ ID NO: 21        moltype = AA  length = 93
FEATURE              Location/Qualifiers
source               1..93
                     mol_type = protein
                     organism = Argiope trifasciata
SEQUENCE: 21
AAASRLSSPQ ASSRVSSAVS TLVSSGPTNP ASLSNAISSV VSQVSASNPG LSGCDVLVQA   60
LLEIVSALVH ILGSSSIGQI NYAASSQYAQ MVG                                93

SEQ ID NO: 22        moltype = AA  length = 101
FEATURE              Location/Qualifiers
source               1..101
                     mol_type = protein
                     organism = Nephila clavipes
SEQUENCE: 22
SAASRLSSPE ASSRVSSAVS NLVSSGPTNS AALSSTISNV VSQIGASNPG LSGCDVLVQA   60
LLEVVSALIH ILGSSSIGQV NYGSAGQATQ IVGQSIYQAL G                       101

SEQ ID NO: 23        moltype = AA  length = 101
FEATURE              Location/Qualifiers
source               1..101
                     mol_type = protein
                     organism = Nephila clavipes
SEQUENCE: 23
AAASRLSSPQ ASSRVSSAVS NLVASGPTNS AALSSTISNV VSQIGASNPG LSGCDVLIQA   60
LLEVVSALIH ILGSSSIGQV NYGSAGQATQ IVGQSVYQAL G                       101

SEQ ID NO: 24        moltype = AA  length = 101
FEATURE              Location/Qualifiers
source               1..101
                     mol_type = protein
                     organism = Latrodectus Hesperus
SEQUENCE: 24
AAASALAAPA TSARISSHAS ALLSNGPTNP ASISNVISNA VSQISSSNPG ASACDVLVQA   60
LLELVTALLT IIGSSNIGSV NYDSSGQYAQ VVTQSVQNAF A                       101

SEQ ID NO: 25        moltype = AA  length = 101
FEATURE              Location/Qualifiers
source               1..101
                     mol_type = protein
                     organism = Latrodectus Hesperus
SEQUENCE: 25
SAASALSSPT THARISSHAS TLLSSGPTNA AALSNVISNA VSQVSASNPG SSSCDVLVQA   60
LLEIITALIS ILDSSSVGQV NYGSSGQYAQ IVGQSMQQAM G                       101

SEQ ID NO: 26        moltype = AA  length = 101
FEATURE              Location/Qualifiers
```

```
source                       1..101
                             mol_type = protein
                             organism = Latrodectus geometricus
SEQUENCE: 26
PAASALAAPA TSARISSHAL TLLSNGPTNP ASISNVISNA VSQISSSNPG YSSCDILVQA    60
LLELVTALLT IIGSSNVNDI NYGSSGQYAQ MVSQSVQNVF G                       101

SEQ ID NO: 27                moltype = AA  length = 101
FEATURE                      Location/Qualifiers
source                       1..101
                             mol_type = protein
                             organism = Euprosthenops australis
SEQUENCE: 27
NSVSRLSSPS AVSRVSSAVS SLVSNGQVNM AALPNIISNI SSSVSASAPG ASGCEVIVQA    60
LLEVITALVQ IVSSSSVGYI NPSAVNQITN VVANAMAQVM G                       101

SEQ ID NO: 28                moltype = AA  length = 98
FEATURE                      Location/Qualifiers
source                       1..98
                             mol_type = protein
                             organism = Nephila clavipes
SEQUENCE: 28
PGSPGGAYYP SSRVPDMVNG IMSAMQGSGF NYQMFGNMLS QYSSGSGTCN PNNVNVLMDA    60
LLAALHCLSN HGSSSFAPSP TPAAMSAYSN SVGRMFAY                           98

SEQ ID NO: 29                moltype = AA  length = 98
FEATURE                      Location/Qualifiers
source                       1..98
                             mol_type = protein
                             organism = Nephila inaurata madagascariensis
SEQUENCE: 29
GPGSGGSYYP SSRVPDMVNG IMSAMQGSGF NYQMFGNMLS QYSSGSGSCN PNNVNVLMDA    60
LLAALHCLSN HGSSSFAPSP TPAAMSAYSN SVGRMFAY                           98

SEQ ID NO: 30                moltype = AA  length = 93
FEATURE                      Location/Qualifiers
source                       1..93
                             mol_type = protein
                             organism = Latrodectus geometricus
SEQUENCE: 30
SAASALSSPT THARISSHAS TLLSSGPTNS AAISNVISNA VSQVSASNPG SSSCDVLVQA    60
LLELITALIS IVDSSNIGQV NYGSSGQYAQ MVG                                93

SEQ ID NO: 31                moltype = AA  length = 101
FEATURE                      Location/Qualifiers
source                       1..101
                             mol_type = protein
                             organism = Latrodectus geometricus
SEQUENCE: 31
AAASALAAPA TSARISSHAS TLLSNGPTNP ASISNVISNA VSQISSSNPG ASSCDVLVQA    60
LLELVTALLT IIGSSNVGNV NYDSSGQYAQ VVSQSVQNAF V                       101

SEQ ID NO: 32                moltype = AA  length = 96
FEATURE                      Location/Qualifiers
source                       1..96
                             mol_type = protein
                             organism = Araneus diadematus
SEQUENCE: 32
GAVNRLSSAG AASRVSSNVA AIASAGAAAL PNVISNIYSG VLSSGVSSSE ALIQALLEVI    60
SALIHVLGSA SIGNVSSVGV NSALNAVQNA VGAYAG                             96

SEQ ID NO: 33                moltype = AA  length = 99
FEATURE                      Location/Qualifiers
source                       1..99
                             mol_type = protein
                             organism = Argiope trifasciata
SEQUENCE: 33
SRLSSPGAAS RVSSAVTSLV SSGGPTNSAA LSNTISNVVS QISSSNPGLS GCDVLVQALL    60
EIVSALVHIL GSANIGQVNS SGVGRSASIV GQSINQAFS                          99

SEQ ID NO: 34                moltype = AA  length = 89
FEATURE                      Location/Qualifiers
source                       1..89
                             mol_type = protein
                             organism = Cyrtophora moluccensis
SEQUENCE: 34
SHLSSPEASS RVSSAVSNLV SSGSTNSAAL PNTISNVVSQ ISSSNPGLSG CDVLVQALLE    60
VVSALIHILG SSSIGQVNYG SAGQATQIV                                     89
```

-continued

```
SEQ ID NO: 35            moltype = AA   length = 87
FEATURE                  Location/Qualifiers
source                   1..87
                         mol_type = protein
                         organism = Nephila inaurata madagascariensis
SEQUENCE: 35
SRLSSPQASS RVSSAVSNLV ASGPTNSAAL SSTISNAVSQ IGASNPGLSG CDVLIQALLE   60
VVSALIHILG SSSIGQVNYG SAGQATQ                                        87

SEQ ID NO: 36            moltype = AA   length = 97
FEATURE                  Location/Qualifiers
source                   1..97
                         mol_type = protein
                         organism = Argiope amoena
SEQUENCE: 36
RLSSPQASSR VSSAVSTLVS SGPTNPASLS NAIGSVVSQV SASNPGLPSC DVLVQALLEI   60
VSALVHILGS SSIGQINYSA SSQYARLVGQ SIAQALG                             97

SEQ ID NO: 37            moltype = AA   length = 82
FEATURE                  Location/Qualifiers
source                   1..82
                         mol_type = protein
                         organism = Argiope aurantia
SEQUENCE: 37
SRLSSPQASS RVSSAVSTLV SSGPTNPAAL SNAISSVVSQ VSASNPGLSG CDVLVQALLE   60
LVSALVHILG SSSIGQINYA AS                                             82

SEQ ID NO: 38            moltype = AA   length = 98
FEATURE                  Location/Qualifiers
source                   1..98
                         mol_type = protein
                         organism = Argiope trifasciata
SEQUENCE: 38
SRLSSPQASS RVSSAVSTLV SSGPTNPASL SNAISSVVSQ VSSSNPGLSG CDVLVQALLE   60
IVSALVHILG SSSIGQINYA ASSQYAQLVG QSLTQALG                            98

SEQ ID NO: 39            moltype = AA   length = 89
FEATURE                  Location/Qualifiers
source                   1..89
                         mol_type = protein
                         organism = Gasteracantha mammosa
SEQUENCE: 39
SRLSSPQAGA RVSSAVSALV ASGPTSPAAV SSAISNVASQ ISASNPGLSG CDVLVQALLE   60
IVSALVSILS SASIGQINYG ASGQYAAMI                                      89

SEQ ID NO: 40            moltype = AA   length = 98
FEATURE                  Location/Qualifiers
source                   1..98
                         mol_type = protein
                         organism = Araneus diadematus
SEQUENCE: 40
SRLSSPSAAA RVSSAVSLVS NGGPTSPAAL SSSISNVVSQ ISASNPGLSG CDILVQALLE   60
IISALVHILG SANIGPVNSS SAGQSASIVG QSVYRALS                            98

SEQ ID NO: 41            moltype = AA   length = 98
FEATURE                  Location/Qualifiers
source                   1..98
                         mol_type = protein
                         organism = Araneus diadematus
SEQUENCE: 41
SRLSSPAASS RVSSAVSSLV SSGPTKHAAL SNTISSVVSQ VSASNPGLSG CDVLVQALLE   60
VVSALVSILG SSSIGQINYG ASAQYTQMVG QSVAQALA                            98

SEQ ID NO: 42            moltype = AA   length = 100
FEATURE                  Location/Qualifiers
source                   1..100
                         mol_type = protein
                         organism = Deinopis spinosa
SEQUENCE: 42
SAVSRMSTPG SGSRISNAVS NILSSGVSSS SGLSNAISNI SSSISASNPG LSGCDVLVQV   60
LLEVISALVH ILGSASVGQV GSSPQNAQMV AANAVANAFS                         100

SEQ ID NO: 43            moltype = AA   length = 100
FEATURE                  Location/Qualifiers
source                   1..100
                         mol_type = protein
                         organism = Deinopis spinosa
SEQUENCE: 43
SAVSRMSTPG SGSRISNAVS NILSSGVSSS SGLSNVISNL SSSISTSNPG LSGCDVLVQV   60
```

-continued

```
LLEVISALVH ILSSASLGQV GSSPQNAQMV AANAVANAFS                          100

SEQ ID NO: 44          moltype = AA   length = 96
FEATURE                Location/Qualifiers
source                 1..96
                       mol_type = protein
                       organism = Metepeira grandiosa
SEQUENCE: 44
GAVNRLSSAE AASRVSSNVA ALASGGPAAL ANVMGNIYSG VASSGVSSGE ALVQALLEVI    60
SALVHLLSNA SIGNVSSAGL GNTMSLVQST VGAYAG                              96

SEQ ID NO: 45          moltype = AA   length = 101
FEATURE                Location/Qualifiers
source                 1..101
                       mol_type = protein
                       organism = Latrodectus hesperus
SEQUENCE: 45
SAASRLSSPS SSSRISSAAS SLATGGVLNS AALPSVVSNM MSQVSASSPG MSSSEVVIQA    60
LLELVSSLIH ILSSANIGQV DFNSVGNTAA VVGQSLGAAL G                        101

SEQ ID NO: 46          moltype = AA   length = 100
FEATURE                Location/Qualifiers
source                 1..100
                       mol_type = protein
                       organism = Nephila clavipes
SEQUENCE: 46
AAASRLASPD SGARVASAVS NLVSSGPTSS AALSSVISNA VSQIGASNPG LSGCDVLIQA    60
LLEIVSACVT ILSSSSIGQV NYGAASQFAQ VVGQSVLSAF                          100

SEQ ID NO: 47          moltype = AA   length = 85
FEATURE                Location/Qualifiers
source                 1..85
                       mol_type = protein
                       organism = Nephila inaurata madagascariensis
SEQUENCE: 47
AAASRLASPD SGARVASAVS NLVSSGPTSS AALSSVISNA VSQIGASNPG LSGCDVLIQA    60
LLEIVSACVT ILSSSSIGQV NYGAA                                         85

SEQ ID NO: 48          moltype = AA   length = 101
FEATURE                Location/Qualifiers
source                 1..101
                       mol_type = protein
                       organism = Latrodectus hesperus
SEQUENCE: 48
SAASRLSSPS SSSRISSAAS SLATGGVLNS AALPSVVSNI MSQVSASSPG MSSSEVVIQA    60
LLELVSSLIH ILSSANIGQV DFNSVGNTAA VVGQSLGAAL G                        101

SEQ ID NO: 49          moltype = AA   length = 100
FEATURE                Location/Qualifiers
REGION                 1..100
                       note = Consensus sequence
source                 1..100
                       mol_type = protein
                       organism = synthetic construct
SEQUENCE: 49
SRLSSPQASS RVSSAVSNLV SSGPTNSAAL SNTISNVVSQ ISASNPGLSG CDVLVQALLE    60
VVSALVHILG SSSIGQVNYG SAGQATQIVG QSVAQALGEF                          100

SEQ ID NO: 50          moltype = AA   length = 93
FEATURE                Location/Qualifiers
source                 1..93
                       mol_type = protein
                       organism = Macrothele holsti
SEQUENCE: 50
SHLSSPEASS RVSSAVSNLV SGGSTNSAAL PNTISNVVSQ ISSSNPGLSG CDVLVQALLE    60
VVSALIHILG SSSIGQVDYG SAGQATQIVG QSA                                 93

SEQ ID NO: 51          moltype = AA   length = 89
FEATURE                Location/Qualifiers
source                 1..89
                       mol_type = protein
                       organism = Nephila pilipes
SEQUENCE: 51
SRLSSPEASS RVSSAVSNLV SSGPTNSAAL SNTISNVVSQ ISSSNPGLSG CDVLVQALLE    60
VVSALIHILG SSSIGQVNYG SAGQATQIV                                      89

SEQ ID NO: 52          moltype = AA   length = 89
FEATURE                Location/Qualifiers
source                 1..89
```

-continued

```
                         mol_type = protein
                         organism = Octonoba varians
SEQUENCE: 52
SRLSSPEASS RVSSAVSNLV SSGPTNSAAL SNTISNVVSQ ISSSNPGLSG CDVLVQALLE    60
VVSAPIHILG SSSIGQVNYG SAGQATQIV                                      89

SEQ ID NO: 53           moltype = AA  length = 89
FEATURE                 Location/Qualifiers
source                  1..89
                        mol_type = protein
                        organism = Psechrus sinensis
SEQUENCE: 53
SRLSSPEASS RVSSAVSNLV SSGPTNSAAL PNTISNVVSQ ISSSNPGLSG CDVLVQALLE    60
VVSALIHILG SSSIGQVNYG SAGQATQIV                                      89

SEQ ID NO: 54           moltype = AA  length = 88
FEATURE                 Location/Qualifiers
source                  1..88
                        mol_type = protein
                        organism = Tetragnatha versicolor
SEQUENCE: 54
SRLSSPASNA RISSAVSALA SGGASSPGYL SSIISNVVSQ VSSNNDGLSG CDTVVQALLE    60
VAAALVHVLA SSNIGQVNLN TAGYTSQL                                       88

SEQ ID NO: 55           moltype = AA  length = 82
FEATURE                 Location/Qualifiers
SITE                    35
                        note = misc_feature - Xaa can be any naturally occurring
                         amino acid
SITE                    56
                        note = misc_feature - Xaa can be any naturally occurring
                         amino acid
source                  1..82
                        mol_type = protein
                        organism = Nephila senegalensis
SEQUENCE: 55
SRLASPDSGA RVASAVSNLV SSGPTSSAAL SSVIXNAVSQ IGASNPGLSG CDVLIXALLE    60
IVSACVTILS SSSIGQVNYG AA                                             82

SEQ ID NO: 56           moltype = AA  length = 94
FEATURE                 Location/Qualifiers
source                  1..94
                        mol_type = protein
                        organism = Araneus diadematus
SEQUENCE: 56
SVYLRLQPRL EVSSAVSSLV SSGPTNGAAV SGALNSLVSQ ISASNPGLSG CDALVQALLE    60
LVSALVAILS SASIGQVNVS SVSQSTQMIS QALS                                94

SEQ ID NO: 57           moltype = AA  length = 99
FEATURE                 Location/Qualifiers
source                  1..99
                        mol_type = protein
                        organism = Agelenopsis aperta
SEQUENCE: 57
NSVSRLSSPS SSSRVSSAVS GLLPNGNFNL GNLPGIVSNL SSSIASSGLS GCENLVQVLI    60
EVVSALVHIL GSANIGNINM NAASSTAAAV GQAIVNGLY                           99

SEQ ID NO: 58           moltype = AA  length = 102
FEATURE                 Location/Qualifiers
source                  1..102
                        mol_type = protein
                        organism = Argiope argentata
SEQUENCE: 58
ASSSGLGSSA ASARVSSLAN SVASAISSSG GSLSVPTFLN FLSSVGAQVS SSSSLNSSEV    60
TNEVLLEAIA ALLQVLNGAQ ITSVNLRNVP NAQQALVQAL SG                       102

SEQ ID NO: 59           moltype = AA  length = 100
FEATURE                 Location/Qualifiers
REGION                  1..100
                        note = Artificial construct
source                  1..100
                        mol_type = protein
                        organism = synthetic construct
SEQUENCE: 59
SRLSSPEASS RVSSAVSNLV SSGPTNSAAL SSTISNVVSQ IGASNPGLSG CDVLVQALLE    60
VVSALIHILG SSSIGQVNYG SAGQATQLVG QSVYQALGEF                          100

SEQ ID NO: 60           moltype = AA  length = 87
FEATURE                 Location/Qualifiers
```

-continued

```
source                  1..87
                        mol_type = protein
                        organism = Nephila senegalensis
SEQUENCE: 60
SRLSSPEASS RVSSAVSNLV SSGPTNSAAL SSTISNVVSQ IGASNPGLSG CDVLIQALLE  60
VVSALVHILG SSSIGQVNYG SAGQATQ                                      87

SEQ ID NO: 61           moltype = AA  length = 97
FEATURE                 Location/Qualifiers
source                  1..97
                        mol_type = protein
                        organism = Dolomedes tenebrosus
SEQUENCE: 61
SRLSSPQAAS RVSSAVSSLV SNGQVNVAAL PSIISSLSSS ISASSTAASD CEVLVQVLLE  60
IVSALVQIVS SANVGYINPE ASGSLNAVGS ALAAAMG                           97

SEQ ID NO: 62           moltype = AA  length = 100
FEATURE                 Location/Qualifiers
source                  1..100
                        mol_type = protein
                        organism = Uloborus diversus
SEQUENCE: 62
AASNRIVSAP AVNRMSAASS TLVSNGAFNV GALGSTISDM AAQIQAGSQG LSSAEATVQA  60
LLEVISVLTH MLSSANIGYV DFSRVGDSAS AVSQSMAYAG                        100

SEQ ID NO: 63           moltype = AA  length = 102
FEATURE                 Location/Qualifiers
source                  1..102
                        mol_type = protein
                        organism = Argiope bruennichi
SEQUENCE: 63
VSSSGLGSSA ATARVSSLAN SFASAISSSG GSLSVPTFLN LLSSVGAQVS SSSSLSSLEV  60
TNEVLLEAIA ALLQVINGGS ITSVDLRYVP NAQQDLVNAL SG                     102

SEQ ID NO: 64           moltype = AA  length = 96
FEATURE                 Location/Qualifiers
source                  1..96
                        mol_type = protein
                        organism = Araneus ventricosus
SEQUENCE: 64
GAVNRLSSAE AASRVSSNIA AIASGGASAL PSVISNIYSG VVASGVSSNE ALIQALLELL  60
SALVHVLSSA SIGNVSSVGV DSTLNVVQDS VGQYVG                            96

SEQ ID NO: 65           moltype = AA  length = 101
FEATURE                 Location/Qualifiers
source                  1..101
                        mol_type = protein
                        organism = Nephila clavipes
SEQUENCE: 65
STTSRLSSAE ASSRISSAAS TLVSGGYLNT AALPSVISDL FAQVGASSPG VSDSEVLIQV  60
LLEIVSSLIH ILSSSSVGQV DFSSVGSSAA AVGQSMQVVM G                      101

SEQ ID NO: 66           moltype = AA  length = 71
FEATURE                 Location/Qualifiers
source                  1..71
                        mol_type = protein
                        organism = Dolomedes tenebrosus
SEQUENCE: 66
SRLSSPEAAS RVSSAVSSLV SNGQVNVDAL PSIISNLSSS ISASATTASD CEVLVQVLLE  60
VVSALVQIVC S                                                       71

SEQ ID NO: 67           moltype = AA  length = 102
FEATURE                 Location/Qualifiers
source                  1..102
                        mol_type = protein
                        organism = Agelenopsis aperta
SEQUENCE: 67
SSETGLSSAS ASSRVNSLAS SVASAIASGQ ALSADSFAKS LLIQASQIQS SAPSFKADDV  60
VHESLLEGIS ALIQVINSSY GSPLSLSNAQ TVNAGLVNYF LV                     102

SEQ ID NO: 68           moltype = AA  length = 102
FEATURE                 Location/Qualifiers
source                  1..102
                        mol_type = protein
                        organism = Nephila clavata
SEQUENCE: 68
LSSSGLSSAS ASARVGSLAQ SLASALSTSR GTLSLSTFLN LLSPISSEIR ANTSLDGTQA  60
TVEALLEALA ALLQVINGAQ ITDVNVSSVP SVNAALASAL VA                     102
```

-continued

```
SEQ ID NO: 69               moltype = AA   length = 104
FEATURE                     Location/Qualifiers
source                      1..104
                            mol_type = protein
                            organism = Latrodectus hesperus
SEQUENCE: 69
LSPAGLASTA ATSRINDIAQ SLSSTLSSGS QLAPDNVLPG LIQLSSSIQS GNPDLDPAGV   60
LIESLLEYTS ALLALLQNAQ ITTYDAATLP AFNTALVNYL VPLV                    104

SEQ ID NO: 70               moltype = AA   length = 95
FEATURE                     Location/Qualifiers
source                      1..95
                            mol_type = protein
                            organism = Argiope argentata
SEQUENCE: 70
SVSRLSSAEA VSRVSSNIGA IASGGASALP GVISNIFSGV SASAGSYEEA VIQSLLEVLS   60
ALLHILSNSS IGYVGADGLT DSLAVVQQAM GPVVG                              95

SEQ ID NO: 71               moltype = AA   length = 101
FEATURE                     Location/Qualifiers
source                      1..101
                            mol_type = protein
                            organism = Nephila antipodiana
SEQUENCE: 71
STTSRLSTAE ASSRISTAAS TLVSGGYLNT AALPSVIADL FAQVGASSPG VSDSEVLIQV   60
LLEIVSSLIH ILSSSSVGQV DFSSVGSSAA AVGQSMQVVM G                       101

SEQ ID NO: 72               moltype = AA   length = 100
FEATURE                     Location/Qualifiers
source                      1..100
                            mol_type = protein
                            organism = Nephila clavipes
SEQUENCE: 72
STTSRLSSAE ACSRISAAAS TLVSGSLNTA ALPSVISDLF AQVSASSPGV SGNEVLIQVL   60
LEIVSSLIHI LSSSSVGQVD FSSVGSSAAA VGQSMQVVMG                         100

SEQ ID NO: 73               moltype = AA   length = 103
FEATURE                     Location/Qualifiers
source                      1..103
                            mol_type = protein
                            organism = Deinopis spinosa
SEQUENCE: 73
ASTSRLASGQ ATDRVKDVVS TLVSNGINGD ALSNAISNVM TQVNAAVPGL SFCERLIQVL   60
LEIVAALVHI LSSSNVGSID YGSTSRTAIG VSNALASAVA GAF                     103

SEQ ID NO: 74               moltype = AA   length = 352
FEATURE                     Location/Qualifiers
REGION                      1..352
                            note = Artificial construct
source                      1..352
                            mol_type = protein
                            organism = synthetic construct
SEQUENCE: 74
MGHHHHHMS HTTPWTNPGL AENFMNSFMQ GLSSMPGFTA SQLDDMSTIA QSMVQSIQSL    60
AAQGRTSPNK LQALNMAFAS SMAEIAASEE GGGSLSTKTS SIASAMSNAF LQTTGVVNQP   120
FINEITQLVS MFAQAGMNDV SAGNSGRGQG GYGQGSGGNA AAAAAAAAA AAAAGQGGQG    180
GYGRQSQGAG SAAAAAAAA AAAAAGSGQG GYGQGQGGY GQSGSVTSGG YGYGTSAAAG     240
AGVAAGSYAA STSRLASGQA TDRVKDVVST LVSNGINGDA LSNAISNVMT QVNAAVPGLS   300
FCERLIQVLL EIVAALVHIL SSSNVGSIDY GSTSRTAIGV SNALASAVAG AF           352

SEQ ID NO: 75               moltype = AA   length = 350
FEATURE                     Location/Qualifiers
REGION                      1..350
                            note = Artificial construct
source                      1..350
                            mol_type = protein
                            organism = synthetic construct
SEQUENCE: 75
MGHHHHHHMS HTTPWTNPGL AENFMNSFMQ GLSSMPGFTA SQLDDMSTIA QSMVQSIQSL   60
AAQGRTSPNK LQALNMAFAS SMAEIAASEE GGGSLSTKTS SIASAMSNAF LQTTGVVNQP   120
FINEITQLVS MFAQAGMNDV SAGNSGRGQG GYGQGSGGNA AAAAAAAAA AAAAGQGGQG    180
GYGRQSQGAG SAAAAAAAA AAAAAGSGQG GYGQGQGGY GQSGSVTSGG YGYGTSAAAG     240
AGVAAGSYAN SVSRLSSPSA VSRVSSAVSS LVSNGQVNMA ALPNIISNIS SSVSASAPGA   300
SGCEVIVQAL LEVITALVQI VSSSSVGYIN PSAVNQITNV VANAMAQVMG              350

SEQ ID NO: 76               moltype = AA   length = 343
FEATURE                     Location/Qualifiers
REGION                      1..343
                            note = Artificial construct
```

-continued

```
source                  1..343
                        mol_type = protein
                        organism = synthetic construct
SEQUENCE: 76
MGHHHHHHMS HTTPWTNPGL AENFMNSFMQ GLSSMPGFTA SQLDDMSTIA QSMVQSIQSL   60
AAQGRTSPNK LQALNMAFAS SMAEIAASEE GGGSLSTKTS SIASAMSNAF LQTTGVVNQP  120
FINEITQLVS MFAQAGMNDV SAGNSGRGQG GYGQGSGGNA AAAAAAAAA AAAAGQGGQG   180
GYGRQSQGAG SAAAAAAAAA AAAAAGSGQG GYGGQGQGGY GQSGSVTSGG YGYGTSAAAG   240
AGVAAGSYAS VYLRLQPRLE VSSAVSSLVS SGPTNGAAVS GALNSLVSQI SASNPGLSGC   300
DALVQALLEL VSALVAILSS ASIGQVNVSS VSQSTQMISQ ALS                    343

SEQ ID NO: 77           moltype = AA  length = 350
FEATURE                 Location/Qualifiers
REGION                  1..350
                        note = Artificial construct
source                  1..350
                        mol_type = protein
                        organism = synthetic construct
SEQUENCE: 77
MGHHHHHHMS HTTPWTNPGL AENFMNSFMQ GLSSMPGFTA SQLDDMSTIA QSMVQSIQSL   60
AAQGRTSPNK LQALNMAFAS SMAEIAASEE GGGSLSTKTS SIASAMSNAF LQTTGVVNQP  120
FINEITQLVS MFAQAGMNDV SAGNSGRGQG GYGQGSGGNA AAAAAAAAA AAAAGQGGQG   180
GYGRQSQGAG SAAAAAAAAA AAAAAGSGQG GYGGQGQGGY GQSGSVTSGG YGYGTSAAAG   240
AGVAAGSYAS AASRLSSPSS SSRISSAASS LATGGVLNSA ALPSVVSNMM SQVSASSPGM   300
SSSEVVIQAL LELVSSLIHI LSSANIGQVD FNSVGNTAAV VGQSLGAALG             350

SEQ ID NO: 78           moltype = AA  length = 346
FEATURE                 Location/Qualifiers
REGION                  1..346
                        note = Artificial construct
source                  1..346
                        mol_type = protein
                        organism = synthetic construct
SEQUENCE: 78
MGHHHHHHMS HTTPWTNPGL AENFMNSFMQ GLSSMPGFTA SQLDDMSTIA QSMVQSIQSL   60
AAQGRTSPNK LQALNMAFAS SMAEIAASEE GGGSLSTKTS SIASAMSNAF LQTTGVVNQP  120
FINEITQLVS MFAQAGMNDV SAGNSGRGQG GYGQGSGGNA AAAAAAAAA AAAAGQGGQG   180
GYGRQSQGAG SAAAAAAAAA AAAAAGSGQG GYGGQGQGGY GQSGNSVTSG GYGYGTSAAA   240
GAGVAAGSYA GAVNRLSSAE AASAVSSNIA AIASGGASAL PSVISNIYSG VVASGVSSNE   300
ALIQALLELL SALVHVLSSA SIGNVSSVGV DSTLNVVQDS VGQYVG                 346

SEQ ID NO: 79           moltype = AA  length = 346
FEATURE                 Location/Qualifiers
REGION                  1..346
                        note = Artificial construct
source                  1..346
                        mol_type = protein
                        organism = synthetic construct
SEQUENCE: 79
MGHHHHHHMS HTTPWTNPGL AENFMNSFMQ GLSSMPGFTA SQLDDMSTIA QSMVQSIQSL   60
AAQGRTSPNK LQALNMAFAS SMAEIAASEE GGGSLSTKTS SIASAMSNAF LQTTGVVNQP  120
FINEITQLVS MFAQAGMNDV SAGNSGRGQG GYGQGSGGNA AAAAAAAAA AAAAGQGGQG   180
GYGRQSQGAG SAAAAAAAAA AAAAAGSGQG GYGGQGQGGY GQSGNSVTSG GYGYGTSAAA   240
GAGVAAGSYA GAVNRLSSAE AASRVSSNIA AIASGGASAL PSVISNIYSG VVASGVSSNE   300
ALIQALLELL SALVHVLSSA SIGNVSSVGV ASTLNVVQDS VGQYVG                 346

SEQ ID NO: 80           moltype = AA  length = 131
FEATURE                 Location/Qualifiers
source                  1..131
                        mol_type = protein
                        organism = Euprosthenops australis
SEQUENCE: 80
SHTTPWTNPG LAENFMNSFM QGLSSMPGFT ASQLDDMSTI AQSMVQSIQS LAAQGRTSPN   60
KLQALNMAFA SSMAEIAASE EGGGSLSTKT SSIASAMSNA FLQTTGVVNQ PFINEITQLV  120
SMFAQAGMND V                                                       131

SEQ ID NO: 81           moltype = AA  length = 127
FEATURE                 Location/Qualifiers
source                  1..127
                        mol_type = protein
                        organism = Latrodectus geometricus
SEQUENCE: 81
QANTPWSSKQ NADAFISAFM TAASQSGAFS SDQIDDMSVI SNTLMAAMDN MGGRITPSKL   60
QALDMAFASS VAEIAAVEGQ NIGVTTNAIS DALTSAFYQT TGVVNNKFIS EIRSLINMFA  120
QASANDV                                                            127

SEQ ID NO: 82           moltype = AA  length = 127
FEATURE                 Location/Qualifiers
source                  1..127
```

-continued

```
                              mol_type = protein
                              organism = Latrodectus hesperus
SEQUENCE: 82
QANTPWSSKA NADAFINSFI SAASNTGSFS QDQMEDMSLI GNTLMAAMDN MGGRITPSKL  60
QALDMAFASS VAEIAASEGG DLGVTTNAIA DALTSAFYQT TGVVNSRFIS EIRSLIGMFA  120
QASANDV                                                           127

SEQ ID NO: 83          moltype = AA  length = 130
FEATURE                Location/Qualifiers
source                 1..130
                       mol_type = protein
                       organism = Nephila clavipes
SEQUENCE: 83
QNTPWSSTEL ADAFINAFMN EAGRTGAFTA DQLDDMSTIG DTIKTAMDKM ARSNKSSKGK  60
LQALNMAFAS SMAEIAAVEQ GGLSVDAKTN AIADSLNSAF YQTTGAANPQ FVNEIRSLIN  120
MFAQSSANEV                                                        130

SEQ ID NO: 84          moltype = AA  length = 131
FEATURE                Location/Qualifiers
source                 1..131
                       mol_type = protein
                       organism = Argiope trifasciata
SEQUENCE: 84
QGATPWENSQ LAESFISRFL RFIGQSGAFS PNQLDDMSSI GDTLKTAIEK MAQSRKSSKS  60
KLQALNMAFA SSMAEIAVAE QGGLSLEAKT NAIASALSAA FLETTGYVNQ QFVNEIKTLI  120
FMIAQASSNE I                                                      131

SEQ ID NO: 85          moltype = AA  length = 124
FEATURE                Location/Qualifiers
source                 1..124
                       mol_type = protein
                       organism = Latrodectus geometricus
SEQUENCE: 85
LRWSSKDNAD RFINAFLQAA SNSGAFSSDQ VDDMSVIGNT LMTAMDNMGG RITPSKLQAL  60
DMAFASSVAE IAVADGQNVG GATNAISNAL RSAFYQTTGV VNNQFISEIS NLINMFAQVS  120
ANEV                                                              124

SEQ ID NO: 86          moltype = AA  length = 127
FEATURE                Location/Qualifiers
source                 1..127
                       mol_type = protein
                       organism = Latrodectus hesperus
SEQUENCE: 86
QANTPWSSKE NADAFIGAFM NAASQSGAFS SDQIDDMSVI SNTLMAAMDN MGGRITQSKL  60
QALDMAFASS VAEIAVADGQ NVGAATNAIS DALRSAFYQT TGVVNNQFIT GISSLIGMFA  120
QVSGNEV                                                           127

SEQ ID NO: 87          moltype = AA  length = 131
FEATURE                Location/Qualifiers
source                 1..131
                       mol_type = protein
                       organism = Nephila inaurata madagascariensis
SEQUENCE: 87
QANTPWSDTA TADAFIQNFL GAVSGSGAFT PDQLDDMSTV GDTIMSAMDK MARSNKSSKS  60
KLQALNMAFA SSMAEIAAVE QGGQSMDVKT NAIANALDSA FYMTTGSTNQ QFVNEMRSLI  120
NMLSAAAVNE V                                                      131

SEQ ID NO: 88          moltype = AA  length = 131
FEATURE                Location/Qualifiers
source                 1..131
                       mol_type = protein
                       organism = Nephila clavipes
SEQUENCE: 88
QARSPWSDTA TADAFIQNFL AAVSGSGAFT SDQLDDMSTI GDTIMSAMDK MARSNKSSQH  60
KLQALNMAFA SSMAEIAAVE QGGMSMAVKT NAIVDGLNSA FYMTTGAANP QFVNEMRSLI  120
SMISAASANE V                                                      131

SEQ ID NO: 89          moltype = AA  length = 129
FEATURE                Location/Qualifiers
source                 1..129
                       mol_type = protein
                       organism = Argiope bruennichi
SEQUENCE: 89
AVPSVFSSPN LASGFLQCLT FGIGNSPAFP TQEQQDLDAI AQVILNAVSS NTGATASARA  60
QALSTALASS LTDLLIAESA ESNYSNQLSE LTGILSDCFI QTTGSDNPAF VSRIQSLISV  120
LSQNADTNI                                                         129

SEQ ID NO: 90          moltype = AA  length = 129
FEATURE                Location/Qualifiers
```

-continued

```
source                  1..129
                        mol_type = protein
                        organism = Nephila clavata
SEQUENCE: 90
PVPSVFSSPS LASGFLGCLT TGIGLSPAFP FQEQQDLDDL AKVILSAVTS NTDTSKSARA    60
QALSTALASS LADLLISESS GSSYQTQISA LTNILSDCFV TTTGSNNPAF VSRVQTLIGV   120
LSQSSSNAI                                                           129

SEQ ID NO: 91           moltype = AA  length = 128
FEATURE                 Location/Qualifiers
source                  1..128
                        mol_type = protein
                        organism = Latrodectus hesperus
SEQUENCE: 91
ASVNIFNSPN AATSFLNCLR SNIESSPAFP FQEQADLDSI AEVILSDVSS VNTASSATSL    60
ALSTALASSL AELLVTESAE EDIDNQVVAL STILSQCFVE TTGSPNPAFV ASVKSLLGVL   120
SQSASNYE                                                            128

SEQ ID NO: 92           moltype = AA  length = 130
FEATURE                 Location/Qualifiers
source                  1..130
                        mol_type = protein
                        organism = Nephila clavipes
SEQUENCE: 92
IANSPFSNPN TAEAFARSFV SNIVSSGEFG AQGAEDFDDI IQSLIQAQSM GKGRHDTKAK    60
AKAMQVALAS SIAELVIAES SGGDVQRKTN VISNALRNAL MSTTGSPNEE FVHEVQDLIQ   120
MLSQEQINEV                                                          130

SEQ ID NO: 93           moltype = AA  length = 130
FEATURE                 Location/Qualifiers
source                  1..130
                        mol_type = protein
                        organism = Nephila inaurata madagascariensis
SEQUENCE: 93
IVNSPFSNPN TAEAFARSFV SNVVSSGEFG AQGAEDFDDI IQSLIQAQSM GKGRHDTKAK    60
AKAMQVALAS SIAELVIAES SGGDVQRKTN VISNALRNAL MSTTGSPNEE FVHEVQDLIQ   120
MLSQEQINEV                                                          130

SEQ ID NO: 94           moltype = AA  length = 9
FEATURE                 Location/Qualifiers
REGION                  1..9
                        note = His tag
source                  1..9
                        mol_type = protein
                        organism = synthetic construct
SEQUENCE: 94
MGHHHHHHM                                                             9

SEQ ID NO: 95           moltype = AA  length = 133
FEATURE                 Location/Qualifiers
source                  1..133
                        mol_type = protein
                        organism = Euprosthenops australis
SEQUENCE: 95
SHTTPWTNPG LAENFMNSFM QGLSSMPGFT ASQLDDMSTI AQSMVQSIQS LAAQGRTSPN    60
KLQALNMAFA SSMAEIAASE EGGGSLSTKT SSIASAMSNA FLQTTGVVNQ PFINEITQLV   120
SMFAQAGMND VSA                                                      133

SEQ ID NO: 96           moltype = AA  length = 84
FEATURE                 Location/Qualifiers
source                  1..84
                        mol_type = protein
                        organism = Euprosthenops australis
SEQUENCE: 96
GNSGRGQGGY GQGSGGNAAA AAAAAAAAAA AAGQGGQGGY GRQSQGAGSA AAAAAAAAA    60
AAAGSGQGGY GGQGQGGYGQ SGNS                                           84

SEQ ID NO: 97           moltype = AA  length = 120
FEATURE                 Location/Qualifiers
REGION                  1..120
                        note = CT based on Araneus ventricosus
source                  1..120
                        mol_type = protein
                        organism = synthetic construct
SEQUENCE: 97
VTSGGYGYGT SAAAGAGVAA GSYAGAVNRL SSAEAASRVS SNIAAIASGG ASALPSVISN    60
IYSGVVASGV SSNEALIQAL LELLSALVHV LSSASIGNVS SVGVDSTLNV VQDSVGQYVG   120
```

ENGINEERED SPIDER SILK PROTEINS AND USES THEREOF

This application is a Divisional of co-pending U.S. application Ser. No. 16/314,501, filed on Dec. 31, 2018, which is a National Stage application under 35 U.S.C. § 371 of International Application No. PCT/EP2017/066119, having an International Filing Date of Jun. 29, 2017, which claims the benefit of European Application Serial No. 16177521.8 filed Jul. 1, 2016. Each of the above applications is hereby expressly incorporated by reference, in its entirety, into the present application.

REFERENCE TO SEQUENCE LISTING SUBMITTED VIA EFS-WEB

This application includes an electronically submitted sequence listing in .xml format. The .xml file contains a sequence listing entitled "0104_0915 PUS2_Sequence_Listing.xml" created on Aug. 24, 2022, and is 127,600 bytes in size. The sequence listing contained in this .xml file is part of the specification and is hereby incorporated by reference herein in its entirety.

TECHNICAL FIELD

The present invention relates to the field of engineered spider silk proteins, and methods for producing fibers of such proteins.

BACKGROUND TO THE INVENTION

Spider silk is composed of spidroins that are produced in abdominal glands. Most spiders produce up to 7 different types of silk in different glands, which are used for specific purposes and have different mechanical properties. Two of the toughest silks produced by orbweavers include the dragline silk (from the major ampullate gland) and the minor ampullate silk (from the minor ampullate gland). The majority of spidroins, including major ampullate spidroins (MaSps) and minor ampullate spidroins (MiSps), share a common architecture of a non-repetitive N-terminal domain (NT), an extensive repetitive region (REP) and a non-repetitive C-terminal domain (CT). Since spiders are territorial and produce small amounts of silk, any industrial application of spider silk requires the production of recombinant spidroins and the generation of artificial spider silk fibers. Spidroins can be produced in for example bacteria, yeast and insect cells but the recombinant proteins obtained so far are most often quite different from their natural counterparts with one or both of the terminal domains lacking, or the repeat region is engineered from iterated consensus repeats. Moreover, the produced spidroins have been obtained in too poor yields for the process to be scalable and/or have low solubility in water, probably owing in part to their inherent high tendency to self-assemble, but use of suboptimal spidroin constructs likely contribute to previous shortcomings in terms of production levels and solubility. Surprisingly, even when solvents such as hexafluoroisopropanol (HFIP) and formic acid are used, the solubility of the recombinant spidroins is far from the extreme solubility of spidroins in the native dope, which displays a protein concentration of 30-50% w/w, i.e. 300-500 mg/ml.

Progress in the analyses of the conditions in the spider silk glands and spinning ducts has unraveled that pH is gradually lowered from 7.6 to along the gland. The changes in conditions lead to specific conformational changes in the terminal domains, which result in fiber formation via a lock and trigger mechanism. During storage in the silk gland, at neutral pH, the NT is monomeric and highly soluble, which may contribute to the solubility of the entire spidroin. More important for the present application is the fact that when pH is lowered in the spinning duct, NT forms stable dimers, which locks the spidroins into large networks. The effects of pH on CT are not settled, and different effects have been observed. In one study (Andersson et al, PLoS Biol 12(8): e1001921. doi:10.1371/journal.pbio.1001921) decrease in pH resulted in that CT got destabilized, unfolded and turned into R-sheet amyloid-like fibrils. The structural conversion of CT is hypothesized to trigger the transition of the repetitive region into R-sheet conformation, in analogy with the nucleation phenomenon seen in amyloid fibril formation. Dehydration of the spinning dope likely takes place along the duct of the silk gland and shear forces generated along the narrowing duct affect the spidroin terminal domains. Molecular dynamics simulations indicate that shear forces play a significant role also in the structural conversion of the repetitive region.

Engineered recombinant spider silk proteins have been described in WO2007/078239. Methods for producing polymers of spider silk proteins are described in WO2010/123450. Given the shortcomings of the known engineered spider silk proteins and the methods of producing polymers from them, there is a need in the art for improved engineered spider silk proteins.

Thus, an object of the present invention is the provision of improved engineered spider silk proteins, in particular having high solubility in water, allowing scalable production, and being able to polymerize in a biomimetic fashion to form truly spider silk-like and useful fibers. Another object of the present invention is the provision of improved methods for producing fibers of engineered spider silk proteins, resulting in fibers having improved and useful mechanical properties, in particular as compared to known fibers in as-spun state.

Definitions

The terms spidroins and spider silk proteins are used interchangeably throughout the description and may refer to both native and recombinant proteins, dependent on the context.

The term minispidroin refers to an engineered variant of a spidroin, bearing a much shorter repetitive region than native spidroins.

Sequence identity expressed in percentage (or synonymously % identity) is defined as the value determined by comparing two optimally aligned sequences over a comparison window, wherein a portion of the sequence in the comparison window may comprise additions or deletions (i.e., gaps) as compared to the reference sequence (which does not comprise additions or deletions) for optimal alignment of the two sequences. The percentage is calculated by determining the number of positions at which identical amino acid residue occurs in both sequences to yield the number of matched positions, dividing the number of matched positions by the total number of positions in the window of comparison and multiplying the result by 100 to yield the percentage of sequence identity. Unless indicated otherwise, the comparison window is the entire length of the sequence being referred to. In this context, optimal alignment is the alignment produced by the BLASTP algorithm as implemented online by the US National Center for Biotechnology Information (see The NCBI Handbook [Internet], Chapter 16, the most recent version on the date of filing), with the following input parameters: Word length=3, Matrix=BLOSUM62, Gap cost=11, Gap extension cost=1.

The term % similarity, as used throughout the specification and the appended claims, is calculated as described for "% identity", with the exception that the hydrophobic residues Ala, Val, Phe, Pro, Leu, Ile, Trp, Met and Cys are similar; the basic residues Lys, Arg and His are similar; the acidic residues Glu and Asp are similar; and the hydrophilic, uncharged residues Gln, Asn, Ser, Thr and Tyr are similar. The remaining natural amino acid Gly is not similar to any other amino acid in this context.

The terms soluble and solution in the present context have the meaning that the protein in question is dissolved in a solvent with no visible aggregates and does not precipitate from the solvent at 60 000 g.

All the Genbank accession numbers cited herein refer to entries as in the most recent version of the Genbank database on the date of filing.

BRIEF DESCRIPTION OF THE FIGURES

FIG. 1: Alignment of spidroin NT domains listed in Table 2 using ClustalW.

FIG. 2: NT2RepCT has a high expression level and aqueous solubility.

FIG. 3. Biomimetic spinning of artificial spider silk. FIG. 3B: Photo of the fiber as it is spun in the low pH aqueous collection bath. FIG. 3C: Wet fiber nest in low pH buffer. FIG. 3D: Fibers rolled up onto a frame. Fiber diameter in b-c approximately 40 μm. Fiber diameter in d 15 μm. Scale bar in FIG. 3B is 3 mm and in FIGS. 3C-3D is 5 mm.

FIG. 4. Characterization of NT2RepCT fibers.

FIG. 7: NT2RepCT micelles studied by electron microscopy.

FIG. 8: Scanning electron micrographs of NT2RepCT fibres.

FIG. 10A: NT dimerizes at low pH. FIG. 10B: Low pH induces dimer destabilization of CT and shifts the protein towards higher charge states within the same time scale as observed for NT2RepCT aggregation.

FIG. 12: Pilot experiments on 3D-printing.

FIG. 13: SDS-PAGE analysis of the purification process of NT2+2RepCT. TP=total protein; Sup=supernatant after lysis; P=pellet after lysis; P-s=supernatant from overnight frozen pellet; FT=flow through (Ni-NTA column); E=protein eluted from column.

160223_1: Spun into 500 mM NaAc, 200 mM NaCl, pH 5.

160223_2: Spun into 500 mM NaAc, 200 mM NaCl, 15% PEG, pH 5.

160223_4: Post-stretched in 50% methanol and 500 mM NaAc, 200 mM NaCl, pH 5

160223_5: Post-stretched in 30% PEG.

Figure 15:
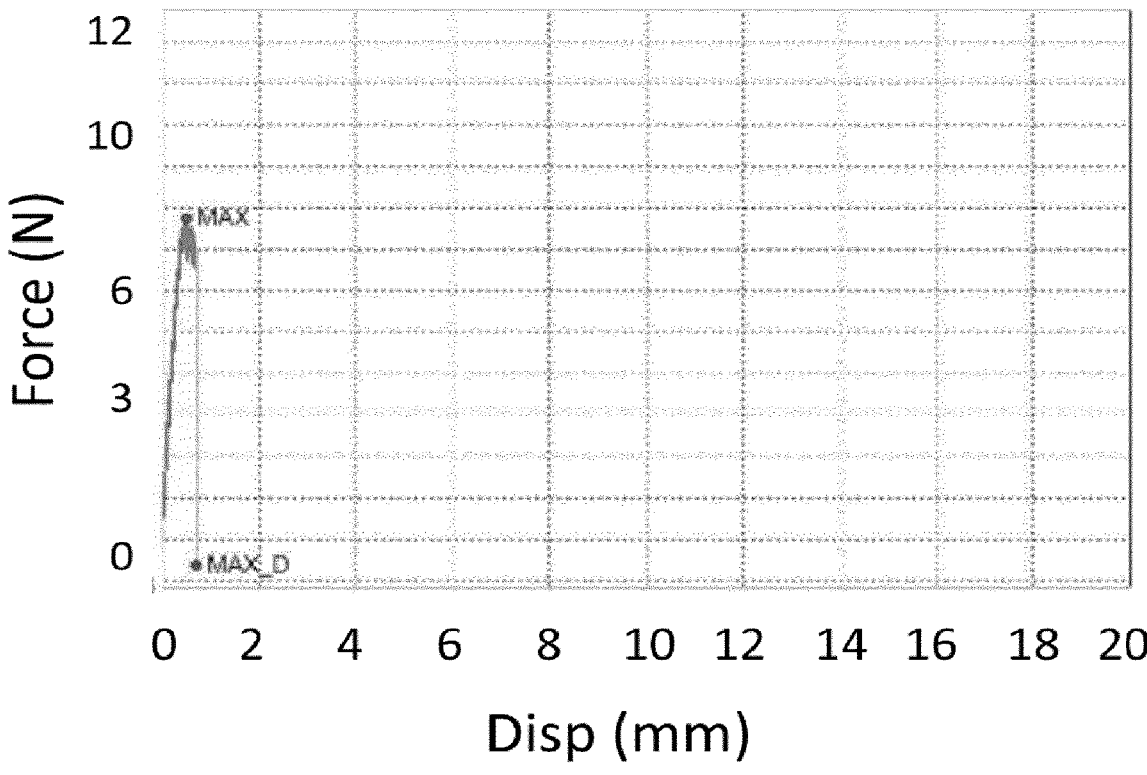

FIG. 15. 160303_4: Force/displacement curve of NT2RepCT fibers spun into 500 mM NaAc, 200 mM NaCl, pH 4.25.

Figure 16:
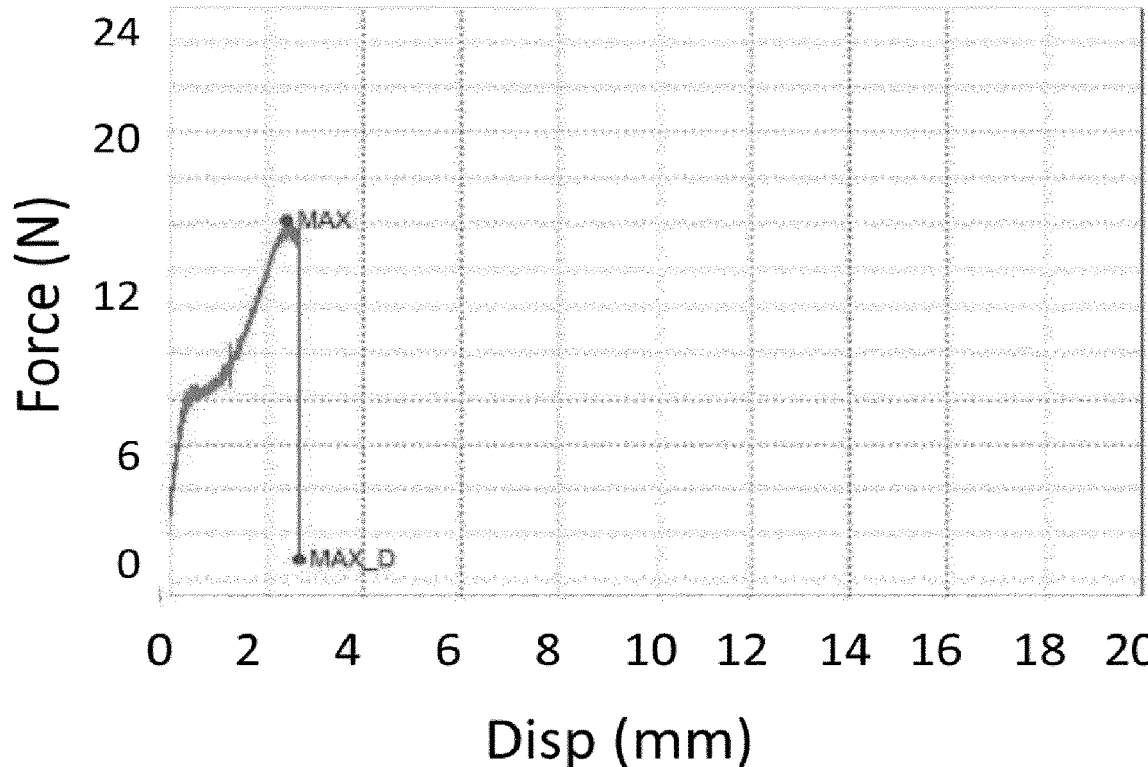

FIG. 16. 160303_5a: Force/displacement curve of NT2RepCT fibers spun into 500 mM NaAc, 200 mM NaCl, pH 5 at room temperature and, subsequently post-stretched in 80% aqueous isopropanol.

Figure 17:
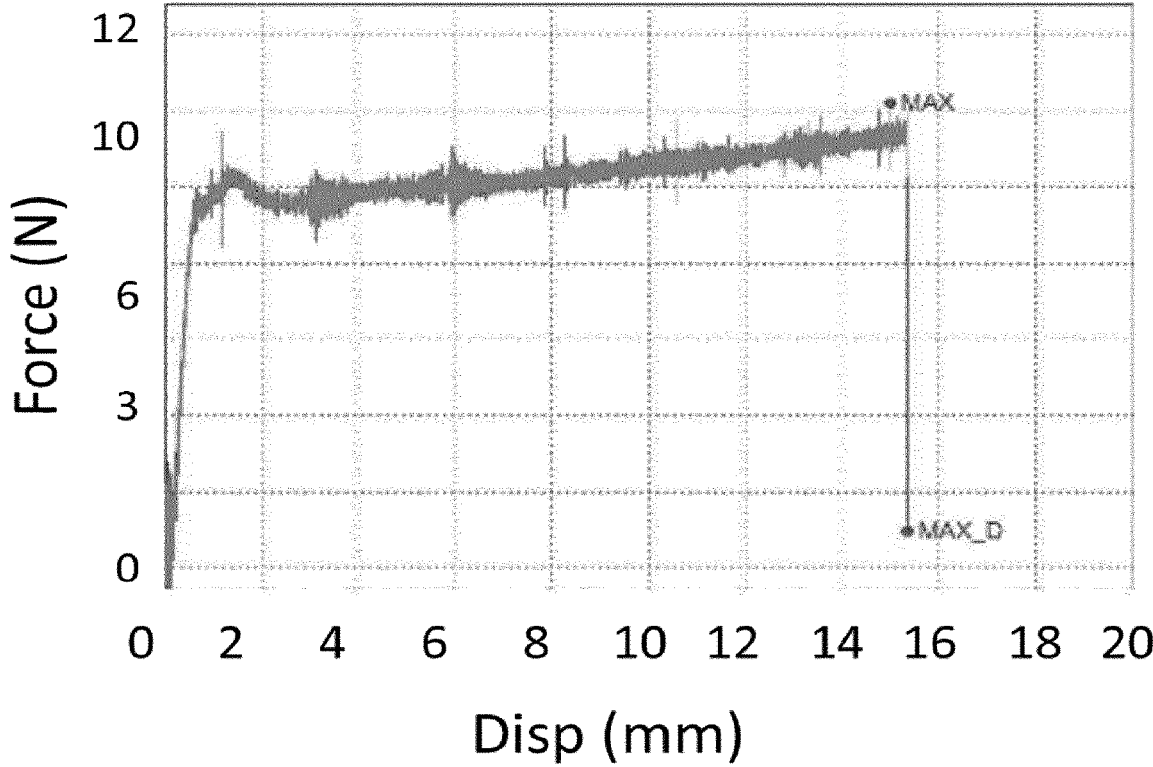

FIG. 17. 160303_5b: Force/displacement curve of NT2RepCT fibers spun into 500 mM NaAc, 200 mM NaCl, pH 5 at room temperature and subsequently dipped in 80% aqueous isopropanol.

Figure 18:
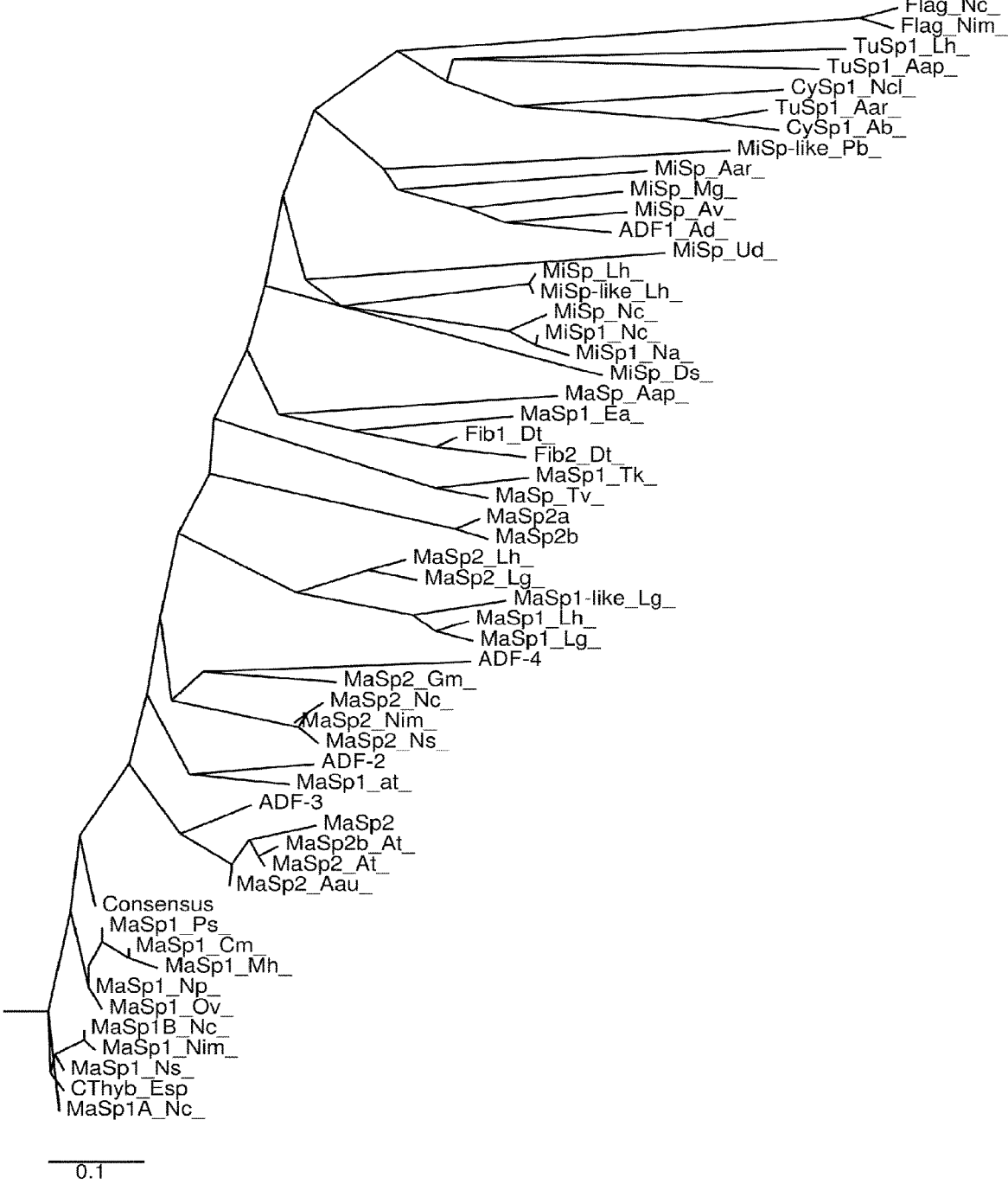

FIG. 18. Phylogenetic tree of the CT-domain sequences in Table 1.

Figures 19A, 19B, 19C:
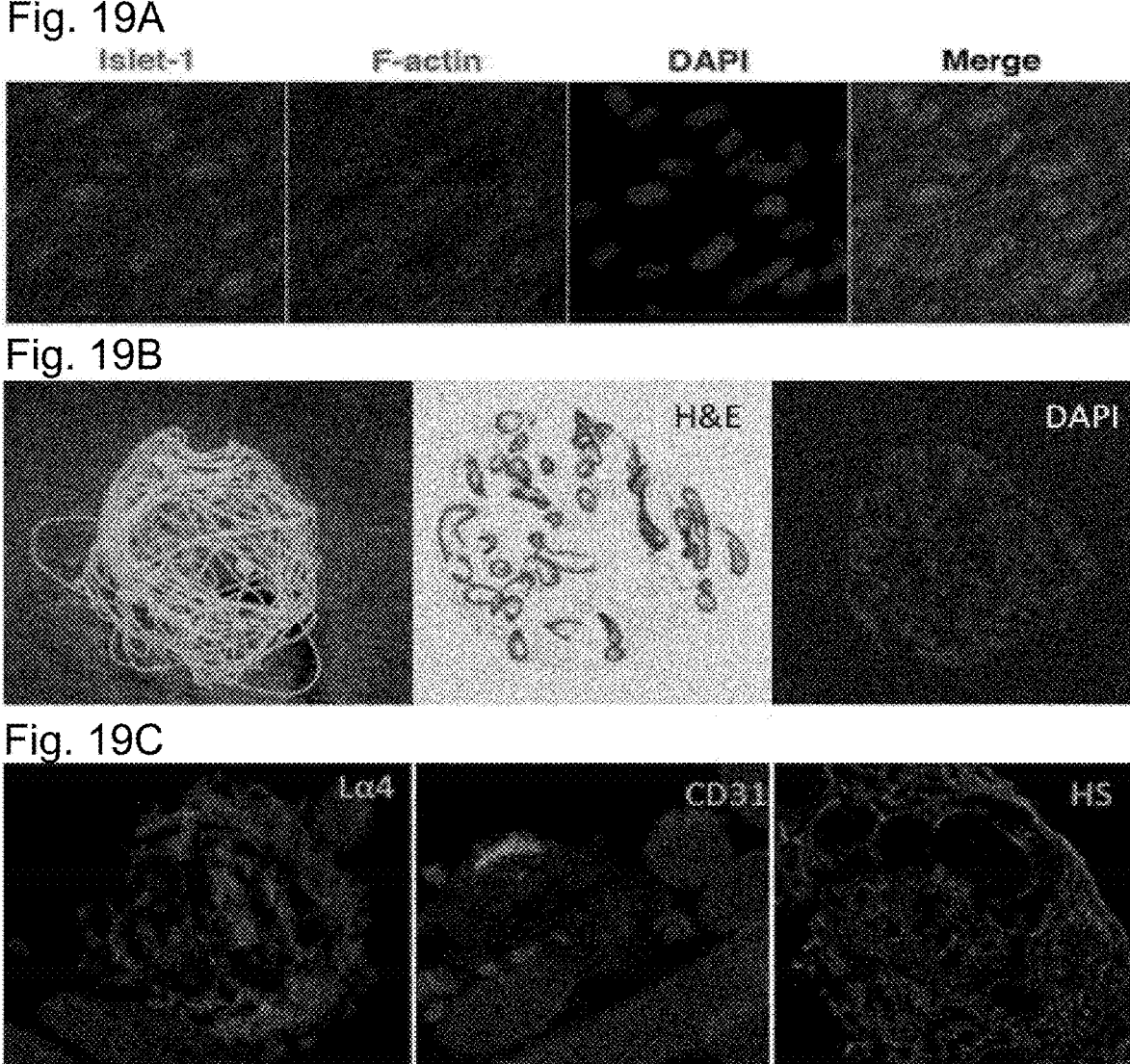

FIG. 19: FIG. 19A: hfcMSCs maintain the expression of Isl1+ and F-actin when expanded on spider silk foam. DAPI stain (blue) shows nuclei. FIG. 19B: Spun fibers can be assembled into ~1 cm Ø balls (left). Fetal cardiac progenitor cells were grown on dense fiber balls, which were sectioned, and stained with haematoxylin and eosin (H&E;middle) and DAPI. FIG. 19C: Cryosectioned cells on spider silk balls show expression of laminin α4, CD31 and heparansulfate.

Figure 20:
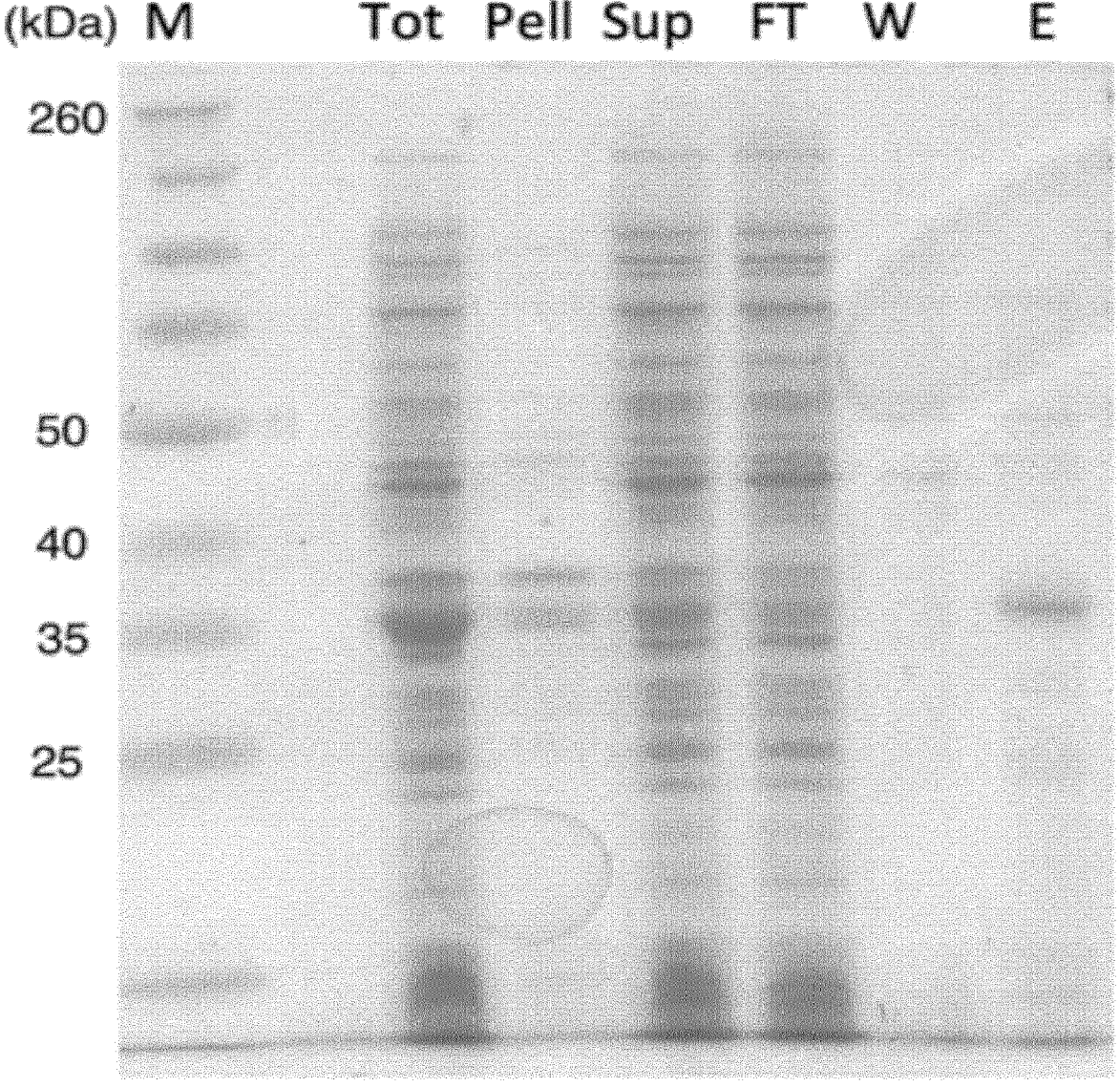

FIG. 20. SDS-PAGE of purified NT2RepCT(MiSp Ds) and different purification steps. M=Spectra Broadrange protein marker (sizes in kilodalton is shown to the left), Tot=total cell lysate, Pell=pellet, Sup=supernatant after centrifugation of whole cell lysate, FT=flow through Ni-NTA column, W=wash, E=target protein NT2RepCT(MiSp Ds) eluted from the Ni-NTA column.

Figure 21:
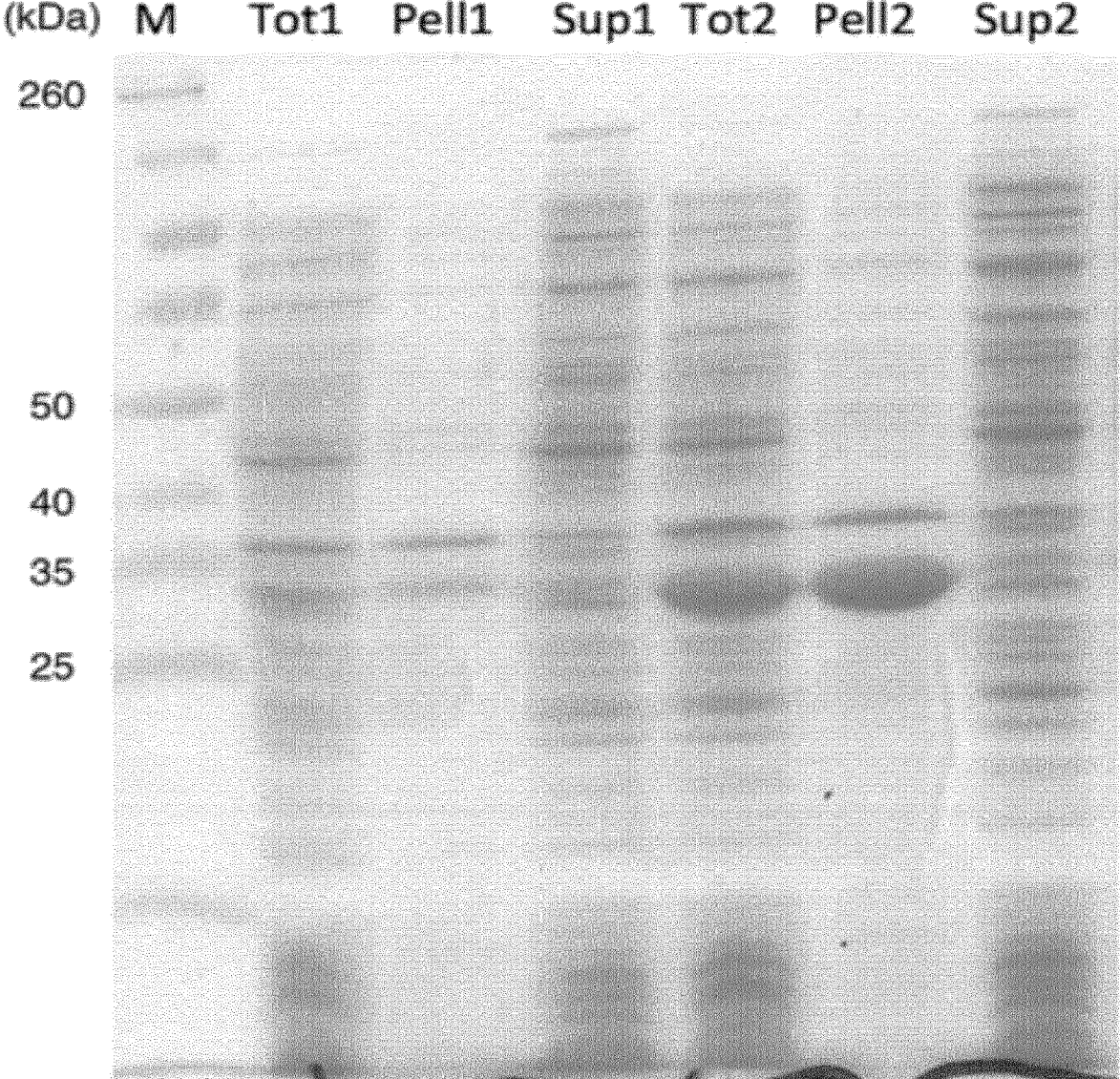

FIG. 21. SDS-PAGE of (1)NT2RepCT(MaSp1 Ea) and (2) NT2RepCT(ADF-4). M=Spectra Broadrange protein marker (sizes in kilodalton is shown to the left), Tot=total cell lysate, Pell=pellet, Sup=supernatant after centrifugation of whole cell lysate.

Figure 22:
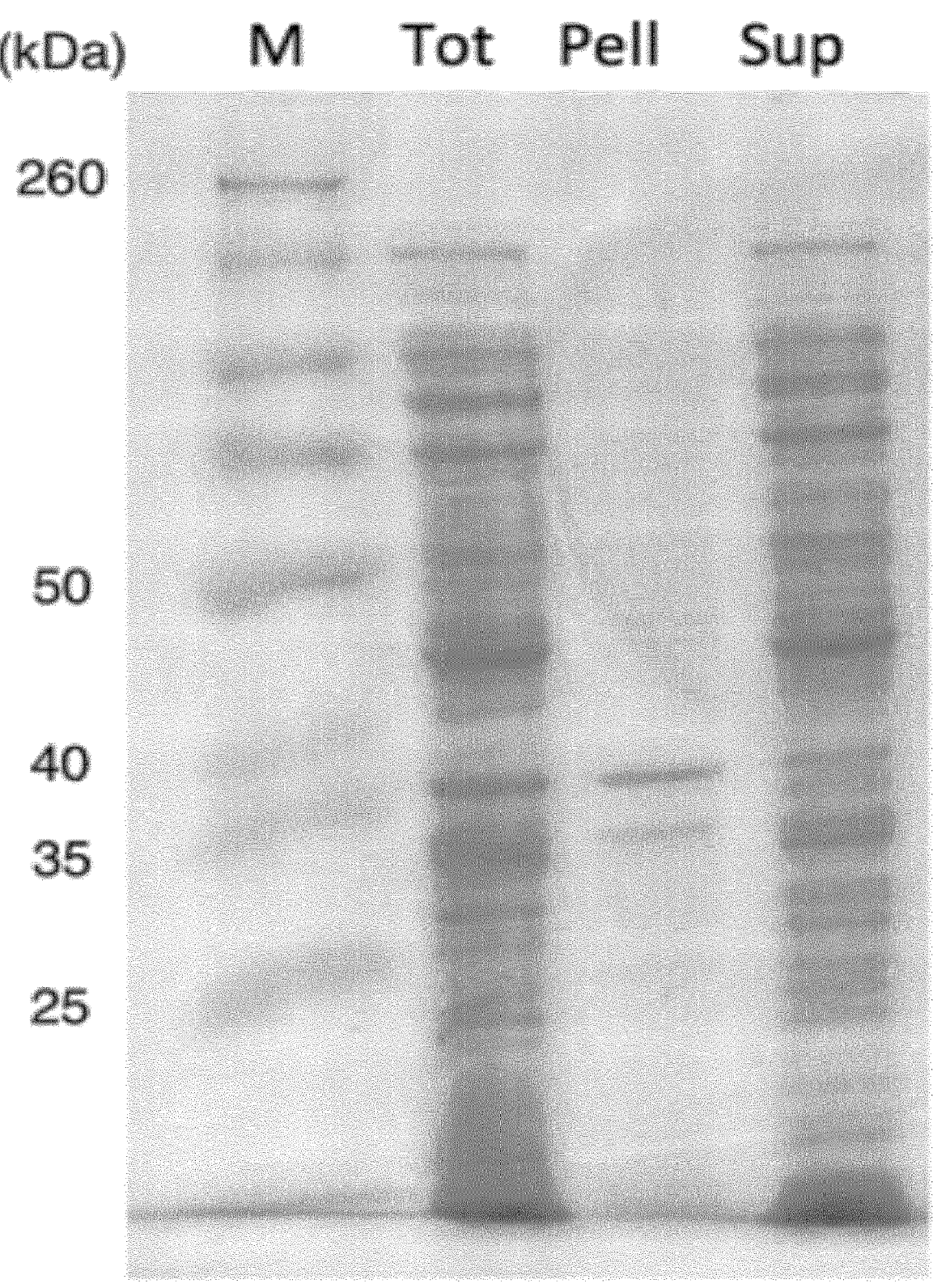

FIG. 22. SDS-PAGE of NT2RepCT(MiSp Lh). M=Spectra Broadrange protein marker (sizes in kilodalton is shown to the left), Tot=total cell lysate, Pell=pellet, Sup=supernatant after centrifugation of whole cell lysate.

SUMMARY OF THE INVENTION

The present invention relates to the following items. The subject matter disclosed in the items below should be regarded disclosed in the same manner as if the subject matter were disclosed in patent claims.

1. A recombinant spider silk protein, consisting of no more than 800 amino acids, comprising a set of domains arranged according to the formula (NT)-REP-CT, wherein:
   a. the optional NT-domain, if present, consists of a sequence of 100 to 160 amino-acid residues derived from the N-terminal domain of a spider silk protein;
   b. the REP-domain consists of a sequence of 30 to 600 amino acid residues derived from the repetitive segment of a spider silk protein;
   c. the CT-domain consists of a sequence of 70 to 120 amino acid residues derived from the C-terminal domain of a spider silk protein, selected from:
      i. a sequence of 72 to 110 amino acid residues derived from the C-terminal domain of a spider silk protein, wherein the sequence comprises at least 7 residues independently selected from K, R, E and D;
      ii. a sequence having at least 81% identity to SEQ ID NO: 64 or any one of SEQ ID NOs: 62-65 or 67-73; and
      iii. a sequence having at least 70% identity to SEQ ID NO: 64 or any one of SEQ ID NOs: 62-65 or 67-73, wherein the sequence comprises at least 7 residues independently selected from K, R, E and D.

2. The recombinant spider silk protein according to any of the preceding items, wherein the CT-domain consists of a sequence of 72 to 110 amino acid residues derived from the C-terminal domain of a spider silk protein, wherein the sequence comprises at least 7 residues independently selected from K, R, E and D 3. The recombinant spider silk protein according to any of the preceding items, wherein the CT-domain consists of a sequence having at least 81%, preferably at least 82%, 83%, 84%, 85%, 86%, 87%, 88% or 89%, more preferably at least 90%, most preferably at least 95% sequence identity to SEQ ID NO: 64 or any one of SEQ ID NOs: 62-65 or 67-73.

4. The recombinant spider silk protein according to any of the preceding items, wherein the CT-domain consists of a sequence having at least 81%, preferably at least 82%, 83%, 84%, 85%, 86%, 87%, 88% or 89%, more preferably at least 90%, most preferably at least 95% sequence identity to SEQ ID NO: 64.

5. The recombinant spider silk protein according to any of the preceding items, wherein the CT-domain consists of a sequence having at least 70%, preferably at least 72%, 75%, 77%, 80%, 83%, 85%, 87% or 89%, more preferably at least 90%, most preferably at least 95% sequence identity to SEQ ID NO: 64, wherein the sequence comprises at least 7 residues independently selected from K, R, E and D.

6. The recombinant spider silk protein according to any of the preceding items, wherein the CT-domain consists of at least 80, preferably at least 90, amino acid residues.

7. The recombinant spider silk protein according to any of the preceding items, wherein the CT-domain consists of less than 110 amino acid residues.

8. The recombinant spider silk protein according to any of the preceding items, wherein the CT-domain consists of 87-97 amino acid residues.

9. The recombinant spider silk protein according to any of the preceding items, wherein the CT-domain sequence does not comprise a C residue at the beginning of helix 4.

10. The recombinant spider silk protein according to any of the preceding items, wherein the CT-domain sequence does not comprise a C residue at a position aligning with the positions 47-55 of SEQ ID NO: 49.

11. The recombinant spider silk protein according to any of the preceding items, wherein the NT-domain is present.

12. The recombinant spider silk protein according to any of the preceding items, wherein the NT-domain is present and consists of a sequence derived from the N-terminal domain of a major ampullate gland spider silk protein.

13. The recombinant spider silk protein according to any of the preceding items, wherein the NT-domain is present and consists of a sequence having at least 50% identity to SEQ ID NO: 2 and/or at least 80% identity to SEQ ID NO: 1 or any individual amino acid sequence in Table 2.

14. The recombinant spider silk protein according to any of the preceding items, wherein the NT-domain is present and consists of a sequence having at least 80% identity to SEQ ID NO: 1.

15. The recombinant spider silk protein according to any of the preceding items, wherein the NT-domain is present and consists of at least 110, preferably at least 120, amino acid residues.

16. The recombinant spider silk protein according to any of the preceding items, wherein the NT-domain is present and consists of at most 160, preferably less than 140 amino acid residues.

17. The recombinant spider silk protein according to any of the preceding items, wherein the NT-domain is present and consists of 130-140 amino acid residues.

18. The recombinant spider silk protein according to any of the preceding items, wherein the REP domain comprises alternating alanine-rich A-segments and glycine-rich G-segments.

19. The recombinant spider silk protein according to any of the preceding items, wherein the REP domain comprises alanine-rich A-segments and glycine-rich G-segments, wherein the sum of the number of A segments and the number of G segments in the REP-domain is 3 to 30, preferably 4-20, more preferably 4-10, most preferably 4-8.

20. The recombinant spider silk protein according to any of the preceding items, wherein the REP domain comprises alanine-rich A-segments and glycine-rich G-segments, wherein each A segment is an amino acid sequence of from 8 to 20 amino acid residues, wherein at least 60%, preferably at least 65%, more preferably at least 70%, most preferably at least 75% of the amino acid residues are Ala.

21. The recombinant spider silk protein according to any of the preceding items, wherein the REP domain comprises alanine-rich A-segments and glycine-rich G-segments, wherein each G segment is an amino acid sequence of from 12 to 40 amino acid residues, wherein at least 30%, preferably at least 35%, most preferably at least 40% of the amino acid residues are Gly.

22. The recombinant spider silk protein according to any of the preceding items, wherein the REP domain comprises alanine-rich A-segments and glycine-rich G-segments, wherein each A segment contains at least one stretch of 5 consecutive, preferably 6 consecutive A residues.

23. The recombinant spider silk protein according to any of the preceding items, wherein the REP domain comprises alanine-rich A-segments and glycine-rich G-segments, wherein each G segment contains at least one, preferably at least two GGX motif(s), where X designates any amino acid.

24. The recombinant spider silk protein according to any of the preceding items, wherein the REP-domain is selected from the group consisting of $L(AG)_nL$, $L(AG)_nAL$, $L(GA)_nL$, $L(GA)_nGL$, $LG(AG)_nL$, wherein n is an integer from 2 to 10;

each individual A segment is an amino acid sequence of from 8 to 18 amino acid residues, wherein from 0 to 3 of the amino acid residues are not Ala, and the remaining amino acid residues are Ala;

each individual G segment is an amino acid sequence of from 12 to 30 amino acid residues, wherein at least 40% of the amino acid residues are Gly; and each individual L segment is a linker amino acid sequence of from 0 to 30 amino acid residues, preferably 0-25.

25. The recombinant spider silk protein according to item 24, wherein each individual A segment has at least 80% identity to an amino acid sequence selected from the group of amino acid residues 7-19, 43-56, 71-83, 107-120, 135-147, 171-183, 198-211, 235-248, 266-279, 294-306, 330-342, 357-370, 394-406, 421-434, 458-470, 489-502, 517-529, 553-566, 581-594, 618-630, 648-661, 676-688, 712-725, 740-752, 776-789, 804-816, 840-853, 868-880, 904-917, 932-945, 969-981, 999-1013, 1028-1042 and 1060-1073 of SEQ ID NO: 3; and each individual G segment has at least 80% identity to an amino acid sequence selected from the group of amino acid residues 20-42, 57-70, 84-106, 121-134, 148-170, 184-197, 212-234, 249-265, 280-293, 307-329, 343-356, 371-393, 407-420, 435-457, 471-488, 503-516, 530-552, 567-580, 595-617, 631-647, 662-675, 689-711, 726-739, 753-775, 790-803, 817-839, 854-867, 881-903, 918-931, 946-968, 982-998, 1014-1027, 1043-1059 and 1074-1092 of SEQ ID NO: 3.

26. The recombinant spider silk protein according to any of items 24-25 wherein n is 2 or 4.

27. The recombinant spider silk protein according to item 26, wherein the selected REP domain is $LG(AG)_2L$ or $LG(AG)_4L$.

28. The recombinant spider silk protein according to item 27, wherein the selected REP domain is $LG(AG)_2L$.

29. The recombinant spider silk protein according to any of the preceding items, wherein the REP-domain consists of 40-600, preferably 50-500, more preferably 60-400, most preferably 70-300 amino acids.

30. The recombinant spider silk protein according to any of the preceding items, wherein the spider silk protein comprises a set of domains according to the formula NT-L-REP-L-CT, wherein each individual L segment is a linker amino acid sequence of from 1 to 20 amino acid residues.

31. The recombinant spider silk protein according to any of the preceding items, wherein the spider silk protein consists of no more than 600, preferably no more than 500, more preferably no more than 400, yet more preferably no more than 300, most preferably no more than 250 amino-acid residues in total.

32. The recombinant spider silk protein according to any of the preceding items, wherein the protein exhibits highly pH-dependent solubility.

33. The recombinant spider silk protein according to any of the preceding items, wherein the protein exhibits highly pH-dependent solubility defined as least 10 times, preferably 50 times, more preferably 100 times higher solubility in aqueous 20 mM Tris-HCl pH8.0 buffer than in aqueous 500 mM Na-acetate, 200 mM NaCl at pH5.0.

34. The recombinant spider silk protein according to any of the preceding items, wherein the protein is soluble in aqueous 20 mM Tris-HCl pH8.0 buffer and polymerizes in aqueous 500 mM Na-acetate, 200 mM NaCl at pH5.0, at a concentration of 50 mg/ml, preferably at a concentration of 100 mg/ml, more preferably 200 mg/ml, most preferably 300 mg/ml.

35. The recombinant spider silk protein according to any of the preceding items, comprising a sequence having at least 80%, preferably at least 85%, more preferably at least 90%, most preferably at least 95% sequence identity to SEQ ID NO: 11.

36. The recombinant spider silk protein according to any of the preceding items, consisting of a sequence identical to SEQ ID NO: 11.

37. A non-denaturing solution of a spider silk protein according to any of the preceding items, having a protein concentration of said spider silk protein of at least 100 mg/ml, preferably 150 mg/ml, most preferably 200 mg/ml.

38. A polymer of a spider silk protein according to any of items 1-36, preferably a fiber, film, foam, net or mesh.

39. The polymer according to item 38, being a fiber having a length of at least 10 cm, preferably at least 1 m, more preferably at least 5 m, yet more preferably at least 10 m, still more preferably at least 50 m, most preferably at least 100 m.

40. The polymer according to any of items 38-39, being a fiber having diameter 100 µm, preferably less than 50 µm, more preferably less than 20 µm, most preferably less than 10 µm.

41. The polymer according to any of items 38-40, having toughness of $\geq 3$ $MJ/m^3$, preferably $\geq 10$ $MJ/m^3$, more preferably $\geq 20$ $MJ/m^3$, most preferably $\geq 40$ $MJ/m^3$.

42. A method for producing a polymer of a spider silk protein, comprising the steps of:

a. providing a first liquid medium comprising a spider silk protein according to any of items 1-36 in solution in said medium at a concentration of at least 100 mg/ml, preferably 200 mg/ml, most preferably 300 mg/ml;

b. adjusting the properties of the first liquid medium such that it allows polymerisation of said spider silk protein;

c. allowing the spider silk protein to form polymers; and d. isolating the spider silk protein polymers.

43. The method according to item 42, wherein the properties of the first liquid medium are adjusted by extruding the solution of a spider silk protein into a second fluid medium having properties that allow polymerisation of said spider silk protein.

44. The method according to any of items 42-43, wherein the first liquid medium in step (a) has a pH of at least 6.4.

45. The method according to any of items 42-44, wherein the first liquid medium in step (a) has a salt concentration of less than 100 mM.

46. The method according to any of items 42-45, wherein the first liquid medium in step (a) is an aqueous solution comprising less than 10% (v/v) of organic solvents.

47. The method according to any of items 42-46, wherein the properties of the first liquid medium in steps (b)-(d) are adjusted to pH 6.3 or below, in the presence of a sufficient salt concentration for polymerisation of said spider silk protein.

48. The method according to any of items 42-47, wherein the properties of the first liquid medium in steps (b)-(d) are adjusted to at least 100 mM salt concentration and to pH 6.3 or below.

49. The method according to any of items 42-48, wherein the properties of the first liquid medium in steps (b)-(d) are adjusted to having a concentration of an organic solvent sufficient to induce polymerization.

50. The method according to item 42, wherein the second fluid medium has pH 6.3 or below, and a sufficient salt concentration for polymerisation of said spider silk protein.

51. The method according to any of items 42 or 50, wherein the second fluid medium comprises an organic solvent at a concentration sufficient to induce polymerization.

52. The method according to any of items 42 or 50-51, wherein the second fluid medium comprises a hygroscopic polymer, such as PEG.

53. The method according to any of items 42 or 50-52, wherein the extrusion is through a capillary having an opening with a cross-sectional area in the interval 20-50000 μm$^2$, preferably 30-30000 μm$^2$, more preferably 40-10000 μm$^2$, yet more preferably 50-5000 μm$^2$, most preferably 70-800 μm$^2$.

54. The method according to any of items 42 or 50-52, wherein the extrusion is performed at a linear flow rate of 0.1-500 mm/s, more preferably 0.5-200 mm/s, most preferably 1-100 mm/s.

55. The method according to any one of items 42-54, wherein said polymer is a fiber, film, foam, net or mesh, preferably a fiber, more preferably a polymer according to any of items 38-41.

56. A nucleic acid encoding for a protein according to any of items 1-36.

57. An expression vector comprising a nucleic acid according to item 56 operatively coupled to a promoter.

58. A host cell comprising a nucleic acid according to item 56, or an expression vector according to item 57.

59. A method of producing a recombinant spider silk protein, comprising:

a. Culturing a host cell according to item 58 in conditions allowing production of the protein;

b. Isolating said protein from said culture.

60. The method according to any of items 42-55, wherein the polymer is extruded in a 3D-printing apparatus.

61. A use of a spider silk protein according to any of items 1-36, or a polymer according to any of items 38-41, in the manufacture of an implantable material or a cell culture scaffold.

62. A use of a spider silk protein according to any of items 1-36, or a polymer according to any of items 38-41 as an implantable material or a cell culture scaffold.

DETAILED DESCRIPTION

The inventors postulated that a prerequisite that needs to be fulfilled in order to realize biomimetic spinning of artificial spider silk is to obtain spidroins that are pH responsive and display solubility levels in water that equal those of spidroins in the native spinning dope. It struck the inventors that the aqueous solubility and pH responsiveness of NT and CT, respectively, might differ between spidroins from different spider species and silk types.

The inventors further hypothesized that a recombinant minispidroin that comprises a highly soluble NT and a likewise very soluble CT would be fully pH sensitive and advantageous from a solubility point-of-view. To test the hypothesis, the inventors designed a minispidroin composed of NT from *E. australis* MaSp1 and CT from *A. ventricosus* MiSp bracketing a short repetitive region from *E. australis* (Example 1), and found that the minispidroin indeed has unprecedented solubility combined with a capability to form useful, and in certain respects, superior fibers in a biomimetic, pH-dependent manner (Examples 2-10), compared to prior art minispidroins (comparative Example 11).

Further experiments show that a minispidroin comprising CT from *A. ventricosus* MiSp coupled to a short repetitive region from *E. australis* (Example 12) also is able to form fibers in a pH-dependent manner never previously seen with minispidroins not comprising an NT-domain.

Yet further studies on an engineered minispidroin with twice as long repetitive region than in Example 1 showed that advantages of combining highly soluble and pH-sensitive NT and CT are not limited to minispidroins with very short repetitive regions (Example 13).

Designed Spider Silk Proteins

In a first aspect of the present invention, there is provided a recombinant spider silk protein, preferably consisting of no more than 800 amino acids, comprising a set of domains arranged according to the formula (NT)-REP-CT, wherein:

a. the optional NT-domain, if present, consists of a sequence of 100 to 160 amino-acid residues derived from the N-terminal domain of a spider silk protein;

b. the REP-domain consists of a sequence of 30 to 600 amino acid residues derived from the repetitive segment of a spider silk protein;

c. the CT-domain consists of a sequence of 70 to 120 amino acid residues derived from the C-terminal domain of a spider silk protein selected from:

i. a sequence of 72 to 110 amino acid residues derived from the C-terminal domain of a spider silk protein, wherein the sequence comprises at least 7 residues independently selected from K, R, E and D;

ii. a sequence having at least 81% identity to SEQ ID NO: 15 or any one of SEQ ID NOs: 62-65 or 67-73; and iii. a sequence having at least 70% identity to SEQ ID NO: 64 or any one of SEQ ID NOs: 62-65 or 67-73, wherein the sequence comprises at least 7 residues independently selected from K, R, E and D.

Following convention, the formula is read as N-terminus being on the left and the C-terminus on the right side of the formula.

Properties of the CT Domain

The role of the NT domain in physiological spider silk polymerization has been recognized earlier (see e.g. WO2010/123450). The extremely high solubility of the NT domain is thought to contribute to making the extremely high protein concentration possible in the physiological (native) spider silk dope, and it has been recognized that the highly pH-dependent properties of the NT domains is a crucial factor for allowing rapid polymerisation of the dope.

In contrast, most of the CT domains from the major ampullate gland silk (that has been studied most) do not exhibit extreme solubility nor do they exhibit pH-sensitive solubility in the pH 5-7.5 range.

However, the inventors have discovered that certain CT domains derived from other types of silk such as the minor ampullate gland silk do in fact exhibit extreme solubility, which is pH-dependent.

When analyzing primary structure alignments of CTs it struck the inventors that they differ in the number of charged amino acid residues, i.e. the CT from *Euprosthenops australis* MaSp1 contains four charged residues while the *Araneus ventricosus* MiSp CT has seven charged residues. The inventors therefore hypothesized that the number of charges in the CT positively correlates to the solubility of the CT and therefore using CTs with a high number of charged amino acid residues could be beneficial for the solubility of recombinantly produced spidroins. Thus, without wishing to be bound by a particular theory, the inventors believe that residues that are charged in the physiological conditions in the spider silk gland (K, R, E and D) may be important for the solubility and the pH-dependency. Histidine is not regarded as charged in this context, as it is to a significant extent non-charged at the relevant pH in said physiological conditions.

As shown in Table 1 below, the major ampullate gland spider silk CT-domains, which to the extent they have been studied, do not appear to exhibit extreme solubility and/or pH-dependent solubility, have less than 7 of these charged residues. In contrast, most minor ampullate gland spider silk CT-domains have at least 7 of these charged residues. This observation was validated experimentally (see Example 15) by comparing different CT-domains differing in charged residue content either naturally or by genetic engineering.

Thus, the CT-domain sequence may be a sequence of 72 to 110 amino acid residues derived from the C-terminal domain of a spider silk protein, wherein the sequence comprises at least 7 residues independently selected from K, R, E and D.

Preferably, the CT-domain sequence does not comprise a C residue at the beginning of helix 4, as defined according to the NMR structures with PDB id 2MFZ (MiSp CT, *A. ventricosus*) or 2M0M (MiSp *N. antipodiana*). If a structure of a CT domain has not been experimentally determined, a secondary structure prediction algorithm, such as psipred, may be used to define helix 4. Said C residue is a characteristic feature of major ampullate gland CT-domains but is generally missing in minor ampullate gland CT-domains. Preferably, the CT-domain sequence does not comprise a C residue at a position aligning with the positions 47-55 of SEQ ID NO: 49.

The CT-domain may be a sequence having at least 81%, preferably at least 82%, 83%, 84%, 85%, 86%, 87%, 88% or 89%, more preferably at least 90%, most preferably at least 95% sequence identity to any one of SEQ ID NOs: 62-65 or 67-73.

The CT-domain may be a sequence having at least 81%, preferably at least 82%, 83%, 84%, 85%, 86%, 87%, 88% or 89%, more preferably at least 90%, most preferably at least 95% sequence identity to SEQ ID NO: 64.

The CT domain sequence may be a sequence having at least 70%, preferably at least 72%, 75%, 77%, 80%, 83%, 85%, 87% or 89%, more preferably at least 90%, most preferably at least 95% sequence identity to SEQ ID NO: 64, or any one of SEQ ID NOs: 62-65 or 67-73, with the proviso that the sequence comprises at least 7 residues independently selected from K, R, E and D.

TABLE 1

| | | | | No. charged residues (K/R/E/D) | SEQ ID NO |
|---|---|---|---|---|---|
| Desig-nation | Species and Spidroin | Genbank accession no | AA sequence | | |
| MiSp-like(Pb) | MiSp-like protein [*Parawixia bistriata*] | ADG57595.1 | GAGAAAASGATGRVANSLGAMASGGI NALPGVFSNIFSQVSAASGGASGGAVLV QALTEVIALLLHILSSASIGNVSSQGLEGS MAIAQQAIGAYAG | 3 | 19 |
| MaSp1(Tk) | *Tetragnatha kauaiensis* MaSp1 | AF350285 | SLLSSPASNARISSAVSALASGAASGPGY LSSVISNVVSQVSSNSGGLVGCDTLVQA LLEAAAALVHVLASSSGGQVNLNTAGYT SQL | 3 | 20 |
| MaSp2(At) | major ampullate spidroin 2 [*Argiope trifasciata*] | AAZ15372.1 | AAASRLSSPQASSRVSSAVSTLVSSGPTN PASLSNAISSVVSQVSASNPGLSGCDVL VQALLEIVSALVHILGSSSIGQINYAASSQ YAQMVG | 4 | 21 |

Exemplary spidroin CT domains

TABLE 1-continued

Exemplary spidroin CT domains

| Designation | Species and Spidroin | Genbank accession no | AA sequence | No. charged residues (K/R/E/D) | SEQ ID NO |
|---|---|---|---|---|---|
| MaSp1A(Nc) | major ampullate spidroin 1 [*Nephila clavipes*] | AAT75312.1 | SAASRLSSPEASSRVSSAVSNLVSSGPTN SAALSSTISNVVSQIGASNPGLSGCDVLV QALLEVVSALIHILGSSSIGQVNYGSAGQ ATQIVGQSIYQALG | 5 | 22 |
| MaSp1B(Nc) | major ampullate spidroin 1 [*Nephila clavipes*] | AAT75311.1 | AAASRLSSPQASSRVSSAVSNLVASGPT NSAALSSTISNVVSQIGASNPGLSGCDVL IQALLEVVSALIHILGSSSIGQVNYGSAG QATQIVGQSVYQALG | 4 | 23 |
| MaSp1(Lh) | major ampullate spidroin 1 [*Latrodectus hesperus*] | ABR68856.1 | AAASALAAPATSARISSHASALLSNGPT NPASISNVISNAVSQISSSNPGASACDVL VQALLELVTALLTIIGSSNIGSVNYDSSGQ YAQVVTQSVQNAFA | 4 | 24 |
| MaSp2(Lh) | major ampullate spidroin 2 [*Latrodectus hesperus*] | ABD66603.1 | SAASALSSPTTHARISSHASTLLSSGPTN AAALSNVISNAVSQVSASNPGSSSCDVL VQALLEIITALISILDSSSVGQVNYGSSGQ YAQIVGQSMQQAMG | 4 | 25 |
| MaSp1-like(Lg) | major ampullate spidroin 1-like protein [*Latrodectus geometricus*] | AAZ15321.1 | PAASALAAPATSARISSHALTLLSNGPTN PASISNVISNAVSQISSSNPGYSSCDILVQ ALLELVTALLTIIGSSNVNDINYGSSGQYA QMVSQSVQNVFG | 4 | 26 |
| MaSp1(Ea) | major ampullate spidroin 1 [*Euprosthenops australis*] | CAJ00428.1 | NSVSRLSSPSAVSRVSSAVSSLVSNGQV NMAALPNIISNISSSVSASAPGASGCEVI VQALLEVITALVQIVSSSSVGYINPSAVN QITNVVANAMAQVMG | 4 | 27 |
| Flag(Nc) | flagelliform silk protein [*Nephila clavipes*] | AAC38847.1 | PGSPGGAYYPSSRVPDMVNGIMSAMQ GSGFNYOMFGNMLSQYSSGSGTCNPN NVNVLMDALLAALHCLSNHGSSSFAPS PTPAAMSAYSNSVGRMFAY | 4 | 28 |
| Flag(Nim) | flagelliform silk protein [*Nephila inaurata madagascariensis*] | AAF36092.1 | GPGSGGSYYPSSRVPDMVNGIMSAMQ GSGFNYOMFGNMLSQYSSGSGSCNPN NVNVLMDALLAALHCLSNHGSSSFAPS PTPAAMSAYSNSVGRMFAY | 4 | 29 |
| MaSp2(Lg) | major ampullate spidroin 2 [*Latrodectus geometricus*] | AAK30604.1 | SAASALSSPTTHARISSHASTLLSSGPTNS AAISNVISNAVSQVSASNPGSSSCDVLV QALLELITALISIVDSSNIGQVNYGSSGQY AQMVG | 4 | 30 |
| MaSp1(Lg) | major ampullate spidroin 1 [*Latrodectus geometricus*] | AAK30602.1 | AAASALAAPATSARISSHASTLLSNGPTN PASISNVISNAVSQISSSNPGASSCDVLV QALLELVTALLTIIGSSNVGNVNYDSSGQ YAQVVSQSVQNAFV | 4 | 31 |
| ADF1(Ad) | fibroin-1 [*Araneus diadematus*] | | GAVNRLSSAGAASRVSSNVAAIASAGA AALPNVISNIYSGVLSSGVSSSEALIQALL EVISALIHVLGSASIGNVSSVGVNSALNA VQNAVGAYAG | 4 | 32 |
| MaSp1(at) | *Argiope trifasciata* MaSp1 | AF350266 | SRLSSPGAASRVSSAVTSLVSSGGPTNSA ALSNTISNVVSQISSSNPGLSGCDVLVQA LLEIVSALVHILGSANIGQVNSSGVGRSA SIVGQSINQAFS | 5 | 33 |

TABLE 1-continued

Exemplary spidroin CT domains

| Desig-nation | Species and Spidroin | Genbank accession no | AA sequence | No. charged residues (K/R/E/D) | SEQ ID NO |
|---|---|---|---|---|---|
| MaSp1(Cm) | *Cyrtophora moluccensis* MaSp1 | AY666062 | SHLSSPEASSRVSSAVSNLVSSGSTNSAA LPNTISNVVSQISSSNPGLSGCDVLVQAL LEVVSALIHILGSSSIGQVNYGSAGQATQ IV | 4 | 34 |
| MaSp1(Nim) | *Nephila inaurata madagascariensis* MaSp1 | AF350277 | SRLSSPQASSRVSSAVSNLVASGPTNSA ALSSTISNAVSQIGASNPGLSGCDVLIQA LLEVVSALIHILGSSSIGQVNYGSAGQAT Q | 4 | 35 |
| MaSp2 (Aam) | *Argiope amoena* MaSp2 | AY365016 | RLSSPQASSRVSSAVSTLVSSGPTNPASL SNAIGSVVSQVSASNPGLPSCDVLVQAL LEIVSALVHILGSSSIGQINYSASSQYARL VGQSIAQALG | 5 | 36 |
| MaSp2(Aau) | *Argiope aurantia* MaSp2 | AF350263 | SRLSSPQASSRVSSAVSTLVSSGPTNPAA LSNAISSVVSQVSASNPGLSGCDVLVQA LLELVSALVHILGSSSIGQINYAAS | 4 | 37 |
| MaSp2(At) | *Argiope trifasciata* MaSp2 | AF350267 | SRLSSPQASSRVSSAVSTLVSSGPTNPAS LSNAISSVVSQVSSSNPGLSGCDVLVQA LLEIVSALVHILGSSSIGQINYAASSQYAQ LVGQSLTQALG | 4 | 38 |
| MaSp2(Gm) | *Gasteracantha mammosa* MaSp2 | AF350272 | SRLSSPQAGARVSSAVSALVASGPTSPA AVSSAISNVASQISASNPGLSGCDVLVQ ALLEIVSALVSILSSASIGQINYGASGQYA AMI | 4 | 39 |
| ADF-2 | *Araneus diadematus* fibroin-2 | ADU47854 | SRLSSPSAAARVSSAVSLVSNGGPTSPA ALSSSISNVVSQISASNPGLSGCDILVQAL LEIISALVHILGSANIGPVNSSSAGQSASI VGQSVYRALS | 5 | 40 |
| ADF-3 | *Araneus diadematus* fibroin-3 | ADU47855 | SRLSSPAASSRVSSAVSLVSSGPTKHAA LSNTISSVVSQVSASNPGLSGCDVLVQA LLEVVSALVSILGSSSIGQINYGASAQYT QMVGQSVAQALA | 4 | 41 |
| MaSp2a Ds | MaSp2a [*Deinopis spinosa*] | ABD61593.1 | SAVSRMSTPGSGSRISNAVSNILSSGVSS SSGLSNAISNISSSISASNPGLSGCDVLVQ VLLEVISALVHILGSASVGQVGSSPQNA QMVAANAVANAFS | 4 | 42 |
| MaSp2b ds | MaSp2b [*Deinopis spinosa*] | ABD61594.1 | SAVSRMSTPGSGSRISNAVSNILSSGVSS SSGLSNVISNLSSSISTSNPGLSGCDVLV QVLLEVISALVHILSSASLGQVGSSPQNA QMVAANAVANAFS | 4 | 43 |
| MiSp(Mg) | minor ampullate spidroin [*Metepeira grandiosa*] | ADM14320.1 | GAVNRLSSAEAASRVSSNVAALASGGP AALANVMGNIYSGVASSGVSSGEALVQ ALLEVISALVHLLSNASIGNVSSAGLGNT MSLVQSTVGAYAG | 5 | 44 |
| MiSp(Lh) | minor ampullate spidroin [*Latrodectus hesperus*] | ADM14322.1 | SAASRLSSPSSSSRISSAASSLATGGVLNS AALPSVVSNMMSQVSASSPGMSSSEV VIQALLELVSSLIHILSSANIGQVDFNSVG NTAAVVGQSLGAALG | 5 | 45 |
| MaSp2(Nc) | major ampullate spidroin 2 [*Nephila clavipes*] | AAT75313.1 | AAASRLASPDSGARVASAVSNLVSSGPT SSAALSSVISNAVSQIGASNPGLSGCDVL IQALLEIVSACVTILSSSSIGQVNYGAASQ FAQVVGQSVLSAF | 5 | 46 |

TABLE 1-continued

Exemplary spidroin CT domains

| Designation | Species and Spidroin | Genbank accession no | AA sequence | No. charged residues (K/R/E/D) | SEQ ID NO |
|---|---|---|---|---|---|
| MaSp2(Nim) | major ampullate spidroin 2 [*Nephila inaurata madagascariensis*] | AAK30607.1 | AAASRLASPDSGARVASAVSNLVSSGPT SSAALSSVISNAVSQIGASNPGLSGCDVL IQALLEIVSACVTILSSSIGQVNYGAA | 5 | 47 |
| MiSp-like(Lh) | minor ampullate spidroin 1-like protein [*Latrodectus hesperus*] | ACB29694.1 | SAASRLSSPSSSSRISSAASSLATGGVLNS AALPSVVSNIMSQVSASSPGMSSSEVVI QALLELVSSLIHILSSANIGQVDFNSVGN TAAVVGQSLGAALG | 5 | 48 |
| Consensus | MaSP consensus (SEQ ID NO: 9 in WO2010/1234 50 | | SRLSSPQASSRVSSAVSNLVSSGPTNSAA LSNTISNVVSQISASNPGLSGCDVLVQAL LEVVSALVHILGSSSIGQVNYGSAGQAT QIVGQSVAQALGEF | 5 | 49 |
| MaSp1(Mh) | *Macrothele holsti* MaSp1 | AY666068 | SHLSSPEASSRVSSAVSNLVSGGSTNSAA LPNTISNVVSQISSSNPGLSGCDVLVQAL LEVVSALIHILGSSSIGQVDYGSAGQATQ IVGQSA | 5 | 50 |
| MaSp1(Np) | *Nephila pilipes* MaSp1 | AY666076 | SRLSSPEASSRVSSAVSNLVSSGPTNSAA LSNTISNVVSQISSSNPGLSGCDVLVQAL LEWSALIHILGSSSIGQVNYGSAGQATQ IV | 5 | 51 |
| MaSp1(Ov) | *Octonoba varians* MaSp1 | AY666057 | SRLSSPEASSRVSSAVSNLVSSGPTNSAA LSNTISNVVSQISSSNPGLSGCDVLVQAL LEVVSAPIHILGSSSIGQVNYGSAGQATQ IV | 5 | 52 |
| MaSp1(Ps) | *Psechrus sinensis* MaSp1 | AY666064 | SRLSSPEASSRVSSAVSNLVSSGPTNSAA LPNTISNVVSQISSSNPGLSGCDVLVQAL LEVVSALIHILGSSSIGQVNYGSAGQATQ IV | 5 | 53 |
| MaSp(Tv) | *Tetragnatha versicolor* MaSp1 | AF350286 | SRLSSPASNARISSAVSALASGGASSPGY LSSIISNVVSQVSSNNDGLSGCDTVVQA LLEVAAALVHVLASSNIGQVNLNTAGYT SQL | 5 | 54 |
| MaSp2(Ns) | *Nephila senegalensis* MaSp2 | AF350280 | SRLASPDSGARVASAVSNLVSSGPTSSA ALSSVIXNAVSQIGASNPGLSGCDVLIXA LLEIVSACVTILSSSIGQVNYGAA | 5 | 55 |
| ADF-4 | *Araneus diadematus* fibroin-4 | ADU47856 | SVYLRLQPRLEVSSAVSSLVSSGPTNGAA VSGALNSLVSQISASNPGLSGCDALVQA LLELVSALVAILSSASIGQVNVSSVSQSTQ MISQALS | 5 | 56 |
| MaSp(Aap) | major ampullate spidroin [*Agelenopsis aperta*] | AAT08436.1 | NSVSRLSSPSSSSRVSSAVSGLLPNGNFN LGNLPGIVSNLSSSIASSGLSGCENLVQV LIEVVSALVHILGSANIGNINMNAASSTA AAVGQAIVNGLY | 4 | 57 |
| TuSp1(Aar) | tubuliform spidroin 1 [*Argiope argentata*] | AAY28932.1 | ASSSGLGSSAASARVSSLANSVASAISSS GGSLSVPTFLNFLSSVGAQVSSSSSLNSS EVTNEVLLEAIAALLQVLNGAQITSVNLR NVPNAQQALVQALSG | 5 | 58 |

TABLE 1-continued

Exemplary spidroin CT domains

| Desig-nation | Species and Spidroin | Genbank accession no | AA sequence | No. charged residues (K/R/E/D) | SEQ ID NO |
|---|---|---|---|---|---|
| CThyb_Esp | Artificial from WO2010/1234 50 | | SRLSSPEASSRVSSAVSNLVSSGPTNSAA LSSTISNVVSQIGASNPGLSGCDVLVQAL LEVVSALIHILGSSSIGQVNYGSAGQATQ LVGQSVYQALGEF | 6 | 59 |
| MaSp1(Ns) | *Nephila senegalensis* major ampullate spidroin 1 (MaSp1) | AF350279 | SRLSSPEASSRVSSAVSNLVSSGPTNSAA LSSTISNVVSQIGASNPGLSGCDVLIQAL LEVVSALVHILGSSSIGQVNYGSAGQAT Q | 5 | 60 |
| Fib2(Dt) | *Dolomedes tenebrosus* Fib2 | AF350270 | SRLSSPQAASRVSSAVSSLVSNGQVNVA ALPSIISSLSSSISASSTAASDCEVLVQVLL EIVSALVQIVSSANVGYINPEASGSLNAV GSALAAAMG | 6 | 61 |
| MiSp(Ud) | MiSp [*Uloborus diversus*] | ABD61597.1 | AASNRIVSAPAVNRMSAASSTLVSNGA FNVGALGSTISDMAAQIQAGSQGLSSA EATVQALLEVISVLTHMLSSANIGYVDFS RVGDSASAVSQSMAYAG | 8 | 62 |
| CySp1(Ab) | egg case silk protein 1 [*Argiope bruennichi*] | BAE86855.1 | VSSSGLGSSAATARVSSLANSFASAISSS GGSLSVPTFLNLLSSVGAQVSSSSSLSSLE VTNEVLLEAIAALLQVINGGSITSVDLRY VPNAQQDLVNALSG | 7 | 63 |
| MiSp(Av) | minor ampullate spidroin [*Araneus ventricosus*] | AFV31615.1 | GAVNRLSSAEAASRVSSNIAAIASGGAS ALPSVISNIYSGVVASGVSSNEALIQALLE LLSALVHVLSSASIGNVSSVGVDSTLNVV QDSVGQYVG | 7 | 64 |
| MiSp1(Nc) | minor ampullate silk protein MiSp1 [*Nephila clavipes*] | AAC14589.1 | STTSRLSSAEASSRISSAASTLVSGGYLNT AALPSVISDLFAQVGASSPGVSDSEVLIQ VLLEIVSSLIHILSSSSVGQVDFSSVGSSA AAVGQSMQVVMG | 8 | 65 |
| Fib1(Dt) | *Dolomedes tenebrosus* Fib1 | AF350269 | SRLSSPEAASRVSSAVSSLVSNGQVNVD ALPSIISNLSSSISASATTASDCEVLVQVLL EVVSALVQIVCS | 7 | 66 |
| TuSp1(Aap) | tubuliform spidroin 1 [*Agelenopsis aperta*] | ADM14323.1 | SSETGLSSASASSRVNSLASSVASAIASG QALSADSFAKSLLIQASQIQSSAPSFKAD DVVHESLLEGISALIQVINSSYGSPLSLSN AQTVNAGLVNYFLV | 9 | 67 |
| CySp1(Ncl) | cylindrical silk protein 1 [*Nephila clavata*] | BAE54450.1 | LSSSGLSSASASARVGSLAQSLASALSTS RGTLSLSTFLNLLSPISSEIRANTSLDGTQ ATVEALLEALAALLQVINGAQITDVNVSS VPSVNAALASALVA | 8 | 68 |
| TuSp1(Lh) | egg case fibroin [*Latrodectus hesperus*] | ADV40181.1 | LSPAGLASTAATSRINDIAQSLSSTLSSGS QLAPDNVLPGLIQLSSSIQSGNPDLDPA GVLIESLLEYTSALLALLQNAQITTYDAAT LPAFNTALVNYLVPLV | 8 | 69 |
| MiSp(Aar) | minor ampullate spidroin [*Argiope argentata*] | AFM29836.1 | SVSRLSSAEAVSRVSSNIGAIASGGASAL PGVISNIFSGVSASAGSYEEAVIQSLLEVL SALLHILSNSSIGYVGADGLTDSLAVVQQ AMGPVVG | 8 | 70 |
| MiSp1(Na) | minor ampullate fibroin 1 [*Nephila antipodiana*] | ABC72645.1 | STTSRLSTAEASSRISTAASTLVSGGYLNT AALPSVIADLFAQVGASSPGVSDSEVLIQ VLLEIVSSLIHILSSSSVGQVDFSSVGSSA AAVGQSMQVVMG | 8 | 71 |

TABLE 1-continued

Exemplary spidroin CT domains

| Desig- nation | Species and Spidroin | Genbank accession no | AA sequence | No. charged residues (K/R/E/D) | SEQ ID NO |
|---|---|---|---|---|---|
| MiSp(Nc) | minor ampullate silk protein [*Nephila clavipes*] | AAC14590.1 | STTSRLSSAEACSRISAAASTLVSGSLNTA ALPSVISDLFAQVSASSPGVSGNEVLIQV LLEIVSSLIHILSSSSVGQVDFSSVGSSAA AVGQSMQVVMG | 7 | 72 |
| MiSp(Ds) | *Deinopis spinosa* MiSp | ABD61589 | ASTSRLASGQATDRVKDVVSTLVSNGIN GDALSNAISNVMTQVNAAVPGLSFCER LIQVLLEIVAALVHILSSSNVGSIDYGSTSR TAIGVSNALASAVAGAF | 11 | 73 |

The CT domain typically consists of from 70 to 120 amino acid residues. It is preferred that the CT domain contains at least 70, or more than 80, preferably more than 90, amino acid residues. It is also preferred that the CT domain contains at most 120, or less than 110 amino acid residues, more preferably less than 100 residues. A typical preferred CT domain contains approximately 87-97 amino acid residues.

Properties of the REP Domain

It is contemplated that the specific sequence or organization of the REP domain is not critical to the present invention as long as the REP-domain is capable of polymerization, and that a wide variety of spider silk REP-domains would be suitable for the present protein. In Rising et al. (Cell. Mol. Life Sci. (2011) 68:169-184), several REP-domains used in the art in recombinant spidroins are discussed, and it is contemplated that a REP-domain based on teachings therein would be useful in the present context.

In general terms, the REP domain has a repetitive character, preferably alternating between alanine-rich stretches (A-segments) and glycine-rich stretches (G-segments).

The REP domain of the present invention may comprise alanine-rich A-segments and glycine-rich G-segments, wherein the sum of the number of A segments and the number of G segments in the REP-domain is 3 to 30, preferably 4-20, more preferably 4-10, most preferably 4-8.

The REP domain may comprise alanine-rich A-segments and glycine-rich G-segments, wherein each A segment is an amino acid sequence of from 8 to 20 amino acid residues, wherein at least 60%, preferably at least 65%, more preferably at least 70%, most preferably at least 75% of the amino acid residues are Ala.

The REP domain may comprise alanine-rich A-segments and glycine-rich G-segments, wherein each G segment is an amino acid sequence of from 12 to 40 amino acid residues, wherein at least 30%, preferably at least 35%, most preferably at least 40% of the amino acid residues are Gly.

The REP domain may comprise alanine-rich A-segments and glycine-rich G-segments, wherein each A segment contains at least one stretch of 5 consecutive, preferably 6 consecutive A residues. The REP domain may comprise alanine-rich A-segments and glycine-rich G-segments, wherein each G segment contains at least one, preferably at least two GGX motif(s), where X designates any amino acid.

The REP-domain may comprise 40-600, preferably 50-500, more preferably 60-400, most preferably 70-300 amino acids.

The REP domain generally contains more than 30, such as more than 70, and less than 600, preferably less than 300, such as less than 240, amino acid residues, and can itself be divided into several L (linker) segments, A (alanine-rich) segments and G (glycine-rich) segments, as will be explained in more detail below. Typically, said linker segments, which are optional, are located at the REP domain terminals, while the remaining segments are in turn alanine-rich and glycine-rich. Thus, the REP domain can generally have either of the following structures, wherein n is an integer:

$L(AG)_nL$, such as $LA_1G_1A_2G_2A_3G_3A_4G_4A_5G_5L$;

$L(AG)_nAL$, such as $LA_1G_1A_2G_2A_3G_3A_4G_4A_5G_5A_6L$;

$L(GA)_nL$, such as $LG_1A_1G_2A_2G_3A_3G_4A_4G_5A_5L$; or $L(GA)N_{GL}$, such as $LG_1A_1G_2A_2G_3A_3G_4A_4G_5A_5G_6L$.

It follows that it is not critical whether an alanine-rich or a glycine-rich segment is adjacent to the N-terminal or C-terminal linker segments. It is preferred that n is an integer from 2 to 10, preferably from 2 to 8, preferably from 4 to 8, more preferred from 4 to 6, i.e. n=4, n=5 or n=6.

The alanine content of the REP domain according to the invention may be above 20%, preferably above 25%, more preferably above 30%, and below 50%, preferably below 40%, more preferably below 35%. This is advantageous, since it is contemplated that a higher alanine content provides a stiffer and/or stronger and/or less extendible fiber.

The REP domain is preferably void of proline residues, i.e. there are no Pro residues in the REP domain.

Now turning to the segments that constitute the REP domain according to the invention, it shall be emphasized that each segment is individual, i.e. any two A segments, any two G segments or any two L segments of a specific REP domain may be identical or may not be identical. Thus, it is not a general feature of the invention that each type of segment is identical within a specific REP domain. Rather, the following disclosure provides the skilled person with guidelines how to design individual segments and gather them into a REP domain, which is a part of a functional spider silk protein according to the invention.

Each individual A segment is an amino acid sequence having from 8 to 18 amino acid residues. It is preferred that each individual A segment contains from 13 to 15 amino acid residues. It is also possible that a majority, or more than two, of the A segments contain from 13 to 15 amino acid residues, and that a minority, such as one or two, of the A segments contain from 8 to 18 amino acid residues, such as 8-12 or 16-18 amino acid residues. A vast majority of these amino acid residues are alanine residues. More specifically, from 0 to 3 of the amino acid residues are not alanine residues, and the remaining amino acid residues are alanine residues. Thus, all amino acid residues in each individual A segment are alanine residues, with no exception or the exception of one, two or three amino acid residues, which can be any amino acid. It is preferred that the alanine-replacing amino acid(s) is (are) natural amino acids, preferably individually selected from the group of serine, glutamic acid, cysteine and glycine, more preferably serine. Of course, it is possible that one or more of the A segments are all-alanine segments, while the remaining A segments contain 1-3 non-alanine residues, such as serine, glutamic acid, cysteine or glycine.

Each A segment may contain 13-15 amino acid residues, including 10-15 alanine residues and 0-3 non-alanine residues as described above. More preferably, each A segment contains 13-15 amino acid residues, including 12-15 alanine residues and 0-1 non-alanine residues as described above.

It is preferred that each individual A segment has at least 80%, preferably at least 90%, more preferably 95%, most preferably 100% identity to an amino acid sequence selected from the group of amino acid residues 7-19, 43-56, 71-83, 107-120, 135-147, 171-183, 198-211, 235-248, 266-279, 294-306, 330-342, 357-370, 394-406, 421-434, 458-470, 489-502, 517-529, 553-566, 581-594, 618-630, 648-661, 676-688, 712-725, 740-752, 776-789, 804-816, 840-853, 868-880, 904-917, 932-945, 969-981, 999-1013, 1028-1042 and 1060-1073 of SEQ ID NO: 3. Each sequence of this group corresponds to a segment of the naturally occurring sequence of *Euprosthenops australis* MaSp1 protein, which is deduced from cloning of the corresponding cDNA, see WO 2007/078239. Alternatively, each individual A segment has at least 80%, preferably at least 90%, more preferably 95%, most preferably 100% identity to an amino acid sequence selected from the group of amino acid residues 143-152, 174-186, 204-218, 233-247 and 265-278 of SEQ ID NO: 3. Each sequence of this group corresponds to a segment of expressed, non-natural spider silk proteins according to the invention, which proteins have capacity to form silk fibers under appropriate conditions. Thus, in certain embodiments according to the invention, each individual A segment is identical to an amino acid sequence selected from the above-mentioned amino acid segments. Without wishing to be bound by any particular theory, it is envisaged that A segments according to the invention form helical structures or beta sheets.

Throughout this description, alternative embodiments according to the invention fulfil, instead of the specified percentage of identity, the corresponding percentage of similarity. Other alternative embodiments fulfil the specified percentage of identity as well as another, higher percentage of similarity, selected from the group of preferred percentages of identity for each sequence. For example, a sequence may be 70% similar to another sequence; or it may be 70% identical to another sequence; or it may be 70% identical and 90% similar to another sequence.

Furthermore, it has been concluded from experimental data that each individual G segment is an amino acid sequence of from 12 to 30 amino acid residues. It is preferred that each individual G segment consists of from 14 to 23 amino acid residues. At least 40% of the amino acid residues of each G segment are glycine residues. Typically, the glycine content of each individual G segment is in the range of 40-60%.

It is preferred that each individual G segment has at least 80%, preferably at least 90%, more preferably 95%, most preferably 100% identity to an amino acid sequence selected from the group of amino acid residues 20-42, 57-70, 84-106, 121-134, 148-170, 184-197, 212-234, 249-265, 280-293, 307-329, 343-356, 371-393, 407-420, 435-457, 471-488, 503-516, 530-552, 567-580, 595-617, 631-647, 662-675, 689-711, 726-739, 753-775, 790-803, 817-839, 854-867, 881-903, 918-931, 946-968, 982-998, 1014-1027, 1043-1059 and 1074-1092 of SEQ ID NO: 3. Each sequence of this group corresponds to a segment of the naturally occurring sequence of *Euprosthenops australis* MaSp1 protein, which is deduced from cloning of the corresponding cDNA, see WO 2007/078239. Alternatively, each individual G segment has at least 80%, preferably at least 90%, more preferably 95%, most preferably 100% identity to an amino acid sequence selected from the group of amino acid residues 153-173, 187-203, 219-232, 248-264 and 279-296 of SEQ ID NO: 3. Each sequence of this group corresponds to a segment of expressed, non-natural spider silk proteins according to the invention, which proteins have capacity to form silk fibers under appropriate conditions. Thus, each individual G segment may preferably be identical to an amino acid sequence selected from the above-mentioned amino acid segments.

The first two amino acid residues of each G segment according to the invention are preferably not -Gln-Gln-.

There are the three subtypes of the G segment according to the invention. This classification is based upon careful analysis of the *Euprosthenops australis* MaSp1 protein sequence (WO 2007/078239), and the information has been employed and verified in the construction of non-natural spider silk proteins.

The first subtype of the G segment according to the invention is represented by the amino acid one letter consensus sequence GQG(G/S)QGG(Q/Y)GG (L/Q)GQG-GYGQGA GSS (SEQ ID NO: 4). This first, and generally the longest, G segment subtype typically contains 23 amino acid residues, but may contain as little as 17 amino acid residues, and lacks charged residues or contain one charged residue. Thus, it is preferred that this first G segment subtype contains 17-23 amino acid residues, but it is contemplated that it may contain as few as 12 or as many as 30 amino acid residues. Without wishing to be bound by any particular theory, it is envisaged that this subtype forms coil structures or $3_1$-helix structures. Representative G segments of this first subtype are amino acid residues 20-42, 84-106, 148-170, 212-234, 307-329, 371-393, 435-457, 530-552, 595-617, 689-711, 753-775, 817-839, 881-903, 946-968, 1043-1059 and 1074-1092 of SEQ ID NO: 3. The first two amino acid residues of each G segment of this first subtype according to the invention are preferably not -Gln-Gln-.

The second subtype of the G segment according to the invention is represented by the amino acid one letter consensus sequence GQGGQGQG(G/R)Y GQG(A/S)G(S/G)S (SEQ ID NO: 5). This second, generally mid-sized, G segment subtype typically contains 17 amino acid residues and lacks charged residues or contain one charged residue. It is preferred that this second G segment subtype contains 14-20 amino acid residues, but it is contemplated that it may contain as few as 12 or as many as 30 amino acid residues. Without wishing to be bound by any particular theory, it is envisaged that this subtype forms coil structures. Representative G segments of this second subtype are amino acid residues 249-265, 471-488, 631-647 and 982-998 of SEQ ID NO: 3; and amino acid residues 187-203 of SEQ ID NO: 3.

The third subtype of the G segment according to the invention is represented by the amino acid one letter consensus sequence G(R/Q)GQG(G/R)YGQG (A/S/V)GGN (SEQ ID NO: 6). This third G segment subtype typically contains 14 amino acid residues, and is generally the shortest of the G segment subtypes according to the invention. It is preferred that this third G segment subtype contains 12-17 amino acid residues, but it is contemplated that it may contain as many as 23 amino acid residues. Without wishing to be bound by any particular theory, it is envisaged that this subtype forms turn structures. Representative G segments of this third subtype are amino acid residues 57-70, 121-134, 184-197, 280-293, 343-356, 407-420, 503-516, 567-580, 662-675, 726-739, 790-803, 854-867, 918-931, 1014-1027 of SEQ ID NO: 3; and amino acid residues 219-232 of SEQ ID NO: 3.

Thus, each individual G segment preferably has at least 80%, more preferably 90%, yet more preferably 95%, most preferably 100% identity to an amino acid sequence selected from SEQ ID NO: 4, SEQ ID NO: 5 and SEQ ID NO: 6.

It is preferred that the alternating sequence of A and G segments of the REP domain, every second G segment is of the first subtype, while the remaining G segments are of the third subtype, e.g. $A_1 G_{short} A_2 G_{long} A_3 G_{short} A_4 G_{long} A_5 G_{short} \cdots$ Alternatively, it is preferred that the REP domain, one G segment of the second subtype interrupts the G segment regularity via an insertion, e.g. $A_1 G_{short} A_2 G_{long} A_3 G_{mid} A_4 G_{short} A_5 G_{long} \cdots$ Each individual L segment represents an optional linker amino acid sequence, which may contain from 0 to 30 amino acid residues, preferably 0-25 amino-acid residues, such as from 0 to 10 amino acid residues. While this segment is optional and not functionally critical for the spider silk protein, its presence still allows for fully functional spider silk proteins, forming spider silk fibers according to the invention. There are also linker amino acid sequences present in the repetitive part (SEQ ID NO: 3) of the deduced amino acid sequence of the MaSp1 protein from *Euprosthenops australis*. In particular, the amino acid sequence of a linker segment may resemble any of the described A or G segments, but usually not sufficiently to meet their criteria as defined herein.

As shown in WO 2007/078239, a linker segment arranged at the C-terminal part of the REP domain can be represented by the amino acid one letter consensus sequences ASASAAASAASTVANSVS (SEQ ID NO: 7) and ASAASAAA (SEQ ID NO: 8), which are rich in alanine. In fact, the second sequence can be considered to be an A segment according to the invention, while the first sequence has a high degree of similarity to A segments according to the invention. Another example of a linker segment according the invention has the one letter amino acid sequence GSAMGQGS (SEQ ID NO: 9), which is rich in glycine and has a high degree of similarity to G segments according to the invention. Another example of a linker segment is SASAG (SEQ ID NO: 10). Yet further example of a linker segment is VTSGGYGYGTSAAAGAGVAAGSYA (part of SEQ ID NO: 11) derived from *A. ventricosus* MiSP CT protein, see Example 1.

Representative L segments are amino acid residues 1-6 and 1093-1110 of SEQ ID NO: 3; and amino acid residues 138-142 of SEQ ID NO: 3, but the skilled person in the art will readily recognize that there are many suitable alternative amino acid sequences for these segments. In the REP domain according to the invention, one of the L segments may contain 0 amino acids, i.e. one of the L segments is void. In the REP domain according to the invention, both L segments may contain 0 amino acids, i.e. both L segments are void. Thus, these embodiments of the REP domains according to the invention may be schematically represented as follows: $(AG)_n L$, $(AG)_n AL$, $(GA)_n L$, $(GA)_n GL$; $L(AG)_n$, $L(AG)_n A$, $L(GA)_n$, $L(GA)_n G$; and $(AG)_n$, $(AG)_n A$, $(GA)_n$, $(GA)_n G$. Any of these REP domains are suitable for use with any CT domain as defined above.

It is preferable that n is 2 or 4. The selected REP domain is preferably $LG(AG)_2 L$ or $LG(AG)_4 L$. Most preferably, the selected REP domain is $LG(AG)_2 L$.

The spider silk protein may comprise a set of domains according to the formula NTL-REP-L-CT, wherein each individual L segment is a linker amino acid sequence of from 1 to 30, preferably 1-25 amino acid residues.

It is preferable that the REP domain consists of a sequence of 30-600, more preferably 50-500, most preferably 70 to 300 amino acid residues.

Properties of the Optional NT Domain

It is preferable that the optional NT domain is present. Needless to say, the following definitions of NT are only relevant in situations where the NT domain is actually present.

The NT domain has a high degree of similarity to the N-terminal amino acid sequence of spider silk proteins. As shown in FIG. 1, this amino acid sequence is well conserved among various species and spider silk proteins, including MaSp1 and MaSp2. In FIG. 1, the following spidroin NT domains are aligned, denoted with GenBank accession entries where applicable:

TABLE 2

| Exemplary spidroin NT domains | | | SEQ |
|---|---|---|---|
| Designation | Species and spidroin protein | GenBank acc. no. | ID NO: |
| Ea MaSp1 | *Euprosthenops australis* MaSp 1 | AM259067 | 80 |
| Lg MaSp1 | *Latrodectus geometricus* MaSp 1 | ABY67420 | 81 |
| Lh MaSp1 | *Latrodectus hesperus* MaSp 1 | ABY67414 | 82 |
| Nc MaSp1 | *Nephila clavipes* MaSp 1 | ACF19411 | 83 |
| At MaSp2 | *Argiope trifasciata* MaSp 2 | AAZ15371 | 84 |
| Lg MaSp2 | *Latrodectus geometricus* MaSp 2 | ABY67417 | 85 |
| Lh MaSp2 | *Latrodectus hesperus* MaSp 2 | ABR68855 | 86 |
| Nim MaSp2 | *Nephila inaurata madagascariensis* MaSp 2 | AAZ15322 | 87 |
| Nc MaSp2 | *Nephila clavipes* MaSp 2 | ACF19413 | 88 |
| Ab CySp1 | *Argiope bruennichi* cylindriform spidroin 1 | BAE86855 | 89 |
| Ncl CySp1 | *Nephila clavata* cylindriform spidroin 1 | BAE54451 | 90 |
| Lh TuSp1 | *Latrodectus hesperus* tubuliform spidroin | ABD24296 | 91 |
| Nc Flag | *Nephila clavipes* flagelliform silk protein | AF027972 | 92 |
| Nim Flag | *Nephila inaurata madagascariensis* flagelliform silk protein | AF218623 (translated) | 93 |

Only the part corresponding to the N-terminal fragment is shown for each sequence, omitting the signal peptide. Nc flag and Nlm flag are translated and edited according to Rising A. et al. Biomacromolecules 7, 3120-3124 (2006)).

It is not critical which specific NT domain is present in spider silk proteins according to the invention. Thus, the NT domain according to the invention can be selected from any of the amino acid sequences shown in Table 2 or sequences with a high degree of similarity. A wide variety of N-terminal sequences can be used in the spider silk protein according to the invention. Based on the homologous sequences of FIG. 1, the following sequence constitutes a consensus NT amino acid sequence:

```
                                             (SEQ ID NO: 2)
QANTPWSSPNLADAFINSF(M/L)SA(A/I)SSSGAFSADQ

LDDMSTIG(D/N/Q)TLMSAMD(N/S/K)MGRSG(K/R)ST
```

-continued

KSKLQALNMAFASSMAEIAAAESGG(G/Q)SVGVKTNAISD

ALSSAFYQTTGSVNPQFV(N/S)EIRSLI(G/N)M(F/L)

(A/S)QASANEV.

The sequence of the NT domain according to the invention may have at least 50% identity, preferably at least 60% identity, to the consensus amino acid sequence SEQ ID NO: 2, which is based on the amino acid sequences of FIG. 1. Preferably, the sequence of the NT domain according to the invention has at least 65% identity, more preferably at least 70% identity, to the consensus amino acid sequence SEQ ID NO: 2. More preferably, the NT domain according to the invention has furthermore 70%, most preferably 80%, similarity to the consensus amino acid sequence SEQ ID NO: 2.

A representative NT domain according to the invention is the *Euprosthenops australis* sequence SEQ ID NO: 1. Preferably, the NT domain has at least 80% identity to SEQ ID NO: 1 or any individual amino acid sequence in Table 2. More preferably, the NT domain has at least 90%, such as at least 95% identity, to SEQ ID NO: 1 or any individual amino acid sequence in Table 2. Most preferably, the NT domain is identical to SEQ ID NO: 1 or any individual amino acid sequence in Table 2, in particular to Ea MaSp1.

The NT domain contains from 100 to 160 amino acid residues. It is preferred that the NT domain contains at least 100, or more than 110, preferably more than 120, amino acid residues. It is also preferred that the NT domain contains at most 160, or less than 140 amino acid residues. A most preferred NT domain contains approximately 130-140 amino acid residues.

When the N-terminal part of the spider silk protein contains two or more domains (NT) derived from the N-terminal domain of a spider silk protein, it may also contain one or more linker peptides. The linker peptide(s) may be arranged between two NT domains and provide a spacer.

Properties and Features of the Chimeric Spider Silk Protein

Preferably, the recombinant spider silk protein exhibits highly pH-dependent solubility, more preferably highly pH-dependent solubility defined as least 10 times, preferably 50 times, more preferably 100 times higher solubility in aqueous 20 mM Tris-HCl pH8.0 buffer than in aqueous 500 mM Na-acetate, 200 mM NaCl at pH5.0.

Preferably, the recombinant spider silk protein is soluble in aqueous 20 mM Tris-HCl pH8.0 buffer at a concentration of 100 mg/ml, more preferably 200 mg/ml, most preferably 300 mg/ml, and polymerizes in aqueous 500 mM Na-acetate, 200 mM NaCl at pH5.0.

Preferably, the protein according to the first aspect comprises a sequence having at least 80%, preferably at least 85%, more preferably at least 90%, yet more preferably at least 95% sequence identity to SEQ ID NO: 11. Most preferably, the recombinant spider silk protein of the first aspect consists of a sequence identical to SEQ ID NO: 11.

Preferably, the spider silk protein comprises no more than 600, preferably no more than 500, more preferably no more than 400, yet more preferably no more than 300, most preferably no more than 250 amino-acid residues in total. Smaller proteins are generally easier to produce recombinantly in high quantities.

Solutions of Chimeric Spider Silk Proteins

In a second aspect of the present invention, there is provided a non-denaturing solution of a spider silk protein according to any of the preceding claims, having a protein concentration of said spider silk protein of at least 100 mg/ml, preferably 150 mg/ml, most preferably 200 mg/ml. Needless to say, the non-denaturing solvent has a composition that does not lead to polymerization of said protein, notably with regards to pH, salt concentration and organic solvents. For instance, the solvent may be aqueous 20 mM Tris-HCl pH 8.0 buffer or the like. Preferably, the pH is 6.4 or above, such at 7.0 or above, preferably 7.5-8.5.

Polymers of Chimeric Spider Silk Proteins

In a third aspect, there is provided a polymer of a spider silk protein according to the first aspect. Said polymer may e.g. be a fiber, film, foam, net or mesh, preferably a fiber.

Said polymer may be a fiber having length of at least 10 cm, preferably at least 1 m, more preferably at least 5 m, yet more preferably at least 10 m, still more preferably at least 50 m, most preferably at least 100 m.

The diameter of the fiber may be 100 μm, preferably less than 50 μm, more preferably less than 20 μm, most preferably less than 10 μm.

The polymer may have toughness of ≥3 MJ/m³, preferably ≥10 MJ/m³, more preferably ≥20 MJ/m³, most preferably ≥40 MJ/m³. Preferably, the toughness refers to polymer that is as-spun. i.e. not subjected to post-stretching or similar after-treatment.

Methods for Producing a Polymer of Spider Silk Protein

In a fourth aspect, there is provided a method for producing a polymer of a spider silk protein, comprising the steps of:

a. providing a first liquid medium comprising a spider silk protein according to the first aspect in solution in said medium at a concentration of at least 100 mg/ml, preferably 200 mg/ml, most preferably 300 mg/ml;

b. adjusting the properties of the first liquid medium such that it allows polymerisation of said spider silk protein;

c. allowing the spider silk protein to form polymers; and d. isolating the spider silk protein polymers.

The properties of the first liquid medium may be adjusted by extruding the solution of a spider silk protein into a second fluid medium having properties that allow polymerisation of said spider silk protein.

The first liquid medium in step (a) preferably has a pH of at least 6.4.

The first liquid medium in step (a) preferably has a salt concentration of less than 100 mM.

The first liquid medium in step (a) is preferably an aqueous solution comprising less than 10% (v/v) of organic solvents.

The properties of the first liquid medium in steps (b)-(d) are preferably adjusted to pH 6.3 or below, in the presence of a sufficient salt concentration for polymerisation of said spider silk protein.

The properties of the first liquid medium in steps (b)-(d) may be adjusted to at least 100 mM salt concentration and to pH 6.3 or below.

The properties of the first liquid medium in steps (b)-(d) may be adjusted to having a concentration of an organic solvent sufficient to induce polymerization.

The second fluid medium may have pH 6.3 or below, and a sufficient salt concentration for polymerisation of said spider silk protein.

The second fluid medium may comprise an organic solvent at a concentration sufficient to induce polymerization.

The second fluid medium may comprise a hygroscopic polymer, such as PEG.

The extrusion may be through a capillary having an opening with a cross-sectional area in the interval 20-50000

$\mu m^2$, preferably 30-30000 $\mu m^2$, more preferably 40-10000 $\mu m^2$, yet more preferably 50-5000 $\mu m^2$, most preferably 70-800 $\mu m^2$.

The extrusion may be performed at a linear flow rate of 0.1-500 mm/s, more preferably 0.5-200 mm/s, most preferably 1-100 mm/s.

Preferably, the polymer is extruded in a 3D-printing apparatus to enable formation of a defined pattern.

Said polymer may form a fiber, film, foam, net or mesh, preferably a fiber.

The polymers may also be subjected to further treatments, for instance post-stretching in different aqueous buffers and/or alcohol baths, and/or dehydrating solutions such as polyethylene glycol (PEG).

DNA Sequences, Constructs, Host Cells, Methods of Manufacture

In a fifth aspect, there is provided a nucleic acid encoding for a protein according the first aspect.

In a sixth aspect, there is provided an expression vector comprising a nucleic acid according to the fifth aspect, operatively coupled to a promoter.

In a seventh aspect, there is provided a host cell comprising a nucleic acid according to the fifth aspect, or an expression vector according to the sixth aspect.

In an eighth aspect, there is provided a method of producing a recombinant spider silk protein, comprising:

a. Culturing a host cell according to the seventh aspect, in conditions allowing production of the protein;

b. Isolating said protein from said culture.

The spider silk protein according to the invention is typically recombinantly produced using a variety of suitable hosts, such as bacteria, yeast, mammalian cells, plants, insect cells, and transgenic animals. It is preferred that the spider silk protein according to the invention is produced in bacteria.

Uses of Spider Silk Protein

The recombinant spider silk protein and the polymers derived thereof discussed above are useful for any of the known applications for spider silk proteins.

In a ninth aspect, there is provided a use of a spider silk protein according to the first aspect, or a polymer according to the third aspect, in the manufacture of an implantable material or a cell culture scaffold.

In a tenth aspect, there is provided a use of a spider silk protein according to the first aspect, or a polymer according to the third aspect, as an implantable material or a cell culture scaffold.

General Aspects Relevant to Present Disclosure

The term "comprising" is to be interpreted as including, but not being limited to. All references are hereby incorporated by reference. The arrangement of the present disclosure into sections with headings and subheadings is merely to improve legibility and is not to be interpreted limiting in any way, in particular, the division does not in any way preclude or limit combining features under different headings and subheadings with each other.

EXAMPLES

The following examples are not to be regarded as limiting. For further information on the experimental details, the skilled reader is directed to a separate section titled Materials and Methods.

Example 1: Production of a Chimeric Minispidroin NT2RepCT

Figures 2A, 2B, 2C:
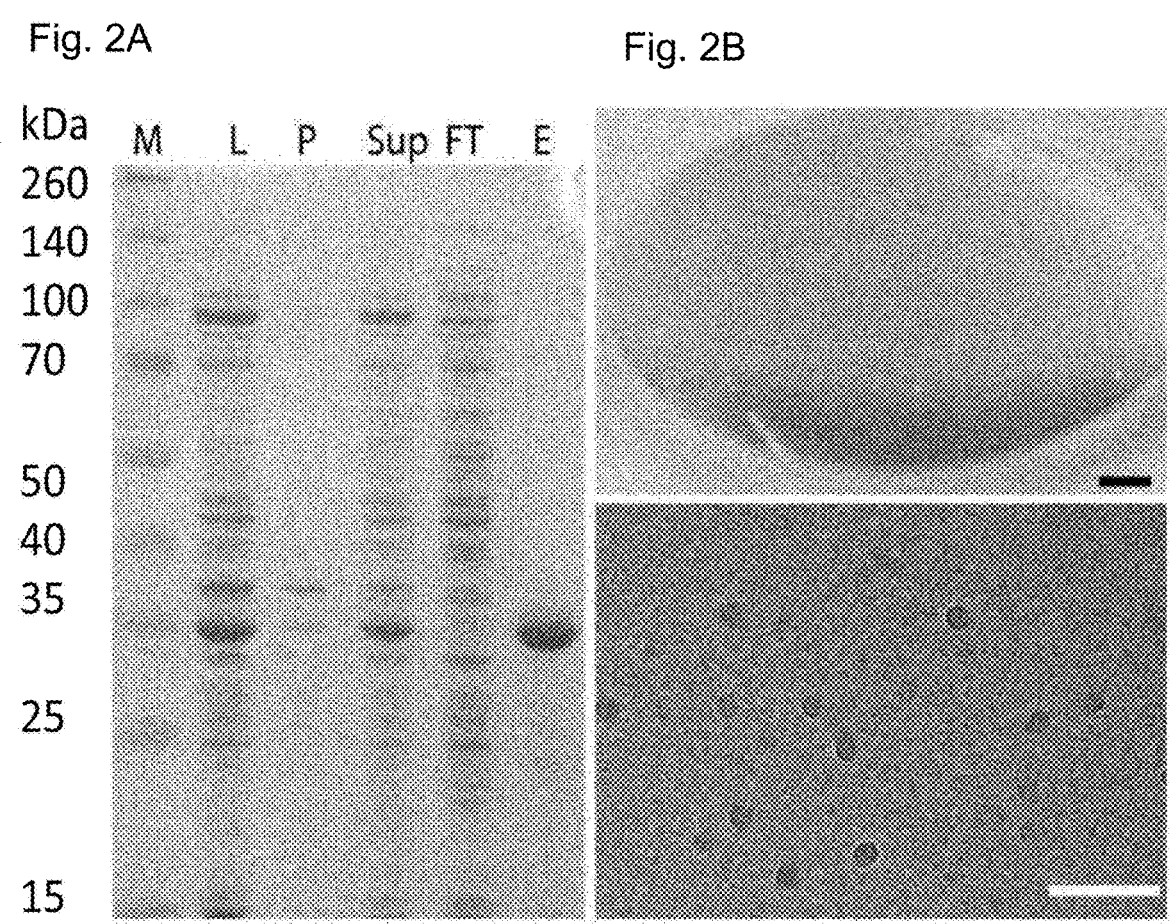
FIG. 2A: SDS-PAGE of purified NT2RepCT and different purification steps. M=Spectra Broadrange protein marker (sizes in kilodalton is shown to the left), L=total cell lysate, P=pellet, Sup=supernatant after centrifugation of whole cell lysate, FT=flow through Ni-NTA column, E=target protein NT2RepCT eluted from the Ni-NTA column.
FIG. 2B: Photograph of gel of NT2RepCT, formed at 300 mg/ml protein concentration. Scale bar 0.1 cm.
FIG. 2C: Cryo-EM of NT2RepCT at 0.001 mg/ml. Scale bar 50 nm.
Figure 6:
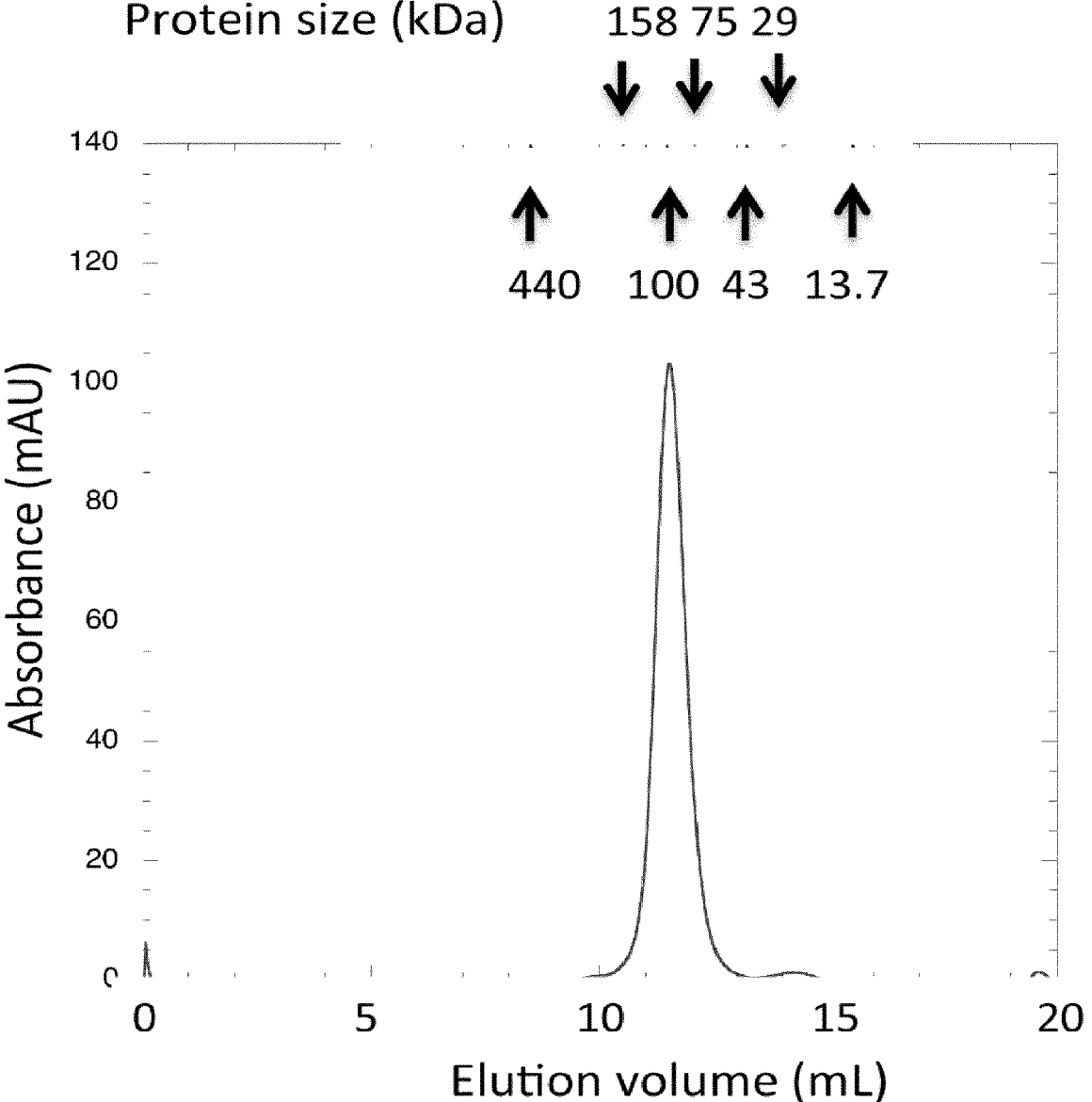
FIG. 6: Size exclusion chromatography of NT2RepCT. The protein sizes above the chromatogram are derived from calibrant proteins.

The inventors designed a minispidroin composed of NT from *E. australis* MaSp1 and CT from *A. ventricosus* MiSp bracketing a short repetitive region from *E. australis*. The chimeric NT2RepCT protein was produced at unprecedented high levels in shake flask *E. coli* cultures and the yield after purification was around 125 mg protein/L cell culture. Nearly all protein was soluble after expression and lysis, and bound efficiently to the Ni-NTA column (FIG. 2A). The eluate contained >95% pure NT2RepCT and the size of the protein on the SDS PAGE gel corresponded well to the expected molecular mass (33 kDa) (FIG. 2A). Size-exclusion chromatography indicated a mass of 100 kDa (FIG. 6), in good agreement with a dimer (due to the constitutive dimeric nature of CT) and a non-globular structure of the repetitive part.

Example 2: Chimeric Minispidroin NT2RepCT Exhibits Extreme Solubility

Figure 7A:
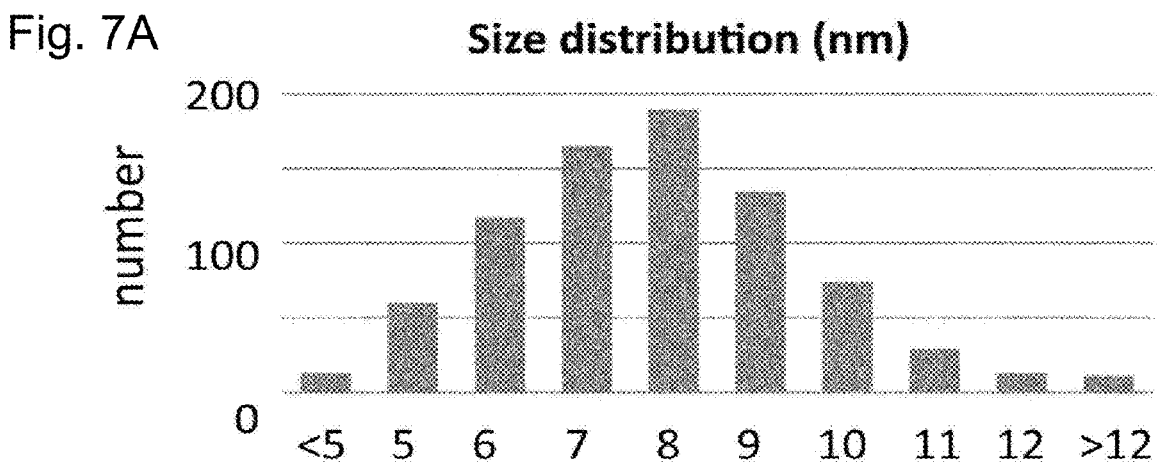
FIG. 7A: Size distribution of micelles using transmission electron microscopy with negative stain.
Figure 7B:
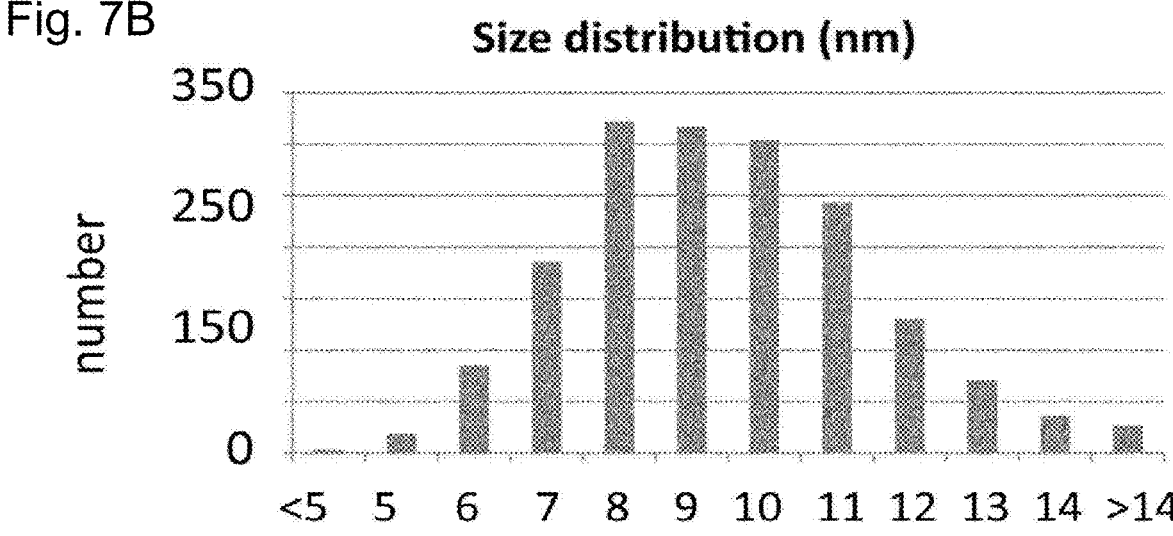
FIG. 7B: Size distribution of micelles using cryo-electron microscopy.
Figure 7C:
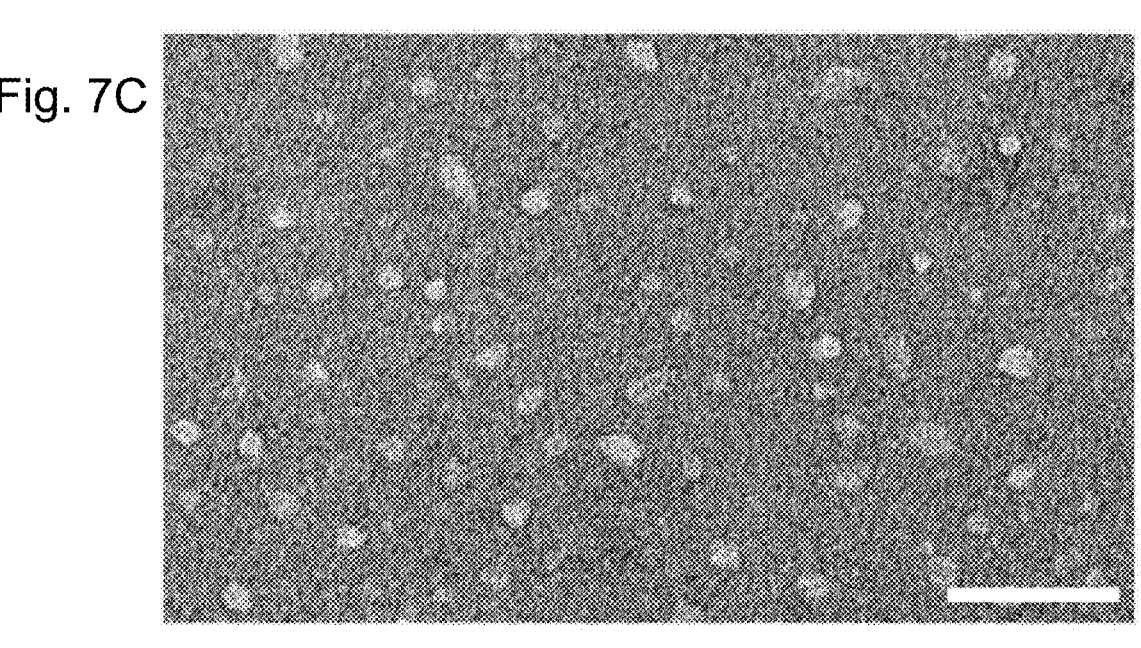
FIG. 7C: Transmission electron micrograph of micelles with negative stain. Scale bar 50 nm.

Obtaining spinning dopes of high concentration in water has been a long-standing major goal, but to date, the reported concentrations of artificial spinning dopes have been in the range of 10-30%, even though non-physiological solvents have been used. NT2RepCT of Example 1 far surpassed all expectations in terms of solubility; it could be concentrated to 500 mg/ml in aqueous buffer at pH 8 without precipitation, which equals or even exceeds the protein concentration in the spinning dope of the spider. At such high concentrations, the protein formed a yellow hydrogel (FIG. 2B). Native spider silk dope has been showed to be stored as micelles, 100-200 nm in diameter, probably with the terminal domains in the shell and the repetitive regions shielded in the core. This has also been proposed to be the storage mechanism in silkworm silk glands. The NT2RepCT protein behaves as native silk proteins in this respect and assembles into ~10 nm micelles (FIG. 2C, FIG. 7). The smaller diameter of the micelles composed of recombinant spidroin compared to the micelles in native spider silk dope is expected from the short repetitive region of NT2RepCT. NT2RepCT at 500 mg/ml could be stored at 4° C. for weeks and at −20° C. for months with maintained ability to form fibers (c.f. below). This is surprising, since the reported typical stability of artificial spinning dope solutions is 3-5 days.

Published purification protocols have involved precipitation of the expressed protein with ammonium sulfate, lyophilization, followed by solubilization in HFIP or guanidinium-thiocyanate. The presence of non-aqueous solvents or other denaturants during production will likely prevent formation of native structures and we propose that the high solubility and stability over time of NT2RepCT is related to the presence of natively folded NT and CT, a supposition that is supported by the observation of native-like micellar structures.

Moreover, Fourier transform infrared (FTIR) spectroscopy of NT2RepCT protein in solution showed amide I and II band maxima approximately at wavenumber 1545 and 1650 $cm^{-1}$, respectively (FIG. 9), which indicates an alpha helical structure. This is in good agreement with the native five-helix bundle structures of both NT and CT.

Example 3: Biomimetic Spinning of the NT2RepCT Minispidroin

Figure 3A:
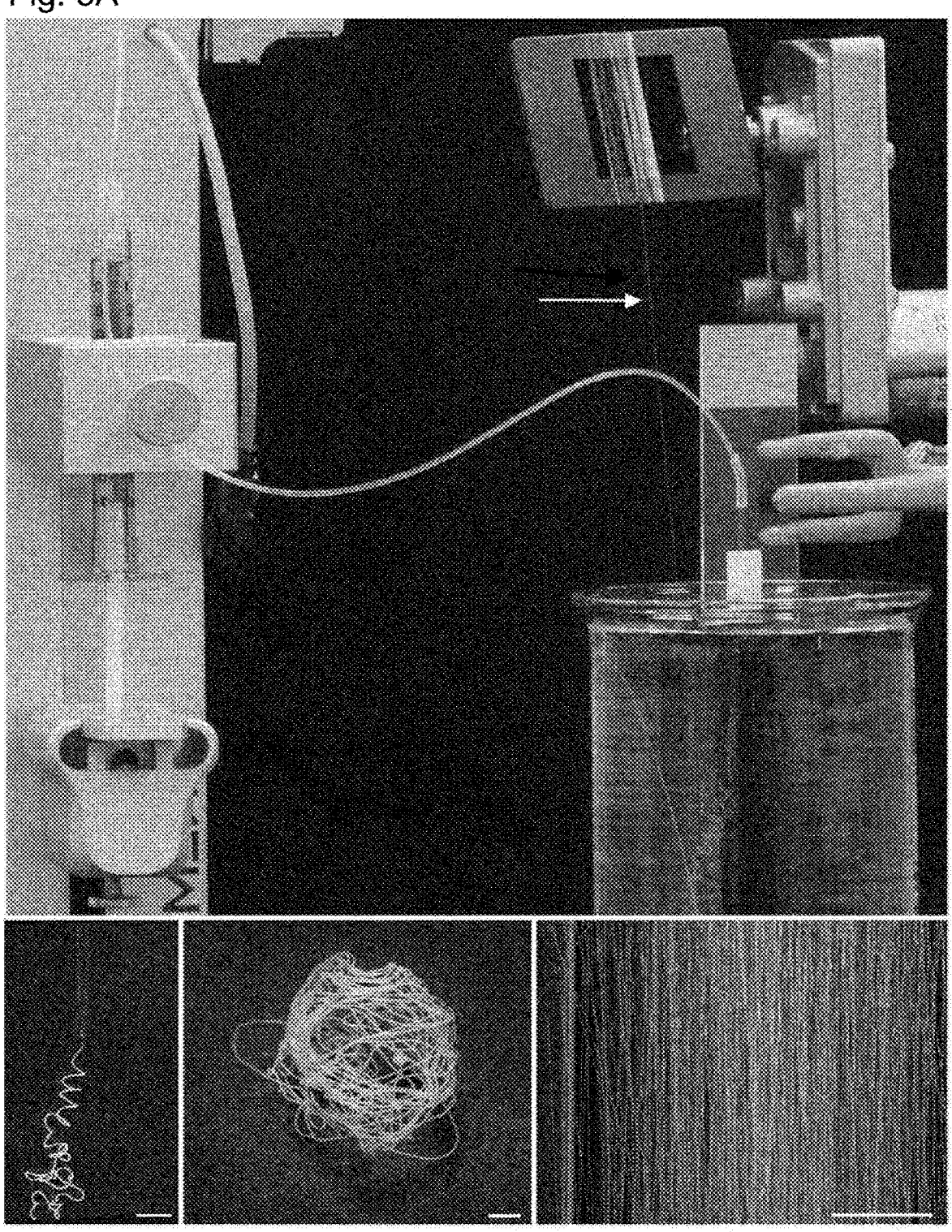
FIG. 3A: Highly concentrated NT2RepCT spinning dope in a syringe is pumped through a pulled glass capillary with a tip size of 10-30 μm, with the tip submerged into a low pH aqueous collection bath. Fibers can be pulled up (arrow) from the collection bath and rolled up onto frames.
Figures 8A, 8B, 8C, 8D:
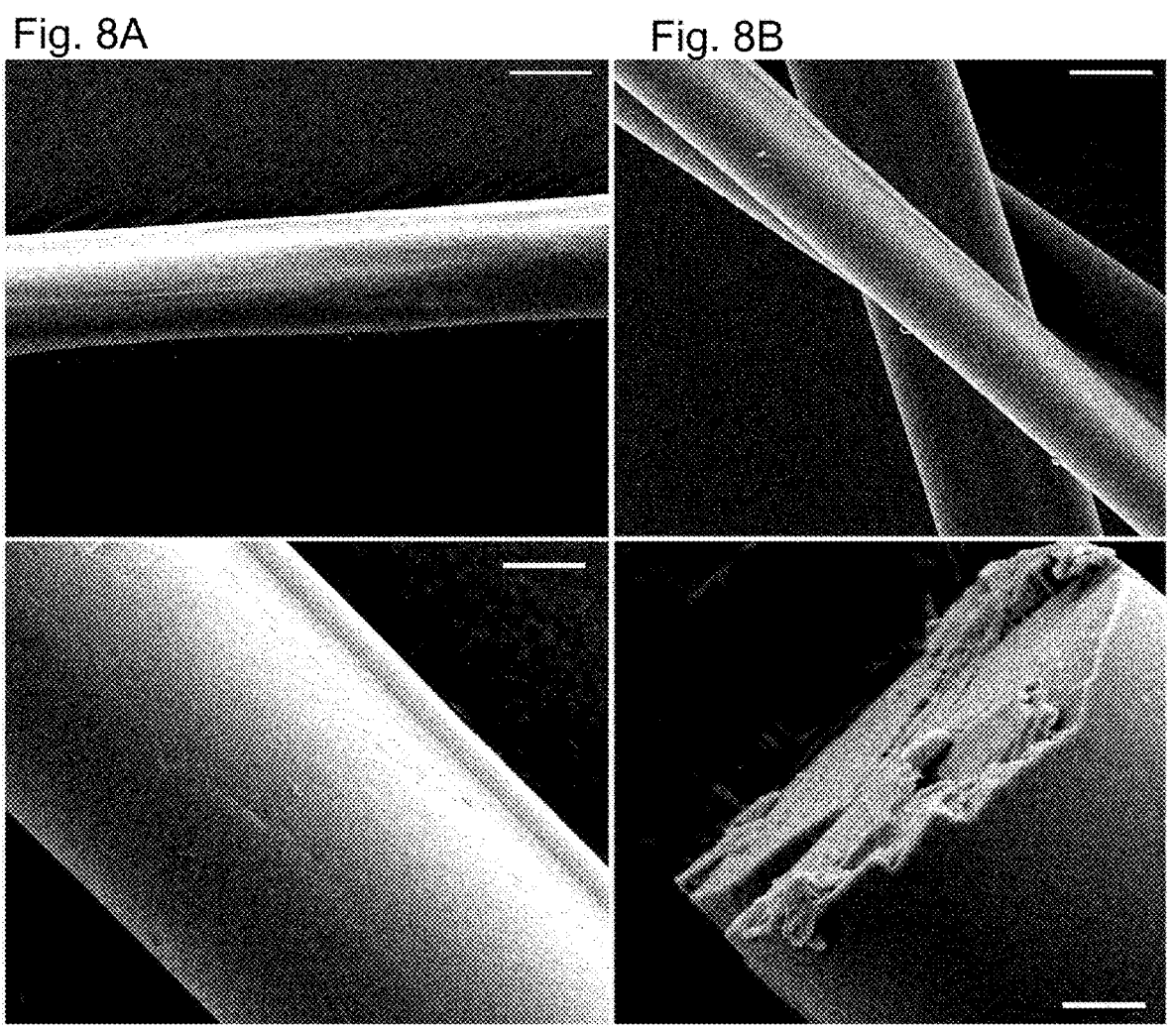
FIG. 8A: As-spun fibre.
FIG. 8B: As-spun fibres collected on a frame.
FIG. 8C: Fibre post-stretched 200% in 500 mM sodium acetate buffer and 200 mM NaCl (pH 5).
FIG. 8D: Fracture surface of a post-stretched fibre to examine the fibre interior core. All fibres were spun in a collection bath with 500 mM sodium acetate buffer and 200 mM NaCl (pH 5). Scale bars are 10 μm in FIGS. 8A-8B and 2 μm in FIGS. 8C-8D.

Another prerequisite that needs to be fulfilled in order to achieve biomimetic spinning is to engineer a spinning device that can mimic the conditions of the spider silk gland. We designed a first-generation simple but efficient spinning device from a thin pulled glass capillary through which the highly-concentrated NT2RepCT dope is pumped into an acidic aqueous buffer collection bath (FIG. 3). This setup generates a drop in pH and allows shear forces to act on the dope as it travels through the tip of the capillary, and results in formation of a continuous solid fiber (FIG. 3A-B). Fibers could easily be reeled onto rotating frames in air at lengths exceeding hundreds of meters (FIG. 3C). The dope concentration interval at which fibers could be spun ranged from 100 to 500 mg/ml. Fibers spun from dopes with concentrations >200 mg/ml were more easily handled and could be spun into a continuous fiber without breaking. As-spun fibers were homogenous as judged by SEM with a diameter of approximately 10-20 μm (FIG. 8). Fibers post-stretched in a low pH bath had slightly decreased diameters compared to as-spun fibers. The fracture surfaces from fibers that were pulled until failure show a compact and homogenous interior core (FIG. 8).

Figure 9:
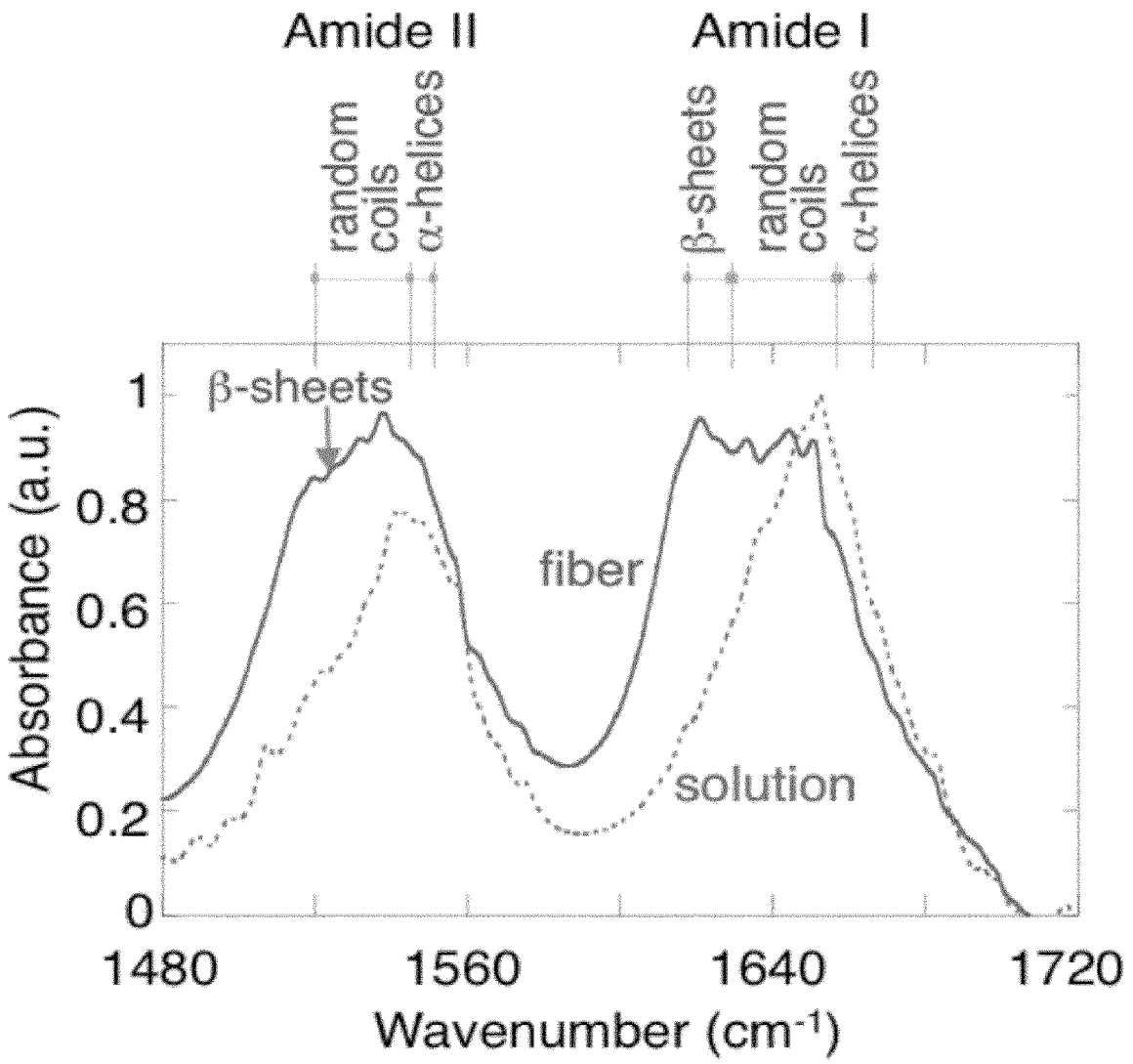
FIG. 9: Fourier Transform Infrared Spectroscopy of NT2RepCT. FTIR spectra of NT2RepCT protein in solution (dotted line) and NT2RepCT fibres (solid line).

Fourier transform infrared spectroscopy (FTIR) analysis of NT2RepCT fibers showed an increase in β-sheet conformation compared to the soluble state, as can be seen by the shift in the amide I and II peak distributions (FIG. 9).

Example 4: Effect of pH on Fiber Spinning

Figures 4A, 4B, 4C:
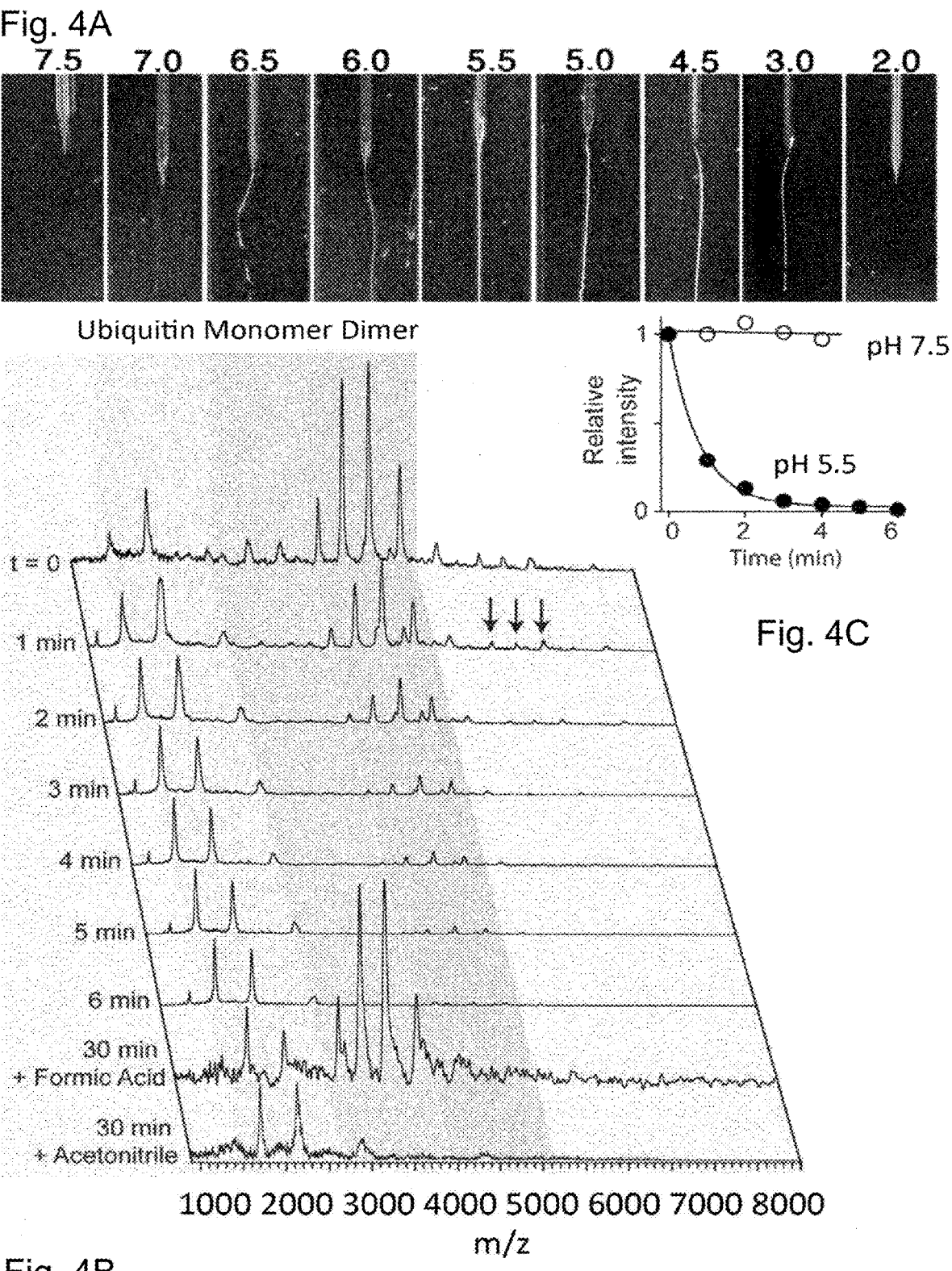
FIG. 4A: Spinning into buffers at different pH values. Continuous fibers that can be pulled up and rolled onto a frame are formed in buffers with 3.0≤pH≤5.5.
FIG. 4B: nESI-MS time-course of NT2RepCT incubated at pH 5.5. Prolonged exposure to low pH induces aggregation of NT2RepCT. Addition of concentrated formic acid to the aggregates releases monomers, but addition of acetonitrile does not. Ubiquitin was used as internal standard to follow the time-dependent signal decrease for the residual NT2RepCT dimer.
FIG. 4C: At pH 7.5, a stable population of native dimers can be detected (open symbols), while incubation at pH 5.5 leads to complete loss of soluble NT2RepCT over the course of a few minutes (Filled symbols).

To further investigate the effect of pH on fiber spinning, the dope was extruded into aqueous baths with pH ranging from 2.0 to 7.5. Discontinuous fiber-like structures were formed when pH of the bath was between 6.0-6.5 (FIG. 4A). Continuous fibers were formed when pH was between 3.0 and 5.5 (FIG. 4A) and the fibers were easily pulled from collection baths and could be reeled onto frames (FIGS. 3 and 4). If the pH of the collection bath was ≤2.5 no fibers could be seen (FIG. 4A).

Example 5: Assembly of NT2RepCT on a Molecular Level

Figure 10:
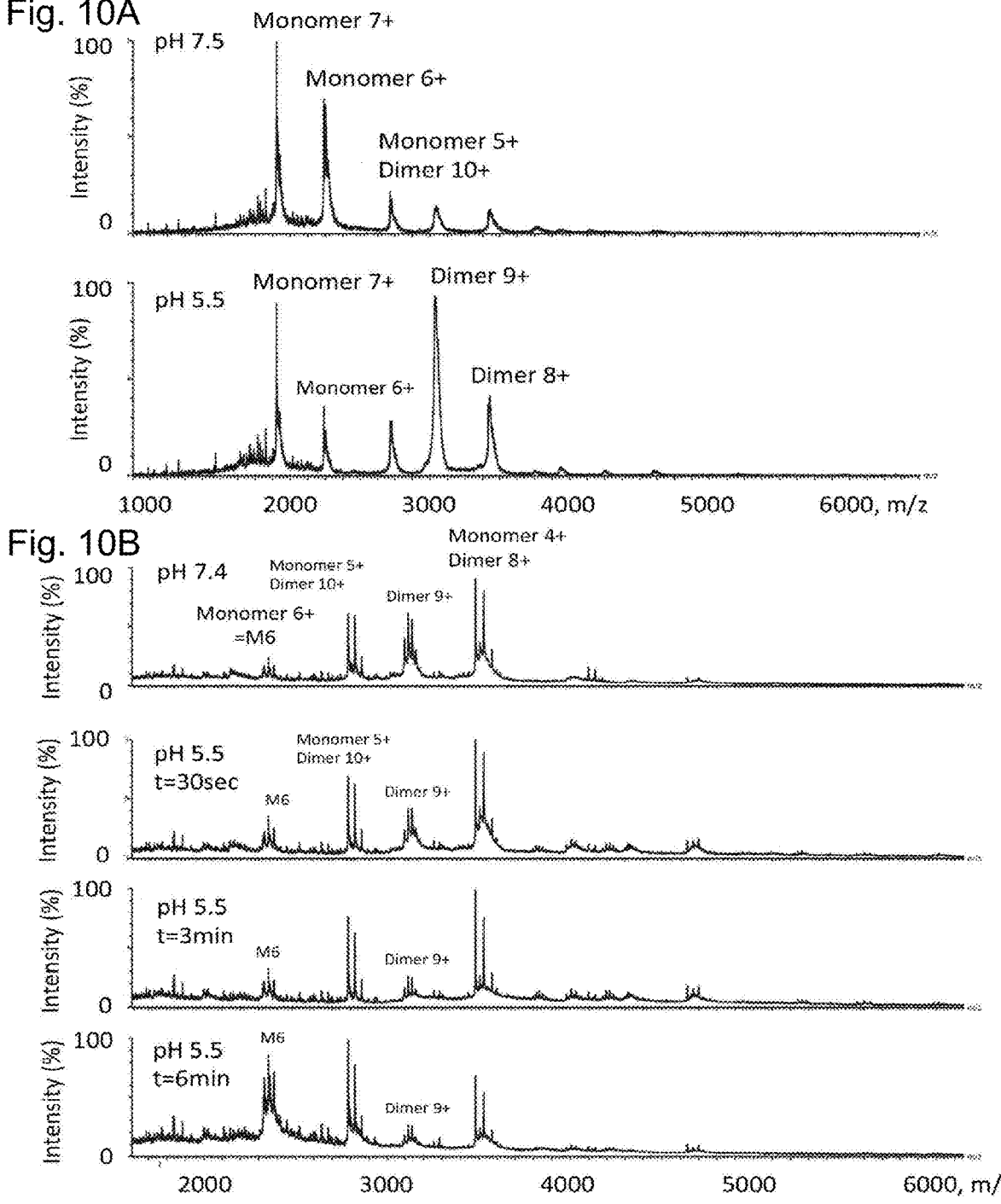
FIG. 10: Effect of pH changes on isolated NT and CT.

To further investigate the pH-dependent assembly of NT2RepCT at a molecular level, we used nano-electrospray mass spectrometry (nESI-MS). As expected, nESI-MS at pH 7.5 showed the presence of a major molecular species of 66560 Da, which corresponds to the native NT2RepCT dimer. Lowering the pH to approximately 5.5 induces a significant shift in the quarternary structure. Oligomers (mainly tetramers, arrow in FIG. 4B) could be observed up to one minute after the addition of formic acid directly to the sample in the electrospray capillary. Following loss of the higher oligomers, only low-intensity peaks corresponding to dimers could be detected, which further decreased to baseline over the course of five minutes (FIG. 4B). These findings correlate well with the pH-dependent lock and trigger actions of the terminal domains. NT on its own undergoes rapid antiparallel dimerization at low pH (FIG. 10), which has been suggested to lead to cross-linking of the spidroins into an infinite-mer. For CT in isolation on the other hand, exposure to low pH leads to gradual unfolding, as indicated by an increasing amount of monomers, and eventually amyloid-like β-sheet nuclei, indicated by some higher charge states (FIG. 10). In analogy to amyloid-like fibrils (Solvent effects on self-assembly of beta-amyloid peptide. Shen CL, Murphy RM.Biophys J. 1995 August; 69(2):640-51) addition of acetonitrile could not dissolve higher-order oligomers of NT2RepCT, while concentrated formic acid recovered the monomer signal, indicating dissociation of the aggregates through denaturation (FIG. 4B).

Example 6: Mechanical Properties of Spun NT2RepCT Fibers

Figure 5:
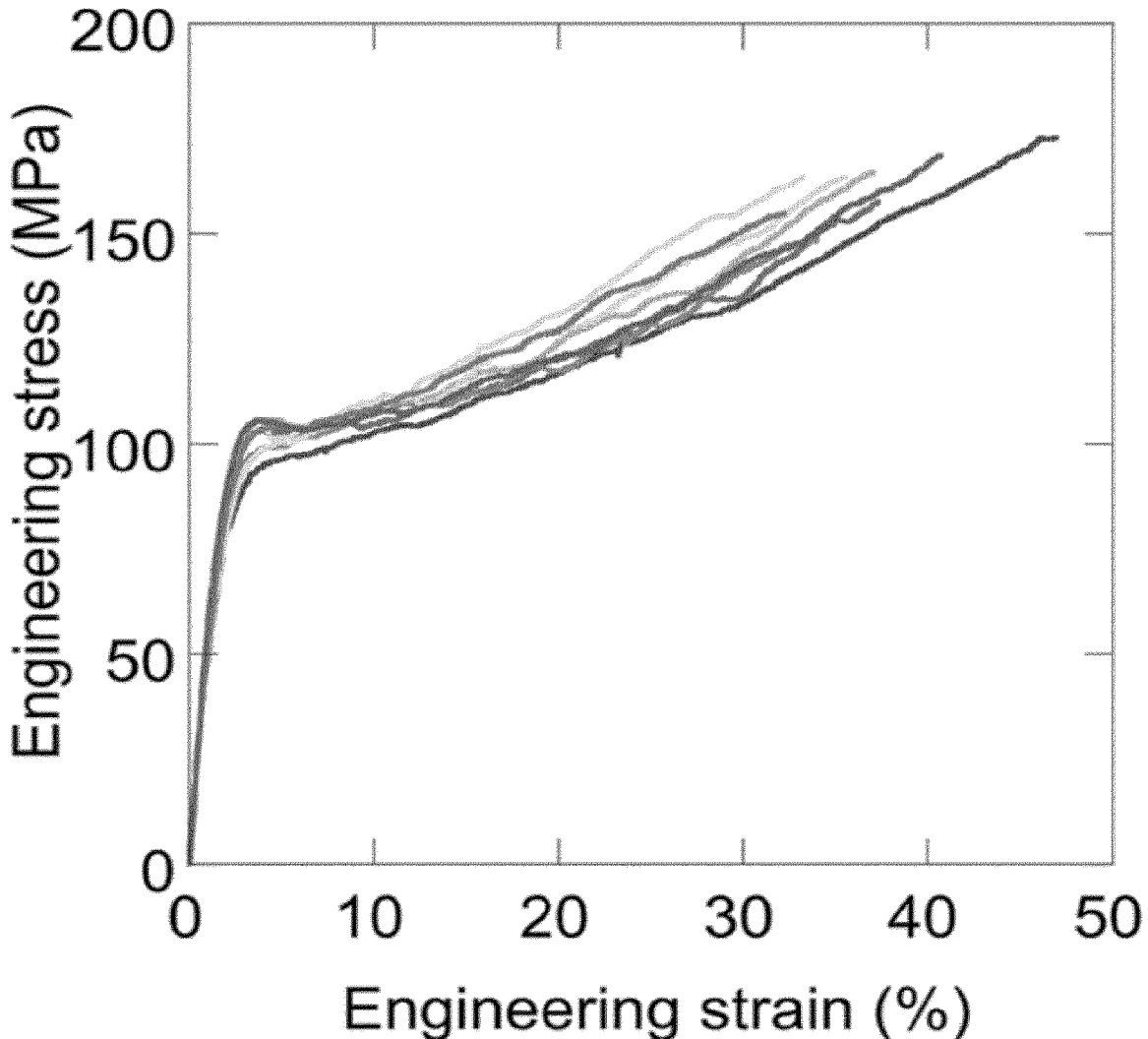
FIG. 5: Tensile properties of NT2RepCT fibers. Engineering stress/strain curves for eight separate NT2RepCT fibers.

The strength and extensibility of native dragline fibers differ a lot between spider species and are also highly dependent on environmental factors like humidity and temperature, but they all display initial elastic behavior up to a yielding point, after which plastic deformation occurs. The behavior of as spun NT2RepCT fibers when exposed to stress is similar to native dragline silk, but with lower tensile strength and higher strain (FIG. 5). NT2RepCT fibers as-spun into a pH 5 aqueous collection bath have a toughness of 45±7 MJ/m³ (FIG. 5, Table 3), approaching the toughness of *A. trifasciata* dragline silk (100±40 MJ/m³)$^{\underline{\overline{}}}$ (Table 3). The Young's modulus is around 6 GPa, which is half the value of native *Argiope trifasciata* dragline silk.

TABLE 3

| | Comparison of mechanical properties of native dragline silk from *A. trifasciata* and different as-spun synthetic spider silk fibers | | | | | | | |
|---|---|---|---|---|---|---|---|---|
| Material | Native dragline silk *Argiope trifasciata* Ref 1 | NT2RepCT | eADF3 (AQ)$_{12}$NR3 Ref 2 | Synthetic MaSp1 and MaSp2 Ref 3 | Flag/ MaSp2 A1S8$_{20}$ Ref 4 | MaSp2 1E Ref 5 | Flag GF Ref 6 |
| Diameter (μm) | ≈3 | 12 ± 2 | 39 ± 6 | 61 ± 2 | 32 ± 16 | 106 ± 5 | 37 ± 1 |
| Extensibility (%) | 17 ± 0.04 | 37 ± 5 | 7 ± 2 | 1.1 ± 0.3 | 3.7 ± 1 | 0.8 ± 0.3 | 1.1 ± 0.9 |
| Strength (MPa) | 890 ± 130 | 162 ± 8 | 54 ± 16 | 33 ± 7 | 28 ± 17 | 14 ± 4 | 19 ± 5 |
| Toughness (MJ m⁻³) | 100 ± 40 | 45 ± 7 | 2 ± 0.8 | 0.2 ± 0.1 | 0.5 ± 0.3 | 0.06 ± 0.03 | 0.12 ± 0.11 |
| Young's modulus (GPa) | 11.6 ± 0.7 | 6 ± 0.8 | 2 ± 0.9 | ≈3 | 0.8 ± 0.5 | 1.7 ± 0.4 | |

Ref 1. Plaza, G. R., Perez-Rigueiro, J., Riekel, C., Perea, G. B., Agullo-Rueda, F., Burghammer, M., Guinea, G. V., Elices, M.. Relationship between microstructure and mechanical properties in spider silk fibers: identification of two regimes in the microstructural changes. *Soft matter* 8, 6015-6026, (2012).
Ref 2. Heidebrecht, A. et al. Biomimetic fibers made of recombinant spidroins with the same toughness as natural spider silk. *Adv Mater* 27, 2189-2194, (2015).
Ref 3. Copeland, C. G., Bell, B. E., Christensen, C. D., Lewis, R. V. Development of a Process for the Spinning of Synthetic Spider Silk. *ACS Biomaterials Science and Engineering* 1, 577-584, (2015).
Ref 4. Teulé, F. F., W. A.; Cooper, A. R.; Duncan, J. R.; Lewis R. V. Modifications of spider silk sequences in an attempt to control the mechanical properties of the synthetic fibers. *J Mater Sci* 42, 8974-8985, (2007).
Ref 5. Albertson, A. E., Teule, F., Weber, W., Yarger, J. L. & Lewis, R. V. Effects of different post-spin stretching conditions on the mechanical properties of synthetic spider silk fibers. *J Mech Behav Biomed Mater* 29, 225-234, (2014).
Ref 6. Adrianos, S. L. et al. Nephila clavipes Flagelliform silk-like GGX motifs contribute to extensibility and spacer motifs contribute to strength in synthetic spider silk fibers. *Biomacromolecules* 14, 1751-1760, (2013).

Previously published methods to produce artificial spider silk fibers include electrospinning, hand-drawing, spinning through microfluidic devices, and wet spinning, often into coagulation baths of aqueous alcohols. None of these methods have resulted in fibers with mechanical properties equal to those of native spider dragline silk, probably due to a combination of the proteins being denatured in the production and spinning processes and lack of biomimetic conditions. As-spun fibers have maximum tensile stress in the range of 14-55 MPa, and strain levels between 1-7%, resulting in a toughness of up to 2 MJ/m$^3$ (Table 3). To increase mechanical properties of the fibers, different post-spinning treatments are required. The toughest fiber so far published, with maximum stress of 500 MPa and strain of 15±5% was obtained for a native-sized recombinant protein without terminal domains that had been post-stretched 500%, but stress levels of as-spun fibers were not reported. In light of these results, our as-spun fibers have surprisingly good mechanical properties, considering that only about 2% of the native repetitive region is included in the minispidroin. NT2RepCT fibers are, to the best of our knowledge, the toughest as-spun fibers so far produced (Table 3).

Example 7: Solubility of Dry Fibers in Different Solvents

Dry fibers are dissolved in dH$_2$O. The inventors studied which aqueous buffers and solvents that dry fibers can be put in without being dissolved.

Spinning fibers was performed in glass capillaries as described in Example 3 Fibers were spun into a collection bath with 500 mM NaAc and 200 mM NaCl, pH 5. As-spun fibers were pulled up from the collection bath and allowed to dry, after which single fibers were dipped into different solutions to check if fibers dissolved or not.

Tested Dipping Solutions:
1. 200 mM Citric acid, pH 3
2. 500 mM NaAc and 200 mM NaCl, pH 5
3. 1M NaCl, pH 6.6
4. dH$_2$O
5. 20 mM Hepes/Mes, pH 5.5
6. 20 mM Hepes/Mes, pH 7.5
7. Mes, pH 5.15
8. 20 mM Tris, 100 mM NaCl, pH 8

Fibers were not dissolved in dipping solutions 1-3, but were dissolved in solutions 4-8. It was concluded that a combination of pH and ionic strength are factors that influence the solubility.

Example 8: Spinning of NT2RepCT into Different Collection Baths

To study the influence of the composition and ionic strength of the collection bath on spinning NT2RepCT fibers, additional tests were performed in a setting similar to Example 3, except for the solution in the collection bath.

Tested Collection Baths:
1. 1000 mM NaAc buffer with 400 mM NaCl, pH 5
2. 500 mM sodium acetate (NaAc) buffer with 200 mM NaCl, pH 5
3. 20 mM NaAc buffer, pH 5
4. 20 mM phosphate buffer, pH 6.2
5. 20 mM tris, 500 mM NaCl, pH 7.2
6. 80% aq. isopropanol
7. 40% aq.isopropanol, 500 mM NaAc, 200 mM NaCl
8. 60% methanol, 40% water
9. 60% aq. methanol, 500 mM NaAc, 200 mM NaCl 10. 33% PEG 6000(Polyethylene glycol 6000)
11. 16.5% PEG 6000, 500 mM NaAc, 200 mM NaCl, pH 5

Figure 11:
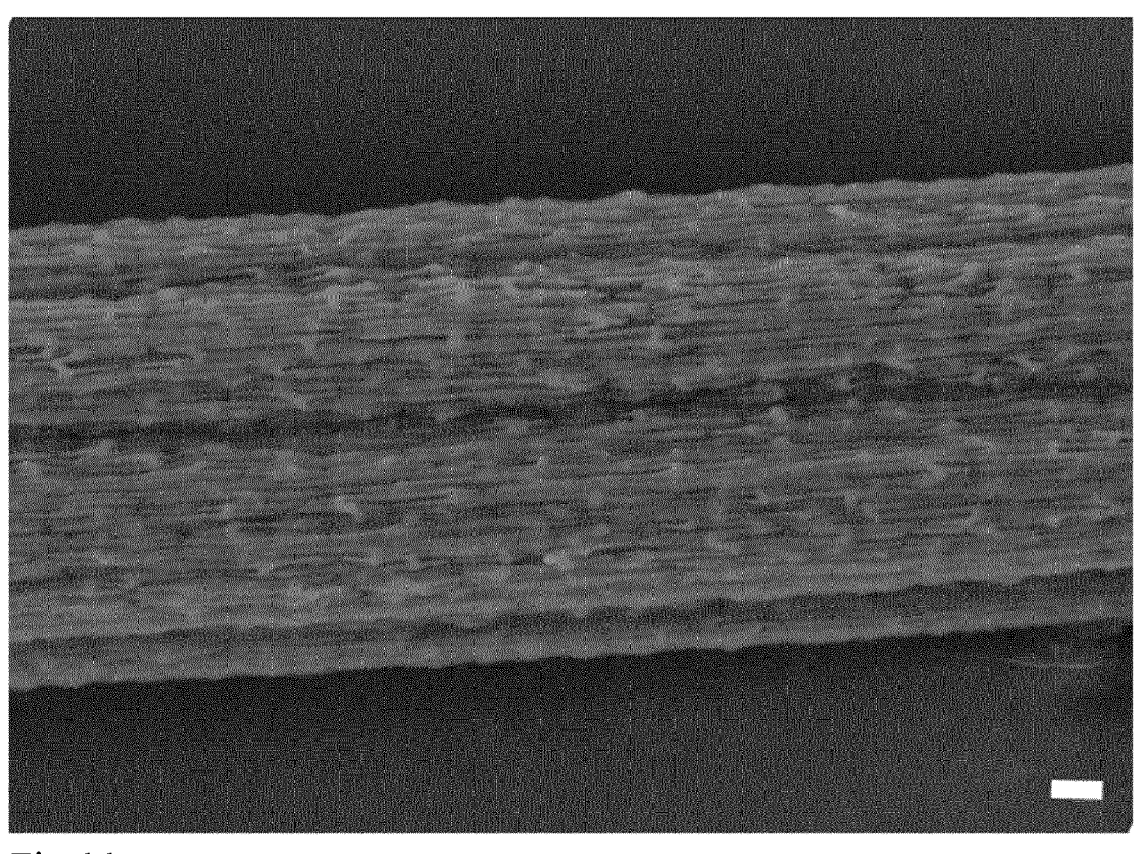
FIG. 11: Scanning electron micrograph of NT2RepCT fiber spun into isopropanol. Scale bar is 5 μm.

Continuous fibers were formed in collection baths 1-2, 6-11. Collection baths 3-5 gave only short fibers that dissolved easily. The PEG fibers looked quite similar to the fibers prepared in sodium acetate buffer, while the isopropanol (FIG. 11) and methanol fibers had a different macroscopic appearance. Isopropanol fibers were less opaque than NaAc fibers. Methanol fibers were fully transparent, and more gel-like.

The fibers that seemed strongest were produced in collection bath 2 (500 mM NaAc, 200 mM NaCl pH 5). The fibers that were easiest to post-stretch in air after spinning (i.e. more extendible) were produced in collection bath 11 (16.5% PEG, 500 mM NaAc buffer, 200 mM NaCl pH 5).

Example 9: Tensile Properties and Secondary Structure of NT2RepCT Fibers Spun in Different Collection Baths, at Different Temperatures, or Post-Stretched in Different Baths Aims
1) To study the influence of the composition of the collection bath on tensile properties of NT2RepCT fibers
2) To study the influence of post-stretching on tensile properties of NT2RepCT fibers Methods Study 1): NT2RepCT fibers were spun as described in the Example 3, into following different collection baths:
  160223_1: 500 mM NaAc, 200 mM NaCl, pH 5
  160223_2: 500 mM NaAc, 200 mM NaCl, 15% PEG, pH 5
  160303_4: 500 mM NaAc, 200 mM NaCl, pH 4.25

Study 2): NT2RepCT fibers were spun as described in Example 3 into a collection bath with 500 mM NaAc, 200 mM NaCl, pH 5 and were subsequently:
  160223_4: post-stretched in 50% MetOh and 500 mM NaAc, 200 mM NaCl, pH 5;
  160223_5: post-stretched in 30% PEG;
  160303_5a: post-stretched in 80% isopropanol; or
  160303_5 b: dipped in 80% isopropanol (without stretching)

Tensile tests (160223 samples) were performed as described in Example 3. Alternatively, (160303 samples) tensile tests were performed using the same procedure as described in Example 3, except for that the tensile tester brand was Shimadzu.

Results

Spinning into a collection bath containing PEG increases the toughness of the fibers, as compared to collection bath with only 500 mM NaAc, 200 mM NaCl, pH 5. However, the NT2RepCT fibers (160223_1) spun into 500 mM NaAc, 200 mM NaCl, pH 5 had a much lower toughness than NT2RepCT fibers from other batches.

Post-stretching in presence of methanol increases the tensile strength of the fibers, while post-stretching in 30% PEG increases the strain of the fibers.

Lowering the pH to 4.25 yields fibers that are much more fragile.

Post-stretching in isopropanol increases the tensile strength, but decreases strain, while only dipping in isopropanol increases the strain.

Example 10: Pilot Study on 3D Printing with NT2RepCT

The study aimed to test printing fiber structures with NT2RepCT protein and printing NT2RepCT gel fibers.

NT2RepCT was expressed, purified and concentrated as described in Example 1.

The spinning setup was as described in Example 3. The pulled glass capillary was then moved around while spinning, to print names and symbols.

For gel experiments, the highly concentrated NT2RepCT protein was kept in a syringe and extruded through a 27G needle into a petri dish. A gel-structure was printed, after which a low pH buffer (500 mM NaAc, 200 mM NaCl, pH5) was poured in the petri dish.

Figure 12A:
FIG. 12A: Printed names with NT2RepCT fiber in low pH buffer.
Figure 12B:
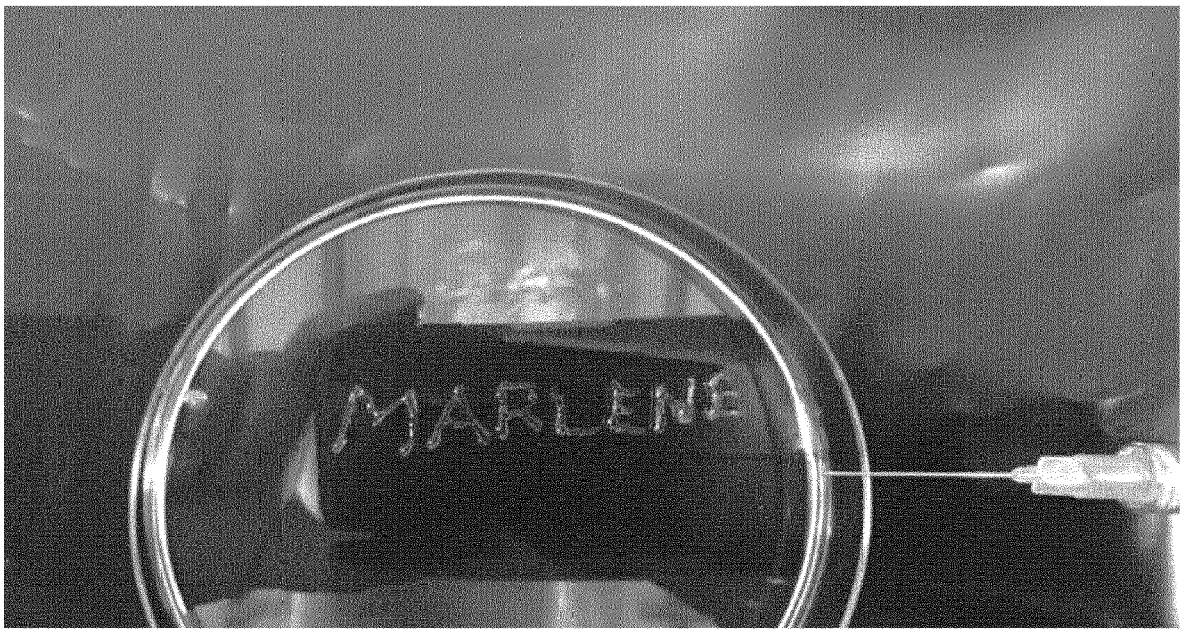
FIG. 12B: Printed name with NT2RepCT gel.
Figure 12C:
FIG. 12C: Printed name with NT2RepCT gel, solidified by pouring pH 5 sodium acetate buffer on the printed structure.
Figure 14:
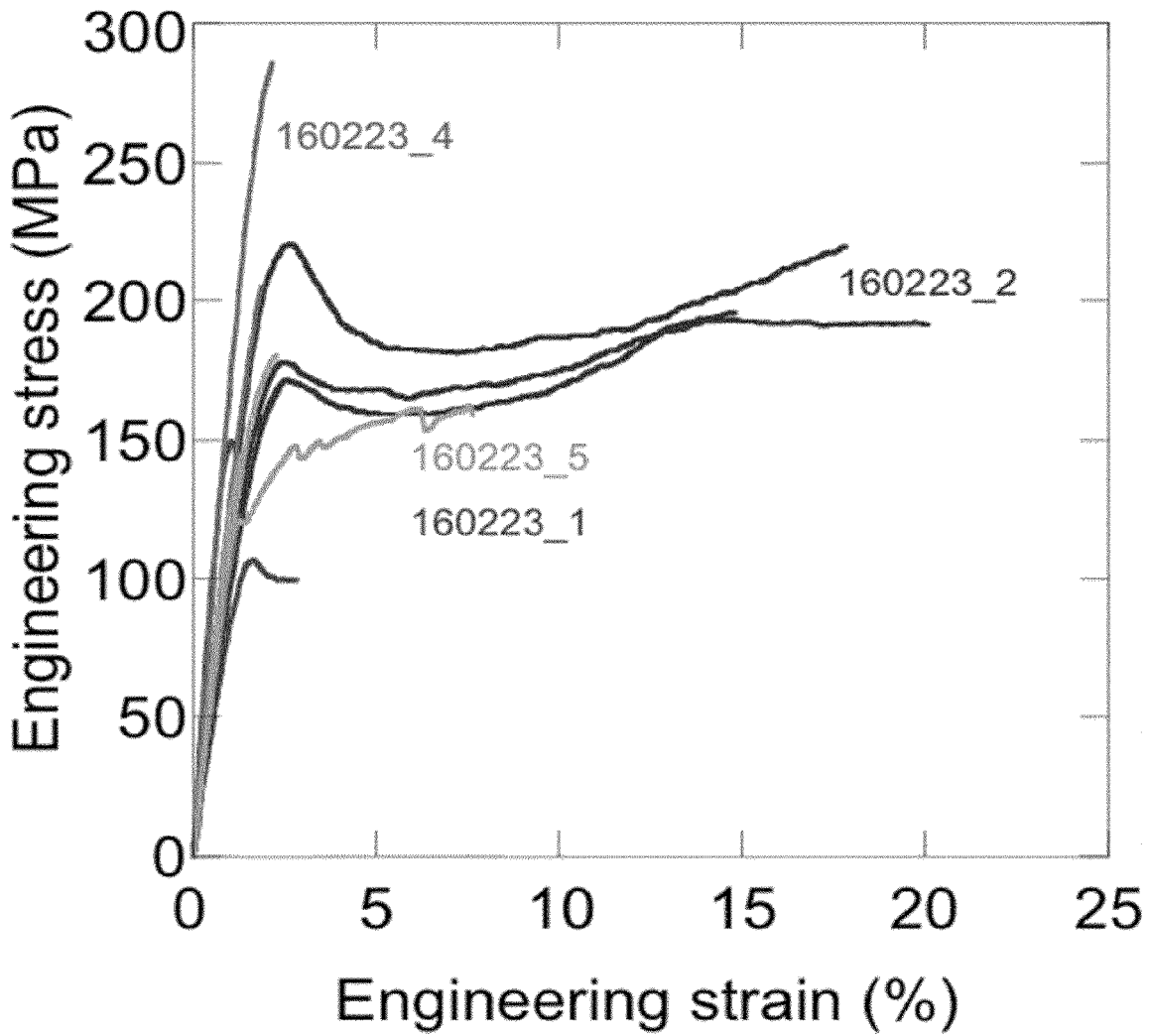
FIG. 14: Stress vs strain curve of NT2RepCT fibers spun into different collection baths, or post-stretched in different baths.

Both studies show the feasibility of printing NT2RepCT using a 3D printer. In both studies, names and symbols could be printed (FIG. 12A-C). A 3D printer could thus print either in dry state, or in a wet state with low pH.

Comparative Example 11: Comparative Examples Fiber Formation

Three different constructs: MaSpCT, NT4rep, 4repCT (all constructs contain parts from MaSp, i.e. no MiSp CT is included) were expressed, purified and fiber formation was performed by using a gentle tilting method in glass tubes, essentially as described by Stark et al 2007, but with addition of lowering of pH to enable studies of the influence of pH on the fiber formation properties of the different minispidorin constructs.

Methods

An over-night culture of the different constructs was prepared by inoculating 20 mL of LB media (with kanamycin) from a glycerol stock. The overnight culture was grown at 30° C., 200 rpm.

5 ml ON culture was added to 500 mL fresh LB media (with kanamycin) and grown at 30° C., 200 rpm until OD 0.9, after which the temperature was lowered to 25° C. and IPTG was added (final concentration 0.3 mM). Expression was continued for four hours, after which the cultures were centrifuged at 5000 rpm, 4° C. for 20 minutes. Pellets were dissolved in 30 ml 20 mM Tris pH 8 and stored at –20° C.

Cells were lysed by adding 600 ul lysozyme while thawing. When cells were thawed, 15 ul DNase and 60 ul (1M) MgCl2 was added and the samples were incubated on ice for 30 minutes. The lysates were centrifuged at 15000 rpm, 4° C., 30 rains after which the supernatant was loaded onto a Ni-sepharose column for purification. The column was washed with 20 mM Tris pH 8 and 20 mM Tris pH 8, 10 mM imidazole. The protein was eluted with 20 mM Tris, 300 mM imidazole pH 8. Thrombin (1 ug/mg protein) was added to the fusion protein and the samples were dialysed over night at 4° C. towards 20 mM Tris pH 8. The dialysed and cleaved samples were loaded on the Ni-sepharose column and the flowthrough containing the purified protein was collected, after which the protein purity was checked by SDS-PAGE and the protein concentration was measured at 280 nm.

Protein yield for the different constructs were:
NT4rep: 21 mg from 1 L shake flask culture
4repCT: 24 mg from 1 L shake flask culture
MaSpCT: 14 mg from 1 L shake flask culture The protein was concentrated to ≤3 mg/ml, and samples were then diluted in buffers of different pH and salt conditions to 1 mg/ml. Maximum concentration of 4RepCT was 10 mg/ml, then the protein precipitated.

The method used for fiber formation was: gentle tilting in glass tubes (as described by Stark et al 2007).

Three different pHs were tested: pH 7.5, 6.5 and 5.5 ca 10 mM Hepes/Mes. With or without 154 mM NaCl.

Results

MaSpCT forms short fibers (≤5 mm) after ca 3 hours of gentle tilting. pH and salt conditions do not influence neither the rate of fiber formation, nor the size of the fibers.

NT4rep does not form fibers, irrespective of pH or salt conditions

4repCT forms fibers (ca 2 cm long) in all pHs, but fiber formation is slower at pH 5.5. Fiber formation is equally fast at pH 6.5 and 7.5 but fibers are smaller at the lower pH values.

A mix of NT4rep and 4repCT (0.5 mg/ml each) forms long (3 cm) fibers, faster at pH 5.5 than at pH 6.5 or 7.5, but much slower than 4repCT alone.

Example 12: Production and Spinning of 2RepCT

2RepCT can be concentrated to >100 mg/ml and is spun into fibers by pumping the protein through a spinning device.

PGB1-2RepCT is expressed and purified as described for NT2RepCT in Example 1. The His-PGB1-tag is removed by cleaving with thrombin over night at 4° C. followed by reverse Immobilized Metal Ion Affinity Chromatograph (IMAC) after which 2RepCT is concentrated to 170 mg/ml (performed as described for NT2RepCT).

Round glass capillaries (G1, Narishige) with an outer diameter of 1.0 mm and inner diameter of 0.6 mm are pulled (Micro Electrode Puller, Stoelting co. 51217) to a tip diameter of 25 µm. A 1 ml syringe with Luer Lok tip (BD) is filled with 2RepCT (at 170 mg/ml) and connected to a 27G steel needle (Braun) with an outer diameter of 0.40 mm. The needle is connected to the pulled glass capillary via polyethylene tubing. A neMESYS low pressure (290N) syringe pump (Cetoni) is used to eject the PGB1-KL4 at a flow rate of 20 µl/min into a collection bath with either 500 mM NaAc 200 mM NaCl pH 5.0 or 50% methanol and 50% NaAc (500 mM), NaCl (200 mM) pH 5 within a 50 mL Falcon tube.

Continuous fibers form instantaneously as the 2RepCT is extruded through the capillary tip into the methanol/low pH collection bath and can be collected in the bottom of the Falcon tube, as well as being pulled up from the collection bath.

In conclusion, the 2RepCT can be produced at high yield and purity under native conditions, responds to pH lowering from 7 to 5, and is highly soluble in aqueous buffer, pH 7-8.

Example 13: Expression and Spinning of a NT2+2RepCT Minispidroin

The DNA sequence of NcolHisNt2x2RepCtHindIII was according to SEQ ID NO: 17. The amino-acid sequence of the expressed protein was according to SEQ ID NO: 18.

Expression

The expression was done in *E. coli* BL21 cells. Five ml of an 37° C. overnight cell culture in LB medium (with 70 ug/mL kanamycin) was transfered to 500 ml LB medium (with 70 ug/mL kanamycin) and cultured in shake flasks at 30° C. until $OD_{600}$ was 0.8-1.0. The temperature was then lowered to 20° C., and 150 µl of 1M IPTG (final concentration 0.3 mM) was added to induce expression. After overnight culture, the cells were harvested by centrifugation at 5,000 rpm, at 4° C. for 15 minutes. Cells from 500 ml culture were resuspended in 30 ml of 20 mM pH 8 Tris buffer and stored at –20° C. overnight.

Lysis and Purification

The cells were thawed and 30 ml cells were divided to two tubes and each tube was filled up to 30 ml with Tris buffer pH 8.0. Next, 600 µl lysozyme was added to each tube which was then incubated on ice for 1.5 h, whereafter 15 μl DNAse and 60 μl 1 M MgCl₂ was added and the samples were incubated on ice for one hour. The lysate was then centrifuged at 27,000 g for 30 min at 4° C. The first supernatant (supernatant 1) was loaded on a Ni-NTA column. The pellet was then resuspended in 30 ml Tris buffer pH 8.0, and stored at −20° C. overnight. The next day the pellet was thawed, centrifuged at 27,000 g for 30 min at 4'C, and the second supernatant was collected and loaded on a Ni-NTA column.

The supernatants were loaded on a gravity flow Ni-NTA column. The column was washed with (1) 20 mM Tris pH 8.0, (2) 100 mM NaCl in 20 mM Tris pH 8.0 and (3) with 10 mM imidazole in 20 mM Tris pH 8.0. The proteins were eluted with 300 mM imidazole in 20 mM Tris pH 8.0 The eluate containing the target proteins was dialyzed using a Spectra/Por® dialysis membrane with a 6-8 kDa molecular weight cut-off overnight in cold room against 20 mM Tris, pH 8.0 in order to remove imidazole.

The yields were as follows.

1) 41 mg protein from supernatant 1.

2) 46 mg protein from supernatant 2.

The yield is thus 87 mg from 1L LB medium shake flask culture. SDS-PAGE analysis of the purification process is shown in FIG. 13.

Concentration and Solubility

The NT2x2RepCT protein could be concentrated to the >300 mg/ml at pH 8.0 in 20 mM Tris.

Fiber Spinning

Fibers were successfully spun as described for NT2RepCT. There were no apparent differences in macrostructure or fiber forming capabilities between NT2RepCT and NT2+2RepCT.

Example 14: Spider Silk as Cell Culture Matrix

Human fetal cardiac mesenchymal stromal cells (hfMSC) were derived from human fetal heart week 6-9 (Månsson-Broberg et al., Wnt/b-Catenin Stimulation and Laminins Support Cardiovascular Cell Progenitor Expansion from Human Fetal Cardiac Mesenchymal Stromal Cells, Stem Cell Reports, 2016).

The cells were seeded onto spider silk matrix in medium consisting of Dulbeccos Modified Eagle Medium F12 (DMEM/F12, Sigma) supplied with 2% fetal bovine serum, 2% B27, Glutamine and Mycozap. Medium was changed two-three times a week.

After 10 days in culture spider silk matrix with cells was snap-frozen and sectioned into 5 μm sections. These were fixed in 4% Formaldehyde in PBS and blocked with 5% rabbit serum in PBS for immunohistochemistry. For Laminin alpha 4 and Ki67 stainings the slides were boiled in citric buffer pH7 (Invitrogen) for antigen retrieval. All primary antibodies were mouse-anti-human and added in block buffer according to: Alpha Smooth muscle actin (aSMA, A2547, Sigma) 1/250, CD31 (M0823, Dako) 1/300, TroponinT (ab8295, Abcam) 1/800, Heparan Sulphate (370255-1, Amsbio) 1/500, Laminin alpha 4 (CL3183, Atlas antibodies) 1/200, Ki67 (MIB1, Dako) 1/75. The slides were incubated in humidity chamber in room temperature over night, washed in PBS and the secondary antibody, rabbit anti mouse (Alexa fluor 488), was added in blockbuffer 1/700. The slides were incubated in humidity chamber in room temperature 90 min, washed and mounted with Dapi.

It was found that the cells readily attach to spider silk and can proliferate, a number of cells express Ki67. The cells express αSMA, Laminin alpha 4 and Heparan Sulphate, indicating formation of an extracellular matrix and basal membrane. In vivo, this could help the cells survive after transplantation, since they are offered anchorage and familiar extra cellular matrix. Anoikis, apoptosis due to loss of anchorage, could thereby be minimized and cell survival after transplantation increased.

Example 15: Effect of the Number of Charged Residues (K/R/E/D) in the C-Terminal Domain on the Solubility of Minispidroins The inventors expressed minispidroins that are identical to NT2RepCT (SEQ ID 11, see Example 1) with the exception of the CT that was exchanged for:

MiSp Ds CT (SEQ ID NO: 73): Minor ampullate silk protein *Deinopis spinosa*. Genbank accession no. ABD61589, resulting in NT2RepCT (MiSp Ds), SEQ ID NO: 74. This CT contains 11 charged residues.

MaSp1 Ea CT (SEQ ID NO: 27): Major ampullate spidroin 1 *Euprosthenops australis. Genbank accession no CAJ*00428.1, resulting in NT2RepCT (MaSp1 Ea), SEQ ID NO: 75, containing 4 charged residues in the CT.

ADF-4 (SEQ ID NO: 56): *Araneus diadematus* fibroin-4. Genbank accession no. ADU47856. resulting in NT2RepCT (ADF-4), SEQ ID NO: 76, containing 5 charged residues in the CT.

MiSp Lh CT (SEQ ID NO: 45): Minor ampullate spidroin *Latrodectus hesperus. Genbank accession no. ADM*14322.1, resulting in NT2RepCT (MiSp Lh), SEQ ID NO: 77, containing 5 charged residues in the CT.

The inventors also mutated individually two charged amino acid residues in the CT of NT2RepCT (SEQ ID NO: 11) (R38 and D105, respectively, to alanine) yielding NT2RepCTR38A and NT2RepCTD105A (SEQ ID NOs: 78 and 79, respectively). The substitutions reduce the number of charged residues in the CT domain from 7 to 6.

These six new proteins were expressed as described for NT2RepCT. If the protein was found in sufficient yield in the soluble fraction, the proteins were purified by IMAC chromatography, concentrated and subsequently spun into fibers as described for NT2RepCT.

Results: NT2RepCT (MiSp Ds) could be expressed, was found in the soluble fraction, could be purified and concentrated to >300 mg/ml and spun in the same fashion as NT2RepCT. NT2RepCT (MaSp1 Ea), NT2RepCT (ADF-4) and NT2RepCT (MiSp Lh) were all found in the insoluble fraction according to SDS PAGE analysis (FIGS. 20-22).

NT2RepCTR38A was expressed at high yields but was mainly found in the insoluble fraction. The NT2RepCTD105A was poorly expressed, and could not be obtained in sufficient amounts for protein concentration and fiber spinning.

Conclusions: the results support the conclusion that at least seven charged residues in the CT are necessary for obtaining NT2RepCT type of minispidroins that are soluble enough for purification, concentration and spinning in aqueous solvents.

Materials and Methods

Protein Expression and Purification

The construct NT2RepCT (SEQ ID NO: 12) encodes for a protein according to SEQ ID NO: 11, composed of a 6xHis tag (MGHHHHHHM—SEQ ID NO: 94) and an N-terminal domain based on the *E. australis* MaSp1 sequence:

```
(SHTTPWTNPGLAENFMNSFMQGLSSMPGFTASQLDDMSTI

AQSMVQSIQSLAAQGRTSPNKLQALNMAFASSMAEIAASEE

GGGSLSTKTSSIASAMSNAFLQTTGVVNQPFINEITQLVSM

FAQAGMNDVSA - SEQ ID NO: 95),
``` a repetitive part consisting of two polyalanine/glycine rich repeat regions from MaSp1 of *E. australis*:(GNSGRGQG-GYGQGSGGNAAAAAAAAAAAAAAAAGQGGQG-GYGRQSQGAGSAAAAAAA AAAAAAAGSGQG-GYGGQGQGGYGQSGNS-SEQ ID NO: 96), and a C-terminal domain based on the *A. ventricosus* MiSp sequence, preceded by a linker of 25 amino acids:

```
(VTSGGYGYGTSAAAGAGVAAGSYAGAVNRLSSAEAASRVS

SNIAAIASGGASALPSVISNIYSGVVASGVSSNEALIQALL

ELLSALVHVLSSASIGNVSSVGVDSTLNVVQDSVGQYVG -
SEQ ID NO: 97).
```

The construct was cloned into a pT7 plasmid and transformed into BL21 (DE3) *E. coli*. Luria broth media with kanamycin (70 mg/I) was inoculated with a glycerol stock of *E. coli* containing NT2RepCT and grown over night at 37° C. with shaking (200 rpm). The overnight culture was used for a 1/100 inoculation of 500 ml LB media with kanamycin, which was then cultured at 30° C. with shaking (200 rpm) until $OD_{600}$ reached 0.8, after which the temperature was lowered to 20° C. and protein expression was induced by adding isopropylthiogalactoside (IPTG) to a final concentration of 0.3 mM. The cells were cultured over night at 20° C. with shaking (200 rpm) and were then harvested by centrifugation for 20 minutes at 5000 rpm, 4° C. The pellets were resuspended in 20 mM Tris pH 8 and frozen at −20° C., or lysed immediately after resuspension.

Lysis was performed in a cell disrupter (T-S Series Machine, Constant Systems Limited, England) at 30 kPsi, after which the lysate was centrifuged at 27 000 g, at 4° C. for 30 minutes. Supernatants were loaded on a Ni-NTA column and the protein was eluted with 300 mM imidazole. The eluted protein was dialyzed against 20 mM Tris pH 8, at CC over night, using a Spectra/Por dialysis membrane with a 6-8 kDa molecular weight cutoff. SDS-polyacrylamide (12%) gel electrophoresis and Coomassie Brilliant Blue staining was used to determine the purity of the protein. Broad Range Protein Ladder (ThermoFisher Scientific) was used as a size standard.

The protein was concentrated using centrifugal filter units (Vivaspin 20, GE healthcare) with a 10 kDa molecular weight cutoff at 4000 g in rounds of 20 minutes. To determine the protein concentration, 1 µl protein was diluted 400 times in 20 mM Tris and the absorbance at 280 nm was recorded.

Size Exclusion Chromatography

A Superdex 200 HR column (Amersham Biosciences) was used to run 200 µl of purifed protein sample in TBS running buffer (20 mM Iris, 150 mM NaCl and 1 mM EDTA, pH 8.0). The flow rate used was 0.5 ml/min. Molecular mass standards Ribonuclease A (13.7 kDa), Carbonic anhydrase (29 kDa), Ovalbumin (43 kDa), Conalbumin (75 kDa), Aldolase (158 kDa) and Ferritin (440 kDa) were used for calibration.

Mass Spectrometry

For MS analysis, NT2RepCT was reconstituted into 100 mM ammonium acetate, pH 7.5 using biospin buffer exchange columns (Bio-Rad Laboratories). Silk assembly was induced by adding formic acid to a final concentration of 0.02% in a microcentrifuge tube, resulting in a pH of 5.5. As a reference for time-dependent assembly of spidroin, bovine ubiquitin (Sigma) was added to NT2RepCT samples at a final concentration of 0.2 mg/mL prior to the addition of formic acid. Samples were then immediately loaded into in-house produced gold-coated borosilicate capillaries and spectra were acquired continuously at 1 scan/sec for 10 minutes. For fibril dissolution, either concentrated formic acid or acetonitrile were added to a final concentration of 50% after 30 min incubation of NT2RepCT at pH 5.5. Spectra were acquired on a Synapt G1 T-wave mass ion mobility spectrometer (Waters) operated in ToF mode and equipped with a 32 k quadrupole for high-mass analysis. The settings were: capillary voltage, 1.4 kV; sample cone 20 V; source temperature, 20° C.; trap collision energy, 100 V; transfer collision energy, 10 V; trap DC bias 8 V. Backing pressure was maintained around 7 mbar. Data were analyzed using the MassLynx 4.1 software package (Waters). For each time-point, 60 scans were combined and spectra intensities normalized to the ubiquitin signal. Relative intensities were extracted using mMass and plotted using GraphPad 5.0.

Fiber Spinning

Round glass capillaries (G1, Narishige) with an outer diameter of 1.0 mm and inner diameter of 0.6 mm were pulled (Micro Electrode Puller, Stoelting co. 51217) to a tip diameter of 10-30 µm. A 1 ml syringe with Luer Lok tip (BD) was filled with NT2RepCT of a high concentration (100-500 mg/ml) and connected to a 27G steel needle (Braun) with an outer diameter of 0.40 mm. The needle was connected to the pulled glass capillary via polyethylene tubing. A neMESYS low pressure (290N) syringe pump (Cetoni) was used to eject the NT2RepCT at a flow rate of 1-20 µl/min into a low pH collection bath consisting of 500 mM sodium acetate buffer and 200 mM NaCl (pH 5). After formation, the fibers were pulled out of the collection bath and put on plastic to dry, or rolled up onto frames. Fibers were post-stretched by holding them between two tweezers in a low pH bath (500 mM NaAc with 200 mM NaCL, pH 5) for a few seconds, after which they were pulled to twice the original length, and put to dry on plastic.

For testing the influence of pH on spinning, different buffer systems and molarities of those buffer systems were used; sodium phosphate (100 mM) for pH >5.5, sodium acetate (100-500 mM) for pH 5.5-4, and citric acid (100-300 mM) for pH<4.

Fourier Transform Infrared (FTIR) Spectroscopy

FTIR analysis was carried out on liquid and solid samples using a Thermo Scientific Nicolet i55 with iD5 ATR at room temperature. For protein in solution, 254 scans were collected for each spectrum, while for fibers, 16 scans were performed. Three spectra were obtained for each type of sample and averaged for the curves shown.

Tensile Strength Measurements of Fibers

Fiber samples were mounted onto plastic frames with 20 mm gauge length using tape and glue (Loctite® Super Glue Professional). Fibers were visualized under a light microscope (Leica DM13000 B) using 40× object lens. Three photomicrographs were taken along the length of the fiber, and the diameter was measured from the photomicrographs using Carl Zeiss Zen 2012 to get an average diameter of the individual fiber piece. The sides of the plastic frame were cut off and the specimens were mounted in an Instron 4411 tensile testing machine. Force was measured with a Precisa XT 220 balance (resolution ±1 µN). The length of fiber where it was taut but not subjected to load was determined. Tensile test was performed at a pulling rate of 1 mm/min under nominal environmental conditions 24° C. and 30% relative humidity. All the tensile properties were calculated using KaleidaGraph. For the calculation of true stress and true strain, constant volume of fiber throughout the testing was assumed. The following equations were applied:

$$\sigma_T=\sigma_E(1+\varepsilon_E) \quad (1)$$

$$\varepsilon_T=In(1+\varepsilon_E) \quad (2)$$

where $\sigma_T$=true stress $\sigma_E$=engineering stress $\varepsilon_T$=true strain $\varepsilon^E$=engineering strain Scanning Electron Microscopy of Fibers Dry fibers (as-spun or post-stretched in 500 mM NaAc 200 mM NaCl pH 5.0) were put on scanning electron microscopy stubs, coated with gold/palladium for two minutes, and observed and photographed on a Zeiss Supra 35VP scanning electron microscope.

Study of Micellar Structures on TEM and Cryo-EM

NT2RepCT (5 mg/ml) was diluted to 0.001 mg/ml in 20 mM Tris buffer, pH 8.0. Negatively stained grids were prepared by incubating the sample for 30 seconds in a drop of 2% phosphotungstic acid, pH 7.8, blotting excess solution off and letting it dry. For cryo-electron microscopy, 3 μl aliquots of sample were applied to glow-discharged 400-mesh Quantifoil holey carbon grids. The cryo-samples were prepared in a controlled environment, at 16° C. and 100% humidity, using automated Vitrobot (FEI, Eindhoven, The Netherlands). Data was acquired with a JEOLJEM-2100f microscope operated at 200 kV and a nominal magnification of 80000. Images were collected with TVIPS TemCam-F415 4k×4k CCD-camera (Tietz Video and Image Processing Systems GmbH, Gauting, Germany). The size of the micelles was estimated using the image processing program ImageJ.

PGB1-2RepCT

DNA Sequence of PGB1-2RepCT was according to SEQ ID NO: 13 whereas the protein sequence of PGB1-2RepCT was according to SEQ ID NO:14).

The invention claimed is:

1. A method for producing a polymer of a recombinant spider silk protein, comprising the steps of:
   a. providing a first aqueous liquid medium comprising a spider silk protein in solution in said medium at a concentration of at least 100 mg/ml;
   b. adjusting the first aqueous liquid medium to pH 6.3 or below, in the presence of a sufficient salt concentration for polymerization of said recombinant spider silk protein; and wherein the salt concentration is at least 100 mM, such that it allows polymerization of said spider silk protein;
   c. allowing the spider silk protein to form polymers; and
   d. isolating the spider silk protein polymers,
   wherein the recombinant spider silk protein consists of no more than 800 amino acids, and comprises a set of domains, wherein:
   a. an optional NT-domain, if present, consists of a sequence of 100 to 160 amino-acid residues derived from a N-terminal domain of a spider silk protein, wherein the NT-domain consists of a sequence having at least 50% sequence identity to SEQ ID NO:2 and/or at least 80% sequence identity to any one of SEQ ID NO: 1 and SEQ ID NOs: 80-97;
   b. a REP-domain consists of a sequence of 30 to 600 amino acid residues derived from a repetitive segment of a spider silk protein;
   c. a CT-domain consists of a sequence of 70 to 120 amino acid residues derived from a C-terminal domain of a spider silk protein, wherein the amino acid sequence of the CT-domain is selected from the group consisting of:
      i. a sequence having at least 81% sequence identity to SEQ ID NO:64 or any one of SEQ ID NOs: 62-65 or 67-73; and
      ii. a sequence having at least 80% sequence identity to SEQ ID NO:64 or any one of SEQ ID NOs: 62-65 or 67-73, wherein the sequence comprises at least 7 residues independently selected from K, R, E and D;
   wherein the set of domains is arranged according to the formula (NT)-REP-CT; and
   wherein said recombinant spider silk protein comprises an amino acid sequence having at least 80% sequence identity to the sequence of SEQ ID NO: 11, SEQ ID NO: 14, or SEQ ID NO: 74.

2. The method according to claim 1, wherein said first aqueous liquid medium is:
   (i) a water solution; or
   (ii) a water solution without organic solvents; or
   (iii) an aqueous solution comprising less than 10% (v/v) organic solvents.

3. The method according to claim 1, wherein said first aqueous liquid medium is a water solution.

4. The method according to claim 1, wherein said first aqueous liquid medium is a water solution without organic solvents.

5. The method according to claim 1, wherein said first aqueous liquid medium is an aqueous solution comprising less than 10% (v/v) organic solvents.

6. The method according to claim 1, wherein said recombinant spider silk protein comprises an amino acid sequence having at least 90% sequence identity to the sequence of SEQ ID NO: 11, SEQ ID NO: 14, or SEQ ID NO: 74.

7. The method according to claim 1, wherein said recombinant spider silk protein comprises an amino acid sequence having at least 80% sequence identity to the sequence of SEQ ID NO: 11.

8. The method according to claim 7, wherein said recombinant spider silk protein comprises an amino acid sequence having at least 90% sequence identity to the sequence of SEQ ID NO: 11.

9. The method according to claim 1, wherein the CT-domain is a sequence having at least 80% sequence identity to SEQ ID NO: 64 or SEQ ID NO: 73, wherein the sequence comprises at least 7 residues independently selected from K, R, E and D.

10. The method according to claim 9, wherein the CT-domain is a sequence having at least 80% sequence identity to SEQ ID NO: 64.

11. The method according to claim 10, wherein the CT-domain is a sequence having at least 90% sequence identity to SEQ ID NO: 64.

12. A method for producing a polymer of a recombinant spider silk protein, comprising the steps of:
   a. providing a first aqueous liquid medium comprising a spider silk protein in solution in said medium at a concentration of at least 100 mg/ml;
   b. adjusting the properties of the first aqueous liquid medium such that it allows polymerization of said spider silk protein;
   c. allowing the spider silk protein to form polymers; and
   d. isolating the spider silk protein polymers,
   wherein the recombinant spider silk protein consists of no more than 800 amino acids,
   wherein said recombinant spider silk protein comprises an amino acid sequence having at least 80% sequence identity to the sequence of SEQ ID NO: 11, SEQ ID NO: 14, or SEQ ID NO: 74; and
   wherein said recombinant spider silk protein comprises a CT-domain which consists of a sequence of 70 to 120 amino acid residues derived from a C-terminal domain of a spider silk protein, and which has at least 7 residues independently selected from K, R, E and D.

13. The method according to claim 12, wherein the CT-domain is a sequence having at least 80% sequence identity to SEQ ID NO:64 or any one of SEQ ID NOs: 62-65 or 67-73.

14. The method according to claim 12, wherein the CT-domain is a sequence having at least 80% sequence identity to SEQ ID NO: 64 or SEQ ID NO: 73.

15. The method according to claim 14, wherein the CT-domain is a sequence having at least 80% sequence identity to SEQ ID NO: 64.

16. The method according to claim 15, wherein the CT-domain is a sequence having at least 90% sequence identity to SEQ ID NO: 64.

17. The method according to claim 12, wherein said recombinant spider silk protein comprises an amino acid sequence having at least 90% sequence identity to the sequence of SEQ ID NO: 11, SEQ ID NO: 14, or SEQ ID NO: 74.

18. The method according to claim 17, wherein said recombinant spider silk protein comprises an amino acid sequence having the sequence of SEQ ID NO: 11, SEQ ID NO: 14, or SEQ ID NO: 74.

19. The method according to claim 12, wherein said recombinant spider silk protein comprises an amino acid sequence having at least 80% sequence identity to the sequence of SEQ ID NO: 11.

20. The method according to claim 19, wherein said recombinant spider silk protein comprises an amino acid sequence having at least 90% sequence identity to the sequence of SEQ ID NO: 11.

21. The method according to claim 20, wherein said recombinant spider silk protein comprises an amino acid sequence having the sequence of SEQ ID NO: 11.

22. A polymer of a recombinant spider silk protein, wherein the recombinant spider silk protein consists of no more than 800 amino acids, and comprises a set of domains, wherein:

a. an optional NT-domain, if present, consists of a sequence of 100 to 160 amino-acid residues derived from a N-terminal domain of a spider silk protein, wherein the NT-domain consists of a sequence having at least 50% sequence identity to SEQ ID NO:2 and/or at least 80% sequence identity to any one of SEQ ID NO: 1 and SEQ ID NOs: 80-97;

b. a REP-domain consists of a sequence of 30 to 600 amino acid residues derived from a repetitive segment of a spider silk protein;

c. a CT-domain consists of a sequence of 70 to 120 amino acid residues derived from a C-terminal domain of a spider silk protein, wherein the amino acid sequence of the CT-domain is selected from the group consisting of:

i. a sequence having at least 81% sequence identity to SEQ ID NO:64 or any one of SEQ ID NOs: 62-65 or 67-73; and ii. a sequence having at least 80% sequence identity to SEQ ID NO:64 or any one of SEQ ID NOs: 62-65 or 67-73, wherein the sequence comprises at least 7 residues independently selected from K, R, E and D;

wherein the set of domains is arranged according to the formula (NT)-REP-CT; and wherein said recombinant spider silk protein comprises an amino acid sequence having at least 80% sequence identity to the sequence of SEQ ID NO: 11, SEQ ID NO: 14, or SEQ ID NO: 74.

23. A polymer of a recombinant spider silk protein, wherein the recombinant spider silk protein consists of no more than 800 amino acids, wherein said recombinant spider silk protein comprises an amino acid sequence having at least 80% sequence identity to the sequence of SEQ ID NO: 11, SEQ ID NO: 14, or SEQ ID NO: 74; and wherein said recombinant spider silk protein comprises a CT-domain which consists of a sequence of 70 to 120 amino acid residues derived from a C-terminal domain of a spider silk protein, and which has at least 7 residues independently selected from K, R, E and D.

* * * * *